United States Patent
Ameriks et al.

(10) Patent No.: US 10,604,484 B2
(45) Date of Patent: Mar. 31, 2020

(54) INDOLONE COMPOUNDS AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Suchitra Ravula, San Diego, CA (US); Bradley M. Savall, San Diego, CA (US); Devin M. Swanson, Carlsbad, CA (US); Jeannie M. Ziff, San Diego, CA (US); Brock T. Shireman, Poway, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/569,313

(22) PCT Filed: Apr. 28, 2016

(86) PCT No.: PCT/US2016/029805
§ 371 (c)(1),
(2) Date: Oct. 25, 2017

(87) PCT Pub. No.: WO2016/176463
PCT Pub. Date: Nov. 3, 2016

(65) Prior Publication Data
US 2018/0118683 A1  May 3, 2018

Related U.S. Application Data

(60) Provisional application No. 62/154,315, filed on Apr. 29, 2015.

(51) Int. Cl.

| | | |
|---|---|---|
| C07D 209/34 | (2006.01) |
| C07D 401/04 | (2006.01) |
| C07D 403/12 | (2006.01) |
| C07D 405/12 | (2006.01) |
| C07D 417/12 | (2006.01) |
| C07D 401/10 | (2006.01) |
| C07D 403/10 | (2006.01) |
| C07D 413/10 | (2006.01) |
| A61P 37/00 | (2006.01) |
| A61P 25/28 | (2006.01) |
| A61P 31/18 | (2006.01) |
| A61P 23/00 | (2006.01) |
| A61P 25/18 | (2006.01) |
| A61P 25/24 | (2006.01) |
| A61P 25/00 | (2006.01) |
| A61P 25/16 | (2006.01) |
| A61P 25/06 | (2006.01) |
| A61K 31/4439 | (2006.01) |

(52) U.S. Cl.
CPC ........ *C07D 209/34* (2013.01); *A61K 31/4439* (2013.01); *A61P 23/00* (2018.01); *A61P 25/00* (2018.01); *A61P 25/06* (2018.01); *A61P 25/16* (2018.01); *A61P 25/18* (2018.01); *A61P 25/24* (2018.01); *A61P 25/28* (2018.01); *A61P 31/18* (2018.01); *A61P 37/00* (2018.01); *C07D 401/04* (2013.01); *C07D 401/10* (2013.01); *C07D 403/10* (2013.01); *C07D 403/12* (2013.01); *C07D 405/12* (2013.01); *C07D 413/10* (2013.01); *C07D 417/12* (2013.01)

(58) Field of Classification Search
CPC .......................... C07D 209/34; C07D 401/04
See application file for complete search history.

(56) References Cited

U.S. PATENT DOCUMENTS

| | | |
|---|---|---|
| 4,370,340 A | 1/1983 | Ueda et al. |
| 5,688,809 A | 11/1997 | Macor |
| 5,886,008 A | 3/1999 | Macor |
| 7,842,698 B2 | 11/2010 | Rueckle |

FOREIGN PATENT DOCUMENTS

| | | |
|---|---|---|
| EP | 0869958 | 10/1998 |
| WO | WO 95/21836 | 8/1995 |
| WO | WO 2000/01376 | 1/2000 |
| WO | WO 02/10170 | 2/2002 |
| WO | WO 2002/14294 | 2/2002 |
| WO | WO 2007/135529 | 11/2007 |
| WO | WO 2008/053031 | 5/2008 |
| WO | WO 2008/113795 | 9/2008 |
| WO | WO 2008/148832 | 12/2008 |
| WO | WO 2010/005528 | 1/2010 |
| WO | WO 2010/066658 | 6/2010 |
| WO | WO 2011/056985 | 5/2011 |
| WO | WO 2011/156245 | 12/2011 |
| WO | WO 2013/064984 | 5/2013 |
| WO | WO 2014/085153 | 6/2014 |
| WO | WO 2014/128585 | 8/2014 |

OTHER PUBLICATIONS

Rogawski et al. (Epilepsy Currents, 2011, vol. 11(2), pp. 56-63).*
International Search Report for PCT/US2016/029805 dated Jun. 8, 2016.

(Continued)

*Primary Examiner* — Susanna Moore
(74) *Attorney, Agent, or Firm* — Thomas J. Dodd

(57) ABSTRACT

Provided herein are compounds of Formula (I), and pharmaceutically acceptable salts, N-oxides, or solvates thereof,

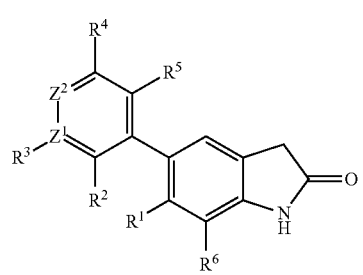

Also provided herein are pharmaceutical compositions, comprising compounds of Formula (I), and methods of using compounds of Formula (I).

39 Claims, No Drawings

(56) References Cited

OTHER PUBLICATIONS

Bagshawe, Drug Dev Res. 1995, 34, 220-230.
Bertolini, et al., J Med Chem. 1997, 40, 2011-2016.
Bodor, Adv Drug Res. 1984, 13, 224-331.
Brewer, G. J. (1997). "Isolation and culture of adult rat hippocampal neurons." Journal of Neuroscience Methods 71(2): 143-155.
Chen et al., Bipolar Disord., 13:1-15, 2011.
Cho et al. (2007). "Two families of TARP isoforms that have distinct effects on the kinetic properties of AMPA receptors and synaptic currents." Neuron 55(6): 890-904.
Du et al., J Neurosci 24: 6578-6589, 2004.
Du et al., J Neurosci 28: 68-79, 2008.
Engin and Treit, Behav Pharmacol 18:365-374, 2007.
Fleisher et al., Adv Drug Delivery Rev., 1996, 19, 115-130.
G.D. Considine, ed., Van Nostrand's Encyclopedia of Chemistry, p. 261, 5$^{th}$ ed. (2005).
Gill and Bredt., Neuropsychopharmacology 36(1): 362-363 (2011).
Harrison, Brain 125:1428-1449, 2002.
Heckers and Konradi, Curr Top Behav Neurosci. 4:529-553, 2010.
Lazzaro et al. (2002). "Functional characterization of CP-465,022, a selective, noncompetitive AMPA receptor antagonist." Neuropharmacology 42(2): 143-153.
McNaughton et al., Behav Pharmacol 18: 329-346, 2007.
Nolen and Bloemkolk, Neuropsychobiology, 42 Suppl 1:11-7, 2000.
Robinson et al., J. Med Chem., 1996, 39(1), 10-18.
Paulekuhn, et al., "Trends in Active Pharmaceutical Ingredient Salt Selection based on Analysis of the Orange Book Database", J. Med. Chem., 2007, 50:6665-72.
S.M. Berge, et al., "Pharmaceutical Salts", J Pharm Sci., 1977, 66:1-19.
Schobel et al., Arch Gen Psych, 66:938-946, 2009.
Shan, et al., J Pharm Sci. 1997, 86 (7), 765-767.
Shi et al (2009) "The stoichiometry of AMPA receptors and TARPs varies by neuronal cell type." Neuron 62(5): 633-640.
Small et al, Nat. Rev. Neurosci. 12:585-601, 2011.
Strange et al. (2006). "Functional characterisation of homomeric ionotropic glutamate receptors GluR1-GluR6 in a fluorescence-based high throughput screening assay." Comb Chem High Throughput Screen 9(2): 147-158.
Tomita et al. (2003). "Functional studies and distribution define a family of transmembrane AMPA receptor regulatory proteins." J Cell Biol 161(4): 805-816.2003.
Tregellas et al., Am J Psychiatry 171: 549-556, 2014.
Yeung et al., Hippocampus 23:278-286, 2013.
Yeung et al., Neuropharmacology 62: 155-160, 2012.
International Search Report for PCT/US2016/029780 dated Jun. 14, 2016.
International Search Report for PCT/US2016/029791 dated Jun. 9, 2016.
International Search Report for PCT/US2016/029801 dated Oct. 17, 2016.
Kambe, Tohru; Correia, Bruno E.; Niphakis, Micah J.; Cravatt, Benjamin F., Journal of the American Chemical Society (2014), 136(30), 10777-10782.
Macor et al., "The discovery of a novel and potent benzodiazepine receptor pharmacophore", Bioorganic & Medicinal Chemistry Letters, Pergamon, Amsterdam, NL, vol. 5, No. 20, Oct. 19, 1995 (Oct. 19, 1995), pp. 2397-2402.
Tikhonova et al.,"Virtual screening of organic molecule databases . Design of focused libraries of potential I igands of NMDA and AMPA receptors", Russian Chemical Bulletin , Kluwer Academic Publishers-Plenum Publishers, NE, vol. 53, No. 6, Jun. 1, 2004, pp. 1335-1344.
Pirotte et al,, "AMPA receptor positive allosteric modulators: a patent review", Expert Opinion Therapeutic Patents, vol. 23, No. 5, 2013, pp. 615-628.
Rowe, Raymond C, Paul J. Sheskey, and Marian E Quinn. Handbook of Pharmaceutical Excipients. London: Pharmaceutical Press, 6th Edition, 2009, p. 17 (Year: 2009).

\* cited by examiner

INDOLONE COMPOUNDS AND THEIR USE AS AMPA RECEPTOR MODULATORS

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA (α-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt., Neuropsychopharmacology 36(1): 362-363 (2011). Several TARPs exhibit regiospecific expression in the brain, leading to physiological differentiation of the AMPA receptor activity. For example, TARP γ2-dependent AMPA receptors are primarily localized in the cerebellum and cerebral cortex while TARP γ8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA γ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anti-convulsant activity are close to or overlap with doses at which undesired effects are observed. (Michael A. Rogawski. "Revisiting AMPA Receptors as an AntiEpileptic Drug Target" Epilepsy Currents 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1'H)-one) are general (non-TARP dependent/non-selective) AMPA receptor antagonists. However, such general antagonism affects most areas of the CNS resulting in undesired effects, Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, Nat. Rev. Neurosci. 12:585-601, 2011). A meta-analysis of post-mortem neuro-pathology studies suggests that hippocampal volume is reduced in volume in patients with mood disorders (Harrison, Brain 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., Bipolar Disord., 13:1-15, 2011). Chronic treatment with mood stabilizers such as lithium or valproate reduced AMPA receptor surface expression in hippocampus (Du et al., J Neurosci 28: 68-79, 2008). Tricyclic antidepressants can trigger mania in bipolar patients (Nolen and Bloemkolk, Neuropsychobiology, 42 Suppl 1:11-7, 2000); these treatments can increase AMPA receptor surface expression in hippocampus (Du et al., J Neurosci 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of GABAA agonists is sufficient to replicate their anxiolytic effects (Engin and Treit, Behav Pharmacol 18:365-374, 2007). Traditional anxiolytics with a variety of mechanisms-of-action, including GABAA-receptor antagonists, 5-HT1A receptor antagonists, and SSRIs, suppress brainstem-stimulated theta rhythm within hippocampus (McNaughton et al., Behav Pharmacol 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., Hippocampus 23:278-286, 2013). Intrahippocampal administration of phenytoin, a voltage-gated sodium channel inhibitor and anti-convulsant, showed similar effects on brainstem-stimulated theta rhythm frequency in anesthetized rat and was anxiolytic in conscious rat (Yeung et al., Neuropharmacology 62: 155-160, 2012).

Hippocampal overactivity has been observed in patients suffering from schizophrenia (Heckers and Konradi, Curr Top Behav Neurosci. 4:529-553, 2010). The degree of hyperactivity was positively correlated to the severity of the symptoms (Tregellas et al., Am J Psychiatry 171: 549-556, 2014). Hypermetabolism in hippocampus (esp. CA1 region) correlates with disease progression in at-risk individuals, and with disease severity in patients diagnosed with schizophrenia (Schobel et al., Arch Gen Psych, 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, Curr Top Behav Neurosci, 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alia, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

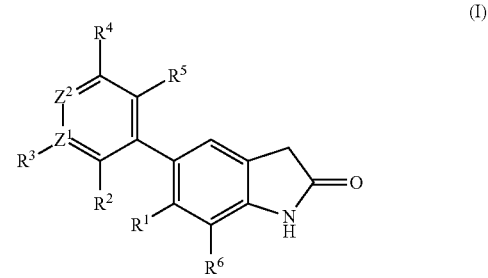

wherein
$R^1$ is H or halo;
$R^6$ is a member selected from the group consisting of: H, halo, —$C_{1-5}$alkyl, —$C_{1-5}$haloalkyl, —$C_{1-5}$alkoxy, —$C_{1-5}$haloalkoxy, and —CN;
$Z^1$ and $Z^2$ are independently C or N, wherein only one $Z^1$ or $Z^2$ may be N;
  (A) when $Z^1$ and $Z^2$ are C; then
  $R^2$ is a member selected from the group consisting of: -halo, —$C_{1-5}$haloalkoxy, —$C_{1-5}$haloalkyl, —CN, and —$CH_2CN$;
  $R^3$ is a member selected from the group consisting of: H, halo, —$C_{1-5}$alkyl, —CN, and —$CH_2CN$;
  $R^4$ is a member selected from the group consisting of: H, halo, —$C_{1-5}$alkyl, —$C_{1-5}$haloalkyl, —CN, and —$CO_2C_{1-5}$alkyl; and $R^5$ is a member selected from the group consisting of: halo; —CH=CH$_2$; —C$_{1-5}$haloalkyl; —C$_{1-5}$haloalkoxy; —CH$_2$CN; —CH(CH$_3$)CN; —C(CH$_3$)$_2$CN; —O—CH$_2$CN; —CO$_2$C$_{1-5}$alkyl; —O-benzyl; —O-cyclopropyl; —O—CH$_2$-cyclopropyl; —O-azetidine substituted with —CO$_2$tBu; —O-thiazole, cyclopropyl substituted with —CN; -cyclobutyl substituted with —CN; phenyl; phenyl substituted with —F, —CN, or —OCH$_3$; cyclopropyl, pyridyl; pyridyl substituted with —F, —OCH$_3$ or —CF$_3$; 1-(2-methoxyethyl)pyrazol-4-yl; 3,5-dimethylisoxazol-4-yl; 2-isopropylpyrazol-3-yl; 1H-pyrazol-4-yl; 1,5-dimethylpyrazol-4-yl); pyrimidin-5-yl; —NHCH$_2$-furyl; —O—CH$_2$cyclopropyl substituted with two —F; and 1-methylpyrazol-4-yl;

(B) when $Z^1$ and $Z^2$ are C and $R^2$ is C$_{1-5}$alkyl; then
$R^3$ is selected from the group consisting of: H, —C$_{1-5}$haloalkyl, —CN, and —CO$_2$C$_{1-5}$alkyl;
$R^4$ is selected from the group consisting of: H, halo, —CN, and —CO$_2$C$_{1-5}$alkyl; and
$R^5$ is selected from the group consisting of: H, halo, —C$_{1-5}$alkyl, —C$_{1-5}$haloalkyl, —C$_{1-5}$alkoxy, —C$_{1-5}$haloalkoxy, —CN, —CO$_2$C$_{1-5}$alkyl, phenyl, 4-fluorophenyl, and 2-fluorophenyl;

(C) when $Z^1$ and $Z^2$ are C and $R^2$ is —C$_{1-5}$alkoxy; then
$R^3$ is selected from the group consisting of: H, halo, and —CO$_2$C$_{1-5}$alkyl;
$R^4$ is selected from the group consisting of: H, halo, —C$_{1-5}$alkyl, and —C$_{1-5}$haloalkyl; and
$R^5$ is selected from the group consisting of: halo, —C$_{1-5}$alkyl, —C$_{1-5}$haloalkyl, —C$_{1-5}$haloalkoxy, quinolinyl, —O-benzyl, and —O—CH$_2$-phenyl substituted with —F;

(D) when $Z^1$ and $Z^2$ are C and $R^5$ is H; then
$R^2$ is selected from the group consisting of: halo, —C$_{1-5}$alkyl, —C$_{1-5}$haloalkyl, —C$_{1-5}$alkoxy, —C$_{1-5}$haloalkoxy, —CH$_2$(C=O)NH(CH$_3$), and —CN;
$R^3$ is selected from the group consisting of: halo, —CN, —CH$_2$CN, —C$_{1-5}$alkyl, —C$_{1-5}$haloalkyl, —C$_{1-5}$alkoxy, —C$_{1-5}$haloalkoxy, —CO$_2$C$_{1-5}$alkyl, piperidine substituted with —OCH$_3$, —O-azetidine substituted with —CO$_2$tBu, —O—CH$_2$cyclopropyl substituted with two —F, and —O-cyclopropyl; and
$R^4$ is selected from the group consisting of: H, halo, —CN, —C$_{1-5}$alkyl, —C$_{1-5}$haloalkyl, and —CO$_2$C$_{1-5}$alkyl;

(E) when one of $Z^1$ or $Z^2$ is N;
$R^2$ is a member selected from the group consisting of: halo, —C$_{1-5}$alkyl, and —C$_{1-5}$alkoxy;
$R^3$ is H or —C$_{1-5}$haloalkyl;
$R^4$ is a member selected from the group consisting of: H and —C$_{1-5}$haloalkoxy; and
$R^5$ is a member selected from the group consisting of: —C$_{1-5}$alkyl, —C$_{1-5}$haloalkoxy, and -halo; and
wherein when $Z^1$ is N, $R^3$ is absent;
or
(F) when $Z^1$ and $Z^2$ are C, and $R^3$ and $R^5$ are H; then
$R^2$ is a member selected from the group consisting of: halo, —C$_{1-5}$alkyl and —C$_{1-5}$alkoxy; and
$R^4$ is a member selected from the group consisting of: halo, —C$_{1-5}$alkyl, —C$_{1-5}$haloalkyl, —CN, —CO$_2$C$_{1-5}$alkyl;

and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds of Formula (I) in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. For example, an $^{18}$F or $^{11}$C labeled compound may be particularly preferred for PET or SPECT studies.

Additional embodiments of this invention include methods of making compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

In another aspect provided herein are compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA).

In a further aspect, provided herein are pharmaceutical compositions, comprising an effective amount of a compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA).

In a further aspect, provided herein are compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA), that are useful as AMPA receptor modulators. Thus, in one embodiment, the compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA), are useful for modulating AMPA receptor activity, as well as treating any condition described herein.

DETAILED DESCRIPTION

In one aspect, provided herein are compounds of Formula (I), and pharmaceutically acceptable salts, N-oxides, or solvates thereof,

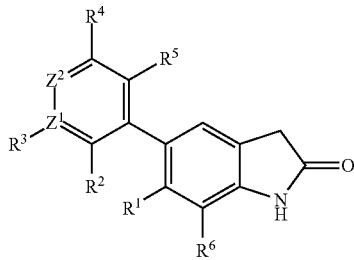

(I)

wherein
$R^1$ is H or halo;
$R^6$ is a member selected from the group consisting of: H, halo, —$C_{1-5}$alkyl, —$C_{1-5}$haloalkyl, —$C_{1-5}$alkoxy, —$C_{1-5}$haloalkoxy, and —CN;
$Z^1$ and $Z^2$ are independently C or N;
wherein only one $Z^1$ or $Z^2$ may be N;
  (A) when $Z^1$ and $Z^2$ are C; then
    $R^2$ is a member selected from the group consisting of: -halo, —$C_{1-5}$haloalkoxy, —$C_{1-5}$haloalkyl, —CN, and —$CH_2CN$;
    $R^3$ is a member selected from the group consisting of: H, halo, —$C_{1-5}$alkyl, —CN, and —$CH_2CN$;
    $R^4$ is a member selected from the group consisting of: H, halo, —$C_{1-5}$alkyl, —$C_{1-5}$haloalkyl, —CN, and —$CO_2C_{1-5}$alkyl; and
    $R^5$ is a member selected from the group consisting of: halo; —CH=$CH_2$; —$C_{1-5}$haloalkyl; —$C_{1-5}$haloalkoxy; —$CH_2CN$; —CH($CH_3$)CN; —C($CH_3$)$_2$CN; —O—$CH_2CN$; —$CO_2C_{1-5}$alkyl; —O-benzyl; —O-cyclopropyl; —O—$CH_2$-cyclopropyl; —O-azetidine substituted with —$CO_2tBu$; —O-thiazole, cyclopropyl substituted with —CN; -cyclobutyl substituted with —CN; phenyl; phenyl substituted with —F, —CN, or —$OCH_3$; cyclopropyl, pyridyl; pyridyl substituted with —F, —$OCH_3$ or —$CF_3$; 1-(2-methoxyethyl)pyrazol-4-yl; 1-methylpyrazol-4-yl; 3,5-dimethylisoxazol-4-yl; 2-isopropylpyrazol-3-yl; 1H-pyrazol-4-yl; 1,5-dimethylpyrazol-4-yl); pyrimidin-5-yl; —$NHCH_2$-furyl; —O—$CH_2$cyclopropyl substituted with two —F; and 1-methylpyrazol-4-yl;
  (B) when $Z^1$ and $Z^2$ are C and $R^2$ is $C_{1-5}$alkyl; then
    $R^3$ is selected from the group consisting of: H, —$C_{1-5}$haloalkyl, —CN, and —$CO_2C_{1-5}$alkyl;
    $R^4$ is selected from the group consisting of: H, halo, —CN, and —$CO_2C_{1-5}$alkyl; and
    $R^5$ is selected from the group consisting of: H, halo, —$C_{1-5}$alkyl, —$C_{1-5}$haloalkyl, —$C_{1-5}$alkoxy, —$C_{1-5}$haloalkoxy, —CN, —$CO_2C_{1-5}$alkyl, phenyl, 4-fluorophenyl, and 2-fluorophenyl;
  (C) when $Z^1$ and $Z^2$ are C and $R^2$ is —$C_{1-5}$alkoxy; then
    $R^3$ is selected from the group consisting of: H, halo, and —$CO_2C_{1-5}$alkyl;
    $R^4$ is selected from the group consisting of: H, halo, —$C_{1-5}$alkyl, and —$C_{1-5}$haloalkyl; and
    $R^5$ is selected from the group consisting of: halo, —$C_{1-5}$alkyl, —$C_{1-5}$haloalkyl, —$C_{1-5}$haloalkoxy, quinolinyl, —O-benzyl, and —O—$CH_2$-phenyl substituted with —F;
  (D) when $Z^1$ and $Z^2$ are C and $R^5$ is H; then
    $R^2$ is selected from the group consisting of: halo, —$C_{1-5}$alkyl, —$C_{1-5}$haloalkyl, —$C_{1-5}$alkoxy, —$C_{1-5}$haloalkoxy, —$CH_2$(C=O)NH($CH_3$), and —CN;
    $R^3$ is selected from the group consisting of: halo, —CN, —$CH_2CN$, —$C_{1-5}$alkyl, —$C_{1-5}$haloalkyl, —$C_{1-5}$alkoxy, —$C_{1-5}$haloalkoxy, —$CO_2C_{1-5}$alkyl, piperidine substituted with —$OCH_3$, —O-azetidine substituted with —$CO_2tBu$, —O—$CH_2$cyclopropyl substituted with two —F, and —O-cyclopropyl; and
    $R^4$ is selected from the group consisting of: H, halo, —CN, —$C_{1-5}$alkyl, —$C_{1-5}$haloalkyl, and —$CO_2C_{1-5}$alkyl;
  (E) when one of $Z^1$ or $Z^2$ is N;
    $R^2$ is a member selected from the group consisting of: halo, —$C_{1-5}$alkyl, and —$C_{1-5}$alkoxy;
    $R^3$ is H or —$C_{1-5}$haloalkyl;
    $R^4$ is a member selected from the group consisting of: H and —$C_{1-5}$haloalkoxy; and
    $R^5$ is a member selected from the group consisting of: —$C_{1-5}$alkyl, —$C_{1-5}$haloalkoxy, and -halo; and
    wherein when $Z^1$ is N, $R^3$ is absent;
  or
  (F) when $Z^1$ and $Z^2$ are C, and $R^3$ and $R^5$ are H; then
    $R^2$ is a member selected from the group consisting of: halo, —$C_{1-5}$alkyl, —$C_{1-5}$alkoxy; and
    $R^4$ is a member selected from the group consisting of: halo, —$C_{1-5}$alkyl, —$C_{1-5}$haloalkyl, —CN, —$CO_2C_{1-5}$alkyl.

An additional embodiment of the invention is a compound of Formula (I) wherein $R^1$ is H.

An additional embodiment of the invention is a compound of Formula (I) wherein $R^1$ is halo.

An additional embodiment of the invention is a compound of Formula (I) wherein $R^1$ is —Br or —F.

An additional embodiment of the invention is a compound of Formula (I) wherein $R^6$ is H.

An additional embodiment of the invention is a compound of Formula (I) wherein $R^6$ is H, halo, —$CH_3$, —$CF_3$, —$OCH_3$, —$OCF_3$, and —CN.

An additional embodiment of the invention is a compound of Formula (I) wherein $R^1$ and $R^6$ are H.

An additional embodiment of the invention is a compound of Formula (I) wherein $Z^1$ and $Z^2$ are C, and $R^2$, $R^3$, $R^4$, and $R^5$ are defined according to (A).

An additional embodiment of the invention is a compound of Formula (I) wherein $Z^1$ and $Z^2$ are C, and $R^2$, $R^4$, and $R^5$ are defined according to (A), and $R^3$ is H, —Cl, —CN, —CH$_3$, or —CH$_2$CN.

An additional embodiment of the invention is a compound of Formula (I) wherein $Z^1$ and $Z^2$ are C, and $R^2$, $R^4$, and $R^5$ are defined according to (A), and $R^3$ is H, —CN.

An additional embodiment of the invention is a compound of Formula (I) wherein $Z^1$ and $Z^2$ are C, and $R^2$ and $R^3$ are defined according to (A), and $R^5$ is —Cl, —Br, —F, —CH$_2$CN, —CH(CH$_3$)CN, —OCF$_2$H, —OCF$_3$, —CH=CH$_2$, —O—CH$_2$CF$_3$, —O—CH$_2$CF$_2$H, —OCH(CH$_3$)CF$_3$, —CF$_3$, —O-benzyl, —CO$_2$CH$_3$, —OCH$_2$CN, cyclopropyl, phenyl,

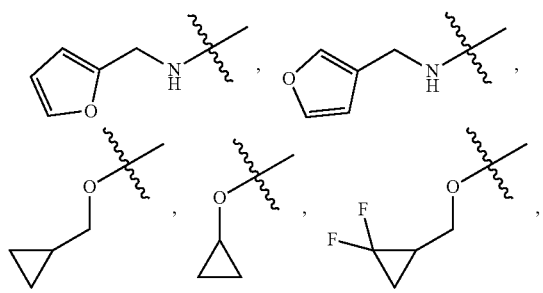

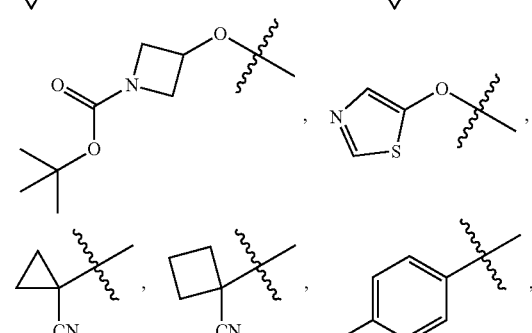

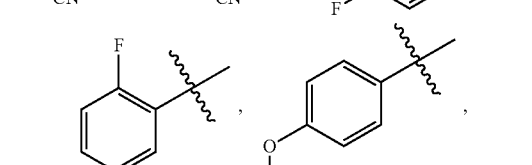

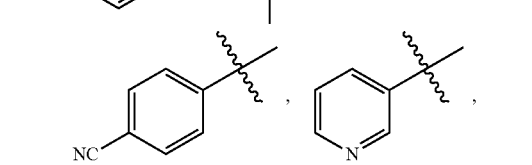

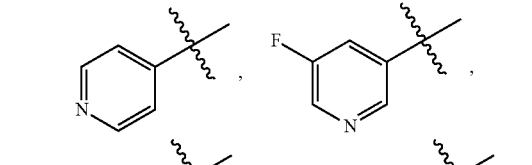

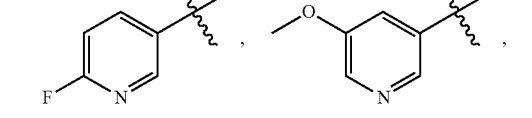

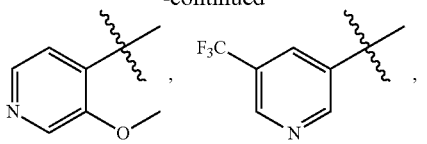

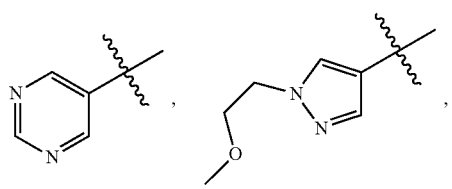

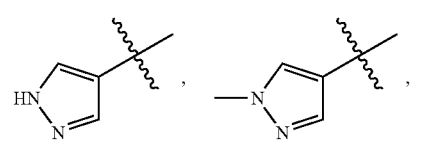

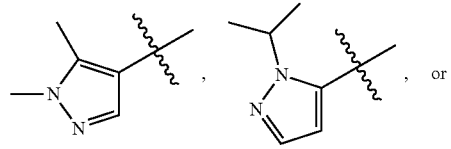

, or

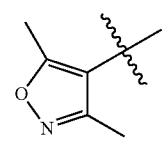

An additional embodiment of the invention is a compound of Formula (I) wherein $Z^1$ and $Z^2$ are C, and $R^2$ and $R^3$, are defined according to (A), and $R^5$ is —Cl, —Br, —F, —CH$_2$CN, —CH(CH$_3$)CN, —OCF$_2$H, or —OCF$_3$.

An additional embodiment of the invention is a compound of Formula (I) wherein $Z^1$ and $Z^2$ are C, and $R^2$, $R^3$, $R^4$, and $R^5$ are defined according to (B).

An additional embodiment of the invention is a compound of Formula (I) wherein $Z^1$ and $Z^2$ are C, and $R^2$, $R^3$, $R^4$, and $R^5$ are defined according to (C).

An additional embodiment of the invention is a compound of Formula (I) wherein $Z^1$ and $Z^2$ are C, and $R^2$, $R^3$, $R^4$, and $R^5$ are defined according to (D).

An additional embodiment of the invention is a compound of Formula (I) wherein $Z^1$ is N, $Z^2$ is C, and $R^2$, $R^4$, and $R^5$ are defined according to (E).

An additional embodiment of the invention is a compound of Formula (I) wherein $Z^1$ is C, $Z^2$ is N, and $R^2$, $R^4$, and $R^5$ are defined according to (E).

An additional embodiment of the invention is a compound of Formula (I) wherein $Z^1$ is C, $Z^2$ is N, $R^4$ is H, $R^3$ is H or —CF$_3$, $R^5$ is defined according to (E), and $R^2$ is —Cl, —OCH$_3$, —OCF$_3$, —OCF$_2$H, or —CH$_3$.

An additional embodiment of the invention is a compound of Formula (I) wherein $Z^2$ is C, $Z^1$ is N, $R^4$ is H, $R^5$ is defined according to (E), and $R^2$ is —Cl, —OCH$_3$, or —CH$_3$.

An additional embodiment of the invention is a compound of Formula (II), and pharmaceutically acceptable salts, N-oxides, or solvates thereof:

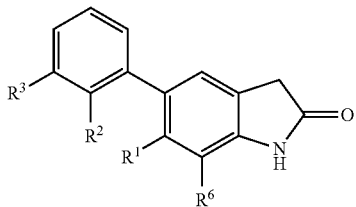

(II)

wherein:
R² is halo or —C₁₋₅alkyl; and
R³ is —CN, piperidine substituted with —OCH₃, or 1-methylpyrazol-4-yl;
and R¹ and R⁶ are as defined as above in Formula (I).

An additional embodiment of the invention is a compound of Formula (II) wherein R⁶ is —H, —F, or —CH₃

An additional embodiment of the invention is a compound of Formula (I), and pharmaceutically acceptable salts, N-oxides, or solvates thereof, as defined in (A), having the structure of Formula (II),

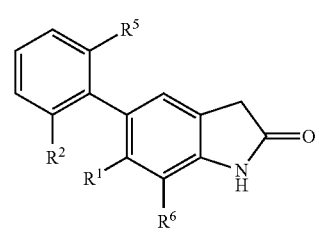

(II)

wherein
R² is halo, —C₁₋₅haloalkoxy or —CN;
R⁵ is halo, —CH₂CN, or —C(CH₃)₂CN;
and R¹ and R⁶ are as defined as above in Formula (I).

An additional embodiment of the invention is a compound of Formula (I), and pharmaceutically acceptable salts, N-oxides, or solvates thereof, as defined in (B), having the structure of Formula (II), (II)

wherein
R² is —C₁₋₅alkyl; and
R⁵ is halo, —C₁₋₅alkyl, —C₁₋₅haloalkyl, —C₁₋₅haloalkoxy or —CN;
and R¹ and R⁶ are as defined as above in Formula (I).

An additional embodiment of the invention is a compound of Formula (I), and pharmaceutically acceptable salts, N-oxides, or solvates thereof, as defined in (C), having the structure of Formula (II),

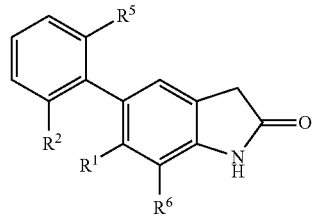

(II)

wherein
R² is —C₁₋₅alkoxy; and
R⁵ is —C₁₋₅haloalkoxy;
and R¹ and R⁶ are as defined as above in Formula (I).

An additional embodiment of the invention is a compound of Formula (III), and pharmaceutically acceptable salts, N-oxides, or solvates thereof:

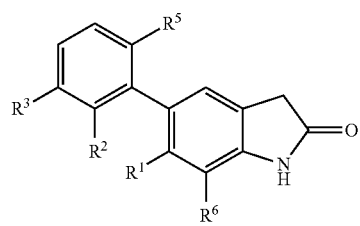

(III)

wherein
R² is halo or —C₁₋₅haloalkoxy;
R³ is —CN; and
R⁵ is halo;
and R¹ and R⁶ are as defined as above in Formula (I).

An additional embodiment of the invention is a compound of Formula (IA), and pharmaceutically acceptable salts, N-oxides, or solvates thereof:

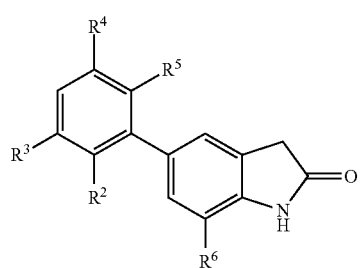

(IA)

wherein:
R² is halo, —C₁₋₅alkyl, —CN, or —C₁₋₅haloalkoxy;
R³ is H or —CN;
R⁴ is H;
R⁵ is halo, —C₁₋₅alkyl, —C₁₋₅haloalkyl, —C₁₋₅alkoxy, —CN, —C(CH₃)₂CN; and
R⁶ is H, halo, —C₁₋₅alkyl, —C₁₋₅haloalkyl, —C₁₋₅alkoxy, —C₁₋₅haloalkoxy or —CN.

An additional embodiment of the invention is a compound of Formula (IA) wherein
R² is C₁₋₅haloalkoxy, or C(CH₃)₂N;
R³ is H or CN;
R⁴ is H;
R⁵ is halo; and
R⁶ is H, halo, —C₁₋₅alkyl, —C₁₋₅haloalkyl, —C₁₋₅alkoxy, —C₁₋₅haloalkoxy or —CN.

Provided herein is a compound selected from the group consisting of compounds of Formula (II), Formula (III), or Formula (IA), or a combination thereof.

A further embodiment of the current invention is a compound as shown below in Table 1.

| Example | Compound name |
|---|---|
| 1 | 5-(2,6-Dimethylphenyl)indolin-2-one; |
| 2 | 5-(2-Bromo-6-chloro-phenyl)indolin-2-one; |
| 3 | 5-(2-Chloro-6-methyl-phenyl)indolin-2-one; |
| 4 | 5-(2,6-Dichlorophenyl)indolin-2-one; |
| 5 | 5-[2-Chloro-6-(trifluoromethoxy)phenyl]indolin-2-one; |
| 6 | 2-[3-Chloro-2-(2-oxoindolin-5-yl)phenyl]acetonitrile; |
| 81 | 2-[3-Chloro-2-(2-oxoindolin-5-yl)phenyl]-2-methyl-propanenitrile; |
| 115 | 4-Chloro-3-(2-oxoindolin-5-yl)-2-(trifluoromethoxy)benzonitrile; |
| 117 | 5-[2-Chloro-6-(trifluoromethoxy)phenyl]-7-fluoro-indolin-2-one; |
| 118 | 5-[2-Chloro-6-(difluoromethoxy)phenyl]-7-fluoro-indolin-2-one; |
| 119 | 2-[3-Chloro-2-(7-fluoro-2-oxo-indolin-5-yl)phenyl]-2-methyl-propanenitrile; |
| 121 | 5-[2-Chloro-3-(4-methoxy-1-piperidyl)phenyl]-7-fluoro-indolin-2-one; |
| 122 | 5-[2-(Difluoromethoxy)-6-methyl-phenyl]-7-fluoro-indolin-2-one; |
| 123 | 5-[2-(Difluoromethoxy)-6-methoxy-phenyl]-7-fluoro-indolin-2-one; |
| 124 | 2-Chloro-3-(7-fluoro-2-oxo-indolin-5-yl)-4-(trifluoromethoxy)benzonitrile; |
| 125 | 5-(3,5-Dimethyl-4-pyridyl)-7-fluoro-indolin-2-one; |
| 126 | 5-(3,5-Dichloro-4-pyridyl)-7-fluoro-indolin-2-one; |
| 127 | 5-[2-Chloro-6-(trifluoromethoxy)phenyl]-7-methyl-indolin-2-one; |
| 128 | 5-[2-Chloro-6-(difluoromethoxy)phenyl]-7-methyl-indolin-2-one; |
| 129 | 5-[2-(Difluoromethoxy)-6-methyl-phenyl]-7-methyl-indolin-2-one; |
| 130 | 5-[2-(Difluoromethoxy)-6-methoxy-phenyl]-7-methyl-indolin-2-one; |
| 131 | 5-[2-(Difluoromethoxy)-6-fluoro-phenyl]-7-methyl-indolin-2-one; |
| 132 | 2-[3-Chloro-2-(7-methyl-2-oxo-indolin-5-yl)phenyl]-2-methyl-propanenitrile; |
| 133 | 4-Chloro-3-(7-methyl-2-oxo-indolin-5-yl)-2-(trifluoromethoxy)benzonitrile; |
| 134 | 2-Methyl-3-(7-methyl-2-oxo-indolin-5-yl)benzonitrile; |
| 135 | 5-(2-Chloro-6-methyl-phenyl)-7-methyl-indolin-2-one; |
| 136 | 5-(2-Fluoro-6-methyl-phenyl)-7-methyl-indolin-2-one; |
| 137 | 7-Methyl-5-[2-methyl-6-(trifluoromethyl)phenyl]indolin-2-one; |
| 138 | 3-Methyl-2-(7-methyl-2-oxo-indolin-5-yl)benzonitrile; |
| 139 | 5-(2-Fluoro-6-methoxy-phenyl)-7-methyl-indolin-2-one; |
| 140 | 5-(2,6-Difluorophenyl)-7-methyl-indolin-2-one; |
| 141 | 5-(2-Chloro-6-fluoro-phenyl)-7-methyl-indolin-2-one; |
| 142 | 5-(2,6-Dimethylphenyl)-7-methyl-indolin-2-one; |
| 143 | 3-Chloro-2-(7-methyl-2-oxo-indolin-5-yl)benzonitrile; |
| 144 | 5-[3,5-Dichloro-2-(trifluoromethyl)-4-pyridyl]-7-methyl-indolin-2-one; |
| 145 | 5-[3-Chloro-5-(trifluoromethoxy)-4-pyridyl]-7-methyl-indolin-2-one; |
| 146 | 5-[3-Chloro-5-(difluoromethoxy)-4-pyridyl]-7-methyl-indolin-2-one; |
| 147 | 5-(3,5-Dichloro-4-pyridyl)-7-methyl-indolin-2-one; |
| 148 | 5-(3,5-Dimethyl-4-pyridyl)-7-methyl-indolin-2-one; |
| 149 | 5-(2-Chloro-4-methyl-3-pyridyl)-7-methyl-indolin-2-one; |
| 150 | 5-(2-Methoxy-4-methyl-3-pyridyl)-7-methyl-indolin-2-one; |
| 151 | 5-(2,4-Dimethyl-3-pyridyl)-7-methyl-indolin-2-one; |
| 152 | 5-(2,4-Dichloro-3-pyridyl)-7-methyl-indolin-2-one; |
| 153 | 7-Chloro-5-[2-chloro-6-(trifluoromethoxy)phenyl]indolin-2-one; |
| 154 | 7-Chloro-5-[2-chloro-6-(difluoromethoxy)phenyl]indolin-2-one; |
| 155 | 2-[3-Chloro-2-(7-chloro-2-oxo-indolin-5-yl)phenyl]-2-methyl-propanenitrile; |
| 156 | 4-Chloro-3-(7-chloro-2-oxo-indolin-5-yl)-2-(trifluoromethoxy)benzonitrile; |
| 157 | 7-Chloro-5-[3-chloro-5-(trifluoromethoxy)-4-pyridyl]indolin-2-one; |
| 158 | 7-Chloro-5-[3-chloro-5-(difluoromethoxy)-4-pyridyl]indolin-2-one; |
| 159 | 7-Chloro-5-(3,5-dichloro-4-pyridyl)indolin-2-one; |
| 160 | 7-Chloro-5-(2-chloro-4-methyl-3-pyridyl)indolin-2-one; |
| 161 | 7-Chloro-5-(2,4-dimethyl-3-pyridyl)indolin-2-one; |
| 162 | 7-Chloro-5-(2-methoxy-4-methyl-3-pyridyl)indolin-2-one; |
| 163 | 7-Chloro-5-(2,4-dichloro-3-pyridyl)indolin-2-one; |
| 164 | 2-(7-Chloro-2-oxo-indolin-5-yl)-3-methyl-benzonitrile; |
| 165 | 7-Chloro-5-(2-chloro-6-methyl-phenyl)indolin-2-one; |
| 166 | 7-Chloro-5-(2-fluoro-6-methyl-phenyl)indolin-2-one; |
| 167 | 7-Chloro-5-[2-methyl-6-(trifluoromethyl)phenyl]indolin-2-one; |
| 168 | 5-[2-Chloro-6-(trifluoromethoxy)phenyl]-7-ethyl-indolin-2-one; |
| 169 | 2-(7-Ethyl-2-oxo-indolin-5-yl)-3-methyl-benzonitrile; |
| 170 | 5-(2-Chloro-6-methyl-phenyl)-7-ethyl-indolin-2-one; |
| 171 | 7-Ethyl-5-(2-fluoro-6-methyl-phenyl)indolin-2-one; |
| 172 | 7-Ethyl-5-[2-methyl-6-(trifluoromethyl)phenyl]indolin-2-one; |
| 173 | 5-(3,5-Dimethyl-4-pyridyl)-7-ethyl-indolin-2-one; |
| 174 | 5-(3,5-Dichloro-4-pyridyl)-7-ethyl-indolin-2-one; |
| 175 | 5-[2-Chloro-6-(trifluoromethoxy)phenyl]-2-oxo-indoline-7-carbonitrile; |
| 176 | 5-[2-Chloro-6-(trifluoromethoxy)phenyl]-7-(trifluoromethyl)-indolin-2-one; |
| 177 | 5-[2-Chloro-6-(trifluoromethoxy)phenyl]-7-(trifluoromethoxy)-indolin-2-one; |
| 178 | 5-[2-Chloro-6-(trifluoromethoxy)phenyl]-7-methoxy-indolin-2-one; and |
| 179 | 5-[2-Chloro-3-(4-methoxy-1-piperidyl)phenyl]indolin-2-one; | and pharmaceutically acceptable salts, N-oxides, or solvates thereof.

A further embodiment of the current invention is a compound as shown below in Table 2.

| Example # | Compound Name |
|---|---|
| 7 | 4-Chloro-3-(2-oxoindolin-5-yl)-2-(trifluoromethoxy)-benzonitrile; |
| 8 | 5-(5-Chloro-2-methyl-phenyl)-indolin-2-one; |
| 9 | 5-[2-Chloro-6-(trifluoromethyl)phenyl]-indolin-2-one; |
| 10 | 5-(2-Isobutoxy-5-methyl-phenyl)-indolin-2-one; |
| 11 | 5-(5-Chloro-2-isopropoxy-phenyl)-indolin-2-one; |
| 12 | 5-(2,5-Dichlorophenyl)-indolin-2-one; |
| 13 | 5-(2-Chloro-5-methyl-phenyl)-indolin-2-one; |
| 14 | 5-[2-Isopropoxy-5-(trifluoromethyl)phenyl]-indolin-2-one; |
| 15 | 5-(2,6-Dichloro-3-methyl-phenyl)-indolin-2-one; |
| 16 | 5-[2-Chloro-5-(trifluoromethyl)phenyl]-indolin-2-one; |
| 17 | 5-(2-Benzyloxy-6-fluoro-phenyl)-indolin-2-one; |
| 18 | 5-[3-Chloro-2-(trifluoromethoxy)phenyl]-indolin-2-one; |
| 19 | 5-[3-Chloro-2-(trifluoromethyl)phenyl]-indolin-2-one; |
| 20 | 5-(2-Chloro-6-methyl-phenyl)-indolin-2-one; |
| 21 | 3-Methyl-2-(2-oxoindolin-5-yl)benzonitrile; |
| 22 | 4-Methyl-3-(2-oxoindolin-5-yl)benzonitrile; |
| 23 | 4-Chloro-3-(2-oxoindolin-5-yl)benzonitrile; |
| 24 | Methyl 3-chloro-2-(2-oxoindolin-5-yl)benzoate; |
| 25 | Methyl 2-chloro-3-(2-oxoindolin-5-yl)benzoate; |
| 26 | Methyl 4-chloro-3-(2-oxoindolin-5-yl)benzoate; |
| 27 | Methyl 3-methyl-2-(2-oxoindolin-5-yl)benzoate; |
| 28 | Methyl 2-methyl-3-(2-oxoindolin-5-yl)benzoate; |
| 29 | Methyl 4-methyl-3-(2-oxoindolin-5-yl)benzoate; |
| 30 | Methyl 2-methoxy-3-(2-oxoindolin-5-yl)benzoate; |
| 31 | 5-(2,6-Difluorophenyl)-indolin-2-one; |
| 32 | 5-(2-Chloro-6-fluoro-phenyl)-indolin-2-one; |
| 33 | 5-(2-Fluoro-6-methyl-phenyl)-indolin-2-one; |
| 34 | 5-(2-Fluoro-6-methoxy-phenyl)-indolin-2-one; |
| 35 | 3-Chloro-2-(2-oxoindolin-5-yl)benzonitrile; |
| 36 | 5-[2-Methyl-6-(trifluoromethyl)phenyl]-indolin-2-one; |
| 37 | 5-(8-Quinolyl)-indolin-2-one; |
| 38 | 5-[2-Methyl-3-(trifluoromethyl)phenyl]-indolin-2-one; |
| 39 | 5-[2-Chloro-3-(trifluoromethyl)phenyl]-indolin-2-one; |
| 40 | 2-Isopropoxy-6-(2-oxoindolin-5-yl)benzonitrile; |
| 41 | 2-Bromo-6-(2-oxoindolin-5-yl)benzonitrile; |
| 42 | 5-(2-Chloro-3-methyl-phenyl)-indolin-2-one; |
| 43 | 2-(2-Oxoindolin-5-yl)-6-(trifluoromethyl)benzonitrile; |
| 44 | 5-(2,3,6-Trichlorophenyl)-indolin-2-one; |
| 45 | 2-Methyl-3-(2-oxoindolin-5-yl)benzonitrile; |
| 46 | 2-Chloro-3-(2-oxoindolin-5-yl)benzonitrile; |
| 47 | 5-(3,5-Dichloro-4-pyridyl)-indolin-2-one; |
| 48 | 5-(2-Chloro-4-methyl-3-pyridyl)-indolin-2-one; |
| 49 | N-Methyl-2-[2-(2-oxoindolin-5-yl)-6-(trifluoromethyl)phenyl]acetamide; |
| 50 | 5-[2-Chloro-6-(2-furylmethylamino)phenyl]-indolin-2-one; |

| Example # | Compound Name |
|---|---|
| 51 | 5-[2-Chloro-6-(3-furylmethylamino)phenyl]-indolin-2-one; |
| 52 | 5-[2-Isopropoxy-6-(trifluoromethoxy) phenyl]-indolin-2-one; |
| 53 | 5-[2-(Cyclopropylmethoxy)-6-(trifluoromethoxy)phenyl]-indolin-2-one; |
| 54 | 5-[2-Chloro-6-(cyclopropoxy)phenyl]-indolin-2-one; |
| 55 | 5-[2-Chloro-6-(cyclopropylmethoxy)phenyl]-indolin-2-one; |
| 56 | (±)-5-[2-Chloro-6-[(2,2-difluorocyclopropyl)methoxy]phenyl]-indolin-2-one; |
| 57 | 5-[2-Chloro-6-(difluoromethoxy)phenyl]-indolin-2-one; |
| 58 | 5-[2-Chloro-6-(2,2,2-trifluoroethoxy) phenyl]-indolin-2-one; |
| 59 | 5-[2-Chloro-6-(2,2-difluoroethoxy)phenyl]-indolin-2-one; |
| 60 | 2-[3-Chloro-2-(2-oxoindolin-5-yl)phenoxy]acetonitrile; |
| 61 | 5-(2-Benzyloxy-6-chloro-phenyl)-indolin-2-one; |
| 62 | tert-Butyl 3-[3-chloro-2-(2-oxoindolin-5-yl)phenoxy]azetidine-1-carboxylate; |
| 63 | 5-(2-Chloro-6-thiazol-5-yloxy-phenyl)-indolin-2-one; |
| 64 | 5-[2-(2,2-Difluoroethoxy)-6-methoxy-phenyl]-indolin-2-one; |
| 65 | 5-[2-Methoxy-6-(2,2,2-trifluoroethoxy)phenyl]-indolin-2-one; |
| 66 | 5-(2-Benzyloxy-6-methoxy-phenyl)-indolin-2-one; |
| 67 | 5-[2-[(4-Fluorophenyl) ethoxy]-6-methoxy-phenyl]-indolin-2-one; |
| 68 | 5-[2-Isopropoxy-6-(trifluoromethyl)phenyl]-indolin-2-one; |
| 69 | 5-[2-Chloro-3-(cyclopropoxy)phenyl]-indolin-2-one; |
| 70 | 5-(2-Chloro-3-isopropoxy-phenyl)-indolin-2-one; |
| 71 | (±)-5-[2-Chloro-3-[(2,2-difluorocyclopropyl)methoxy]phenyl]-indolin-2-one; |
| 72 | 5-[2-Chloro-3-(2,2-difluoroethoxy)phenyl]-indolin-2-one; |
| 73 | 5-[2-Chloro-3-(difluoromethoxy)phenyl]-indolin-2-one; |
| 74 | tert-Butyl 3-[2-chloro-3-(2-oxoindolin-5-yl)phenoxy]azetidine-1-carboxylate; |
| 75 | 5-(3-Chloro-2-isopropoxy-phenyl)-indolin-2-one; |
| 76 | (±)-5-[2-Chloro-6-(2,2,2-trifluoro-1-methyl-ethoxy)phenyl]-indolin-2-one; |
| 77 | (±)-5-[2-Methoxy-6-(2,2,2-trifluoro-1-methyl-ethoxy)phenyl]-indolin-2-one; |
| 78 | 2-[3,4-Dichloro-2-(2-oxoindolin-5-yl)phenyl]acetonitrile; |
| 79 | 2-[2-(2-Oxoindolin-5-yl)-3-trifluoromethoxy)phenyl]acetonitrile; |
| 80 | (±)-2-[3-Chloro-2-(2-oxoindolin-5-yl)phenyl]propanenitrile; |
| 82 | 1-[3-Chloro-2-(2-oxoindolin-5-yl)phenyl] cyclopropanecarbonitrile; |
| 83 | 1-[3-Chloro-2-(2-oxoindolin-5-yl)phenyl]cyclobutanecarbonitrile; |
| 84 | 2-[2-Chloro-3-(2-oxoindolin-5-yl)phenyl]acetonitrile; |
| 85 | 2-[2,4-Dichloro-3-(2-oxoindolin-5-yl)phenyl]acetonitrile; |
| 86 | 2-[3-Bromo-2-(2-oxoindolin-5-yl)phenyl]acetonitrile; |
| 87 | 2-[3-(4-Fluorophenyl)-2-(2-oxoindolin-5-yl)phenyl]acetonitrile; |
| 88 | 2-[3-(2-Fluorophenyl)-2-(2-oxoindolin-5-yl)phenyl]acetonitrile; |
| 89 | 2-[3-(4-Methoxyphenyl)-2-(2-oxoindolin-5-yl)phenyl]-acetonitrile; |
| 90 | 2-[3-Cyclopropyl-2-(2-oxoindolin-5-yl)phenyl]acetonitrile; |
| 91 | 5-(2-Chloro-6-cyclopropyl-phenyl)-indolin-2-one; |
| 92 | 5-(2-Chloro-6-vinyl-phenyl)-indolin-2-one; |
| 93 | 5-(2-Chloro-6-phenyl-phenyl)-indolin-2-one; |
| 94 | 5-[2-Chloro-6-(4-fluorophenyl)phenyl]-indolin-2-one; |
| 95 | 4-[3-Chloro-2-(2-oxoindolin-5-yl)phenyl]benzonitrile; |
| 96 | 5-[2-Chloro-6-(3-pyridyl)phenyl]-indolin-2-one; |
| 97 | 5-[2-Chloro-6-(5-fluoro-3-pyridyl)phenyl]-indolin-2-one; |
| 98 | 5-[2-Chloro-6-(6-fluoro-3-pyridyl)phenyl]-indolin-2-one; |
| 99 | 5-[2-Chloro-6-(5-methoxy-3-pyridyl)phenyl]-indolin-2-one; |
| 100 | 5-[2-Chloro-6-[5-(trifluoromethyl)-3-pyridyl]phenyl]-indolin-2-one; |
| 101 | 5-[2-Chloro-6-(4-pyridyl)phenyl]-indolin-2-one; |
| 102 | 5-[2-Chloro-6-(3-methoxy-4-pyridyl)phenyl]-indolin-2-one; |
| 103 | 5-[2-Chloro-6-[1-(2-methoxyethyl)pyrazol-4-yl]phenyl]-indolin-2-one; |
| 104 | 5-[2-Chloro-6-(1-methylpyrazol-4-yl)phenyl]-indolin-2-one; |
| 105 | 5-[2-Chloro-6-(3,5-dimethylisoxazol-4-yl)phenyl]-indolin-2-one; |
| 106 | 5-[2-Chloro-6-(2-isopropylpyrazol-3-yl)phenyl]-indolin-2-one; |
| 107 | 5-[2-Chloro-6-(1H-pyrazol-4-yl)phenyl]-indolin-2-one; |
| 108 | 5-[2-Chloro-6-(1,5-dimethylpyrazol-4-yl)phenyl]-indolin-2-one; |
| 109 | 5-(2-Chloro-6-pyrimidin-5-yl-phenyl)-indolin-2-one; |
| 110 | 5-(2-Methyl-6-phenyl-phenyl)-indolin-2-one; |
| 111 | 5-[2-(2-Fluorophenyl)-6-methyl-phenyl]-indolin-2-one; |
| 112 | 5-[2-(4-Fluorophenyl)-6-methyl-phenyl]-indolin-2-one; |
| 113 | 5-[2-Methoxy-6-(8-quinolyl)phenyl]-indolin-2-one; |
| 114 | 2-Chloro-3-(2-oxoindolin-5-yl)-4-(trifluoromethoxy) benzonitrile; |
| 116 | 5-(2-Chloro-6-(trifluoromethoxy)phenyl)-6-fluoroindolin-2-one; |
| 120 | 6-Bromo-5-(2-chloro-6-(trifluoromethoxy)phenyl)indolin-2-one; |
| 180 | 2-Chloro-3-(7-methyl-2-oxoindolin-5-yl)-4-(trifluoromethoxy)benzonitrile; |
| 181 | 2-Chloro-3-(7-chloro-2-oxoindolin-5-yl)-4-(trifluoromethoxy)benzonitrile; |
| 182 | 7-Chloro-5-(3,5-dimethylpyridin-4-yl)indolin-2-one; |
| 183 | 7-Chloro-5-(4-chloro-2-methoxypyridin-3-yl)indolin-2-one; and |
| 184 | 7-Methyl-5-(4-chloro-2-methoxypyridin-3-yl)indolin-2-one; | and pharmaceutically acceptable salts, N-oxides, or solvates thereof.

An additional embodiment of the invention is a pharmaceutical composition comprising:

(A) an effective amount of at least one compound of Formula (I):

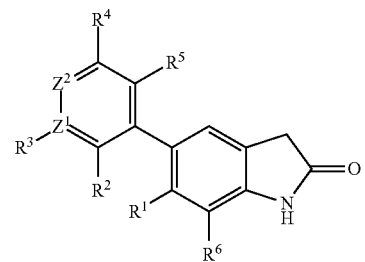

wherein $R^1$ is H or halo;

$R^6$ is a member selected from the group consisting of: H, halo, —$C_{1-5}$alkyl, —$C_{1-5}$haloalkyl, —$C_{1-5}$alkoxy, —$C_{1-5}$haloalkoxy, and —CN;

$Z^1$ and $Z^2$ are independently C or N;

wherein only one $Z^1$ or $Z^2$ may be N;

(A) when $Z^1$ and $Z^2$ are C; then $R^2$ is a member selected from the group consisting of: -halo, —$C_{1-5}$haloalkoxy, —$C_{1-5}$haloalkyl, —CN, and —$CH_2CN$;

$R^3$ is a member selected from the group consisting of: H, halo, —$C_{1-5}$alkyl, —CN, and —$CH_2CN$;

$R^4$ is a member selected from the group consisting of: H, halo, —$C_{1-5}$alkyl, —$C_{1-5}$haloalkyl, —CN, and —$CO_2C_{1-5}$alkyl; and $R^5$ is a member selected from the group consisting of: halo; —CH=$CH_2$; —$C_{1-5}$haloalkyl; —$C_{1-5}$haloalkoxy; —$CH_2CN$; —CH($CH_3$)CN; —C($CH_3$)$_2$CN; —O—$CH_2CN$; —$CO_2C_{1-5}$alkyl; —O-benzyl; —O-cyclopropyl, —O—$CH_2$-cyclopropyl; —O-azetidine substituted with —$CO_2tBu$; —O-thiazole, cyclopropyl substituted with —CN; -cyclobutyl substituted with —CN; phenyl; phenyl substituted with —F, —CN, or —$OCH_3$; cyclopropyl, pyridyl; pyridyl substituted with —F, —$OCH_3$ or —$CF_3$; 1-(2-methoxyethyl)pyrazol-4-yl; 3,5-dimethylisoxazol-4-yl; 2-isopropylpyrazol-3-yl; 1H-pyrazol-4-yl; 1,5-dimethylpyrazol-4-yl); pyrimidin-5-yl; —$NHCH_2$-furyl; —O—$CH_2$cyclopropyl substituted with two —F; and 1-methylpyrazol-4-yl;

(B) when $Z^1$ and $Z^2$ are C and $R^2$ is $C_{1-5}$alkyl; then
$R^3$ is selected from the group consisting of: H, —$C_{1-5}$haloalkyl, —CN, and —$CO_2C_{1-5}$alkyl;
$R^4$ is selected from the group consisting of: H, halo, —CN, and —$CO_2C_{1-5}$alkyl; and
$R^5$ is selected from the group consisting of: H, halo, —$C_{1-5}$alkyl, —$C_{1-5}$haloalkyl, —$C_{1-5}$alkoxy, —$C_{1-5}$haloalkoxy, —CN, —$CO_2C_{1-5}$alkyl, phenyl, 4-fluorophenyl, and 2-fluorophenyl;
(C) when $Z^1$ and $Z^2$ are C and $R^2$ is —$C_{1-5}$alkoxy; then
$R^3$ is selected from the group consisting of: H, halo, and —$CO_2C_{1-5}$alkyl;
$R^4$ is selected from the group consisting of: H, halo, —$C_{1-5}$alkyl, and —$C_{1-5}$haloalkyl; and
$R^5$ is selected from the group consisting of: halo, —$C_{1-5}$alkyl, —$C_{1-5}$haloalkyl, —$C_{1-5}$haloalkoxy, quinolinyl, —O-benzyl, and —O—$CH_2$-phenyl substituted with —F;
(D) when $Z^1$ and $Z^2$ are C and $R^5$ is H; then
$R^2$ is selected from the group consisting of: halo, —$C_{1-5}$alkyl, —$C_{1-5}$haloalkyl, —$C_{1-5}$alkoxy, —$C_{1-5}$haloalkoxy, —$CH_2(C=O)NH(CH_3)$, and —CN;
$R^3$ is selected from the group consisting of: halo, —CN, —$CH_2CN$, —$C_{1-5}$alkyl, —$C_{1-5}$haloalkyl, —$C_{1-5}$alkoxy, —$C_{1-5}$haloalkoxy, —$CO_2C_{1-5}$alkyl, piperidine substituted with —$OCH_3$, —O-azetidine substituted with —$CO_2tBu$, —O—$CH_2$cyclopropyl substituted with two —F, and —O-cyclopropyl; and
$R^4$ is selected from the group consisting of: H, halo, —CN, —$C_{1-5}$alkyl, —$C_{1-5}$haloalkyl, and —$CO_2C_{1-5}$alkyl;
(E) when one of $Z^1$ or $Z^2$ is N;
$R^2$ is a member selected from the group consisting of: halo, —$C_{1-5}$alkyl, and —$C_{1-5}$alkoxy;
$R^3$ is H or —$C_{1-5}$haloalkyl;
$R^4$ is a member selected from the group consisting of: H and —$C_{1-5}$haloalkoxy; and
$R^5$ is a member selected from the group consisting of: —$C_{1-5}$alkyl, —$C_{1-5}$haloalkoxy, and -halo; and
wherein when $Z^1$ is N, $R^3$ is absent;
or
(F) when $Z^1$ and $Z^2$ are C, and $R^3$ and $R^5$ are H; then
$R^2$ is a member selected from the group consisting of: halo, —$C_{1-5}$alkyl, —$C_{1-5}$alkoxy; and
$R^4$ is a member selected from the group consisting of: halo, —$C_{1-5}$alkyl, —$C_{1-5}$haloalkyl, —CN, —$CO_2C_{1-5}$alkyl;
and pharmaceutically acceptable salts, N-oxides or solvates of compounds of Formula (I);
and (B) at least one pharmaceutically acceptable excipient.

An additional embodiment of the invention is a pharmaceutical composition comprising and effective amount of at least one compound of Formula (IA) (as well as Formula (II), and Formula (III), as well as pharmaceutically acceptable salts, N-oxides or solvates of compounds of Formula (IA) (as well as Formula (II), and Formula (III), pharmaceutically acceptable prodrugs of compounds of Formula (IA) (as well as Formula (II), and Formula (III), and pharmaceutically active metabolites of Formula (IA) (as well as Formula (II), and Formula (III); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising and effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are enantiomers and diastereomers of the compounds of Formula (I) (as well as Formula (II), Formula (III), and Formula (IA)). Also within the scope of the invention are the pharmaceutically acceptable salts, N-oxides or solvates of the compounds of Formula (I) (as well as Formula (II), Formula (III), and Formula (IA)). Also within the scope of the invention are the pharmaceutically acceptable prodrugs of compounds of Formula (I) (as well as Formula (II), Formula (III), and Formula (IA)), and pharmaceutically active metabolites of the compounds of Formula (I) (as well as Formula (II), Formula (III), and Formula (IA)).

Also within the scope of the invention are isotopic variations of compounds of Formula (I) (as well as Formula (II), Formula (III), and Formula (IA)), such as, e.g., deuterated compounds of Formula (I). Also within the scope of the invention are the pharmaceutically acceptable salts, N-oxides or solvates of the isotopic variations of the compounds of Formula (I) (as well as Formula (II), Formula (III), and Formula (IA)). Also within the scope of the inventin are the pharmaceutically acceptable prodrugs of the isotopic variations of the compounds of Formula (I) (as well as Formula (II), Formula (III), and Formula (IA)), and pharmaceutically active metabolites of the isotopic variations of the compounds of Formula (I) (as well as Formula (II), Formula (III), and Formula (IA)).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

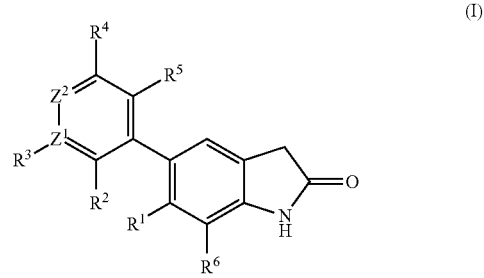

(I)

wherein
$R^1$ is H or halo;
$R^6$ is a member selected from the group consisting of: H, halo, —$C_{1-5}$alkyl, —$C_{1-5}$haloalkyl, —$C_{1-5}$alkoxy, —$C_{1-5}$haloalkoxy, and —CN;
$Z^1$ and $Z^2$ are independently C or N;
wherein only one $Z^1$ or $Z^2$ may be N;
(A) when $Z^1$ and $Z^2$ are C; then
$R^2$ is a member selected from the group consisting of: -halo, —$C_{1-5}$haloalkoxy, —$C_{1-5}$haloalkyl, —CN, and —$CH_2CN$;

$R^3$ is a member selected from the group consisting of: H, halo, —$C_{1-5}$alkyl, —CN, and —$CH_2CN$;
$R^4$ is a member selected from the group consisting of: H, halo, —$C_{1-5}$alkyl, —$C_{1-5}$haloalkyl, —CN, and —$CO_2C_{1-5}$alkyl; and
$R^5$ is a member selected from the group consisting of: halo; —CH=$CH_2$; —$C_{1-5}$haloalkyl; —$C_{1-5}$haloalkoxy; —$CH_2CN$; —CH($CH_3$)CN; —C($CH_3$)$_2$CN; —O—$CH_2CN$; —$CO_2C_{1-5}$alkyl; —O-benzyl; —O-cyclopropyl, —O—$CH_2$-cyclopropyl; —O-azetidine substituted with —$CO_2$tBu; —O-thiazole, cyclopropyl substituted with —CN; -cyclobutyl substituted with —CN; phenyl; phenyl substituted with —F, —CN, or —$OCH_3$; cyclopropyl, pyridyl; pyridyl substituted with —F, —$OCH_3$ or —$CF_3$; 1-(2-methoxyethyl)pyrazol-4-yl; 3,5-dimethylisoxazol-4-yl; 2-isopropylpyrazol-3-yl; 1H-pyrazol-4-yl; 1,5-dimethylpyrazol-4-yl); pyrimidin-5-yl; —$NHCH_2$-furyl; —O—$CH_2$cyclopropyl substituted with two —F; and 1-methylpyrazol-4-yl;

(B) when $Z^1$ and $Z^2$ are C and $R^2$ is $C_{1-5}$alkyl; then
$R^3$ is selected from the group consisting of: H, —$C_{1-5}$ haloalkyl, —CN, and —$CO_2C_{1-5}$alkyl;
$R^4$ is selected from the group consisting of: H, halo, —CN, and —$CO_2C_{1-5}$alkyl; and
$R^5$ is selected from the group consisting of: H, halo, —$C_{1-5}$alkyl, —$C_{1-5}$haloalkyl, —$C_{1-5}$alkoxy, —$C_{1-5}$haloalkoxy, —CN, —$CO_2C_{1-5}$alkyl, phenyl, 4-fluorophenyl, and 2-fluorophenyl;

(C) when $Z^1$ and $Z^2$ are C and $R^2$ is —$C_{1-5}$alkoxy; then
$R^3$ is selected from the group consisting of: H, halo, and —$CO_2C_{1-5}$alkyl;
$R^4$ is selected from the group consisting of: H, halo, —$C_{1-5}$alkyl, and —$C_{1-5}$haloalkyl; and
$R^5$ is selected from the group consisting of: halo, —$C_{1-5}$ alkyl, —$C_{1-5}$haloalkyl, —$C_{1-5}$haloalkoxy, quinolinyl, —O-benzyl, and —O—$CH_2$-phenyl substituted with —F;

(D) when $Z^1$ and $Z^2$ are C and $R^5$ is H; then
$R^2$ is selected from the group consisting of: halo, —$C_{1-5}$ alkyl, —$C_{1-5}$haloalkyl, —$C_{1-5}$alkoxy, —$C_{1-5}$haloalkoxy, —$CH_2$(C=O)NH($CH_3$), and —CN;
$R^3$ is selected from the group consisting of: halo, —CN, —$CH_2CN$, —$C_{1-5}$alkyl, —$C_{1-5}$haloalkyl, —$C_{1-5}$ alkoxy, —$C_{1-5}$haloalkoxy, —$CO_2C_{1-5}$alkyl, piperidine substituted with —$OCH_3$, —O-azetidine substituted with —$CO_2$tBu, —O—$CH_2$cyclopropyl substituted with two —F, and —O-cyclopropyl; and
$R^4$ is selected from the group consisting of: H, halo, —CN, —$C_{1-5}$alkyl, —$C_{1-5}$haloalkyl, and —$CO_2C_{1-5}$ alkyl;

(E) when one of $Z^1$ or $Z^2$ is N;
$R^2$ is a member selected from the group consisting of: halo, —$C_{1-5}$alkyl, and —$C_{1-5}$alkoxy;
$R^3$ is H or —$C_{1-5}$haloalkyl;
$R^4$ is a member selected from the group consisting of: H and —$C_{1-5}$haloalkoxy; and
$R^5$ is a member selected from the group consisting of: —$C_{1-5}$alkyl, —$C_{1-5}$haloalkoxy, and -halo; and
wherein when $Z^1$ is N, $R^3$ is absent;
or (F) when $Z^1$ and $Z^2$ are C, and $R^3$ and $R^5$ are H; then
$R^2$ is a member selected from the group consisting of: halo, —$C_{1-5}$alkyl, and —$C_{1-5}$alkoxy; and
$R^4$ is a member selected from the group consisting of: halo, —$C_{1-5}$alkyl, —$C_{1-5}$haloalkyl, —CN, —$CO_2C_{1-5}$ alkyl;

and pharmaceutically acceptable salts, N-oxides, or solvates thereof, to a subject in need thereof.

In one embodiment of the invention is a method of treating a subject suffering from or diagnosed with a disease, disorder, or medical condition mediated by AMPA receptor activity, comprising administering to a subject in need of such treatment an effective amount of at least one compound selected from a compound of Formula (IA) (as well as Formula (II), and Formula (III), as well as pharmaceutically acceptable salts, N-oxides or solvates of compounds of Formula (IA) (as well as Formula (II), and Formula (III), pharmaceutically acceptable prodrugs of compounds of Formula (IA) (as well as Formula (II), and Formula (III), and pharmaceutically active metabolites of Formula (IA) (as well as Formula (II), and Formula (III).

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxis, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxis, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes.

The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_{1-6}$alkyl group. In some embodiments, an alkyl group is a $C_{1-5}$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_{1-6}$haloalkyl group. In some embodiments, a haloalkyl group is a $C_{1-5}$haloalkyl group. One exemplary substitutent is fluoro. Preferred substituted alkyl groups of the invention include trihalogenated alkyl groups such as trifluoromethyl groups. Haloalkyl includes and is not limited to —$CF_3$, —$CH_2F$, —$CHF_2$, —$CH_2Cl$, —$CH_2$—$CF_3$, and the like.

The term "cycloalkyl" refers to monocyclic, non-aromatic hydrocarbon groups having from 3 to 8 carbon atoms. Examples of cycloalkyl groups include, for example, cyclopropyl, cyclobutyl, cyclopentyl, cyclohexyl, and the like.

The term "alkoxy" includes a straight chain or branched alkyl group with a terminal oxygen linking the alkyl group to the rest of the molecule. In some embodiments, an alkoxy group is a $C_{1-6}$alkoxy group. In some embodiments, an alkoxy group is a $C_{1-5}$alkoxy group. Alkoxy includes methoxy, ethoxy, propoxy, isopropoxy, butoxy, t-butoxy, pentoxy and so on.

The term "haloalkoxy" includes a straight chain or branched alkyl group with a terminal oxygen linking the alkyl group to the rest of the molecule and having at least one of the hydrogens replaced with a halogen. In some embodiments, a haloalkoxy group is a $C_{1-6}$haloalkoxy group. In some embodiments, a haloalkoxy group is a $C_{1-5}$haloalkoxy group. Haloalkoxy includes and is not limited to —$OCF_3$, —$OCH_2F$, —$OCHF_2$, —$OCH_2Cl$, —O—$CH_2$—$CF_3$, and the like.

The term "thiophenyl" and "thienyl" are used interchangeably.

The term "halogen" represents chlorine, fluorine, bromine, or iodine. The term "halo" represents chloro, fluoro, bromo, or iodo.

The term "benzyl" and —$CH_2$-phenyl are used interchangeably

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

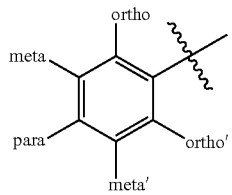

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

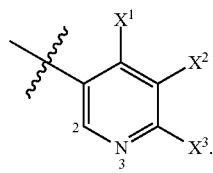

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (–)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

Compounds of the invention may also exist as "rotamers," that is, conformational isomers that occur when the rotation leading to different conformations is hindered, resulting a rotational energy barrier to be overcome to convert from one conformational isomer to another.

The symbols ▬ and ▬ are used as meaning the same spatial arrangement in chemical structures shown herein. Analogously, the symbols ⁞⁞⁞ and ⁞⁞⁞ are used as meaning the same spatial arrangement in chemical structures shown herein.

A wavy line ∼∼ indicates the point of attachment to the rest of the molecule. Additionally, any formula given herein is intended to refer also to hydrates, solvates, and polymorphs of such compounds, and mixtures thereof, even if such forms are not listed explicitly. Certain compounds of Formula (I) (as well as Formula (II), Formula (III), and Formula (IA)), or pharmaceutically acceptable salts of Formula (I) (as well as Formula (II), Formula (III), and Formula (IA)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formula (II), Formula (III), and Formula (IA)) or pharmaceutically acceptable salts of compounds of Formula (I) (as well as Formula (II), Formula (III), and Formula (IA)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^{-}_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^{-}_{(sol)}$ refers to the dissociated form of the compound in a solvent, such as the dissociated form of the compound in an aqueous environment, whether such dissociated form derives from R—COOH, from a salt thereof, or from any other entity that yields R—COO$^{-}$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^{-}_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion+$H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium or tritium (i.e., $^2$H, $^3$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^{2a}$, $R^3$, $R^{3a}$, $R^4$, $R^{4a}$, $R^5$, $R^{5a}$, $R^6$, $Z^1$, $Z^2$, PG, LG, $R^a$, Hal$^1$, and Hal$^2$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The foregoing convention given herein for substituents extends, when applicable, to members such as $R^1$, $R^2$, $R^{2a}$, $R^3$, $R^{3a}$, $R^4$, $R^{4a}$, $R^5$, $R^{5a}$, $R^6$, $Z^1$, $Z^2$, PG, LG, $R^a$, Hal$^1$, and Hal$^2$ and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formula (II), Formula (III), and Formula (IA)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formula (II), Formula (III), and Formula (IA)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and

*Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formula (II), Formula (III), and Formula (IA)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formula (II), Formula (III), and Formula (IA)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formula (II), Formula (III), and Formula (IA)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I) (as well as Formula (II), Formula (III), and Formula (IA)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) (as well as Formula (II), Formula (III), and Formula (IA)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in *"Design of Prodrugs"*, ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formula (II), Formula (III), and Formula (IA)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formula (II), Formula (III), and Formula (IA)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl ($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formula (II), Formula (III), and Formula (IA)), which may also be used in the methods of the invention. A "pharmaceutically active metabolite" means a pharmacologically active product of metabolism in the body of a compound of Formula (I) (as well as Formula (II), Formula (III), and Formula (IA)) (as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formula (II), Formula (III), and Formula (IA)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), as well as Formula (IA). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

TABLE 3

Abbreviations and acronyms used herein include the following.

| Term | Acronym/Abbreviation |
|---|---|
| 1,1'-Azobis(cyclohexanecarbonitrile) | ABCN |
| Acetic anhydride | $Ac_2O$ |
| Acetonitrile | ACN, MeCN |
| Acetic acid | AcOH |
| Azobisisobutyronitirile | AIBN |
| 2,2'-Bis(diphenylphosphino)-1,1'-binaphthyl | BINAP |
| tert-Butylcarbamoyl | BOC |
| Diatomaceous Earth | Celite 545, Celite ® |
| Methylene chloride, dichloromethane | DCM |
| N,N-Diisopropylethylamine | DIPEA, DIEA, Hunig's base |
| N,N-Dimethylformamide | DMF |
| Dimethyl sulfoxide | DMSO |
| Deutero-dimethyl sulfoxide | $DMSO-d_6$ |
| Diphenylphosphino ferrocene | dppf |
| Di-tert-butylphosphino ferrocene | dtbpf |
| Electrospray Ionisation | ESI |
| Ethyl Acetate | EtOAc, or EA, or AcOEt |
| Ethanol | EtOH |
| Flash Column Chromatography | FCC |
| Acetic Acid | HOAc |
| High-pressure liquid chromatography | HPLC |
| Isopropyl Alcohol | IPA |
| Deuteromethanol | $MeOD-d_4$ |
| Methanol | MeOH |
| Sodium tert-butoxide | NaOtBu |
| N-Bromosuccinimide | NBS |
| Tetrakis(triphenylphosphine)palladium(0) | $Pd(PPh_3)_4$ |
| Tris(dibenzylideneacetone(dipalladium (0) | $Pd_2(dba)_3$ |

TABLE 3-continued

Abbreviations and acronyms used herein include the following.

| Term | Acronym/Abbreviation |
| --- | --- |
| [1,1'-Bis(di-tert-butylphosphino)ferrocene]dichloropalladium(II) | PdCl$_2$(dtbpf) |
| Palladium(II)bis(triphenylphosphine) dichloride, bis(triphenylphosphine)palladium(II) dichloride | PdCl$_2$(PPh$_3$)$_2$ |
| Triphenylphosphine | PPh$_3$ |
| Precipitate | ppt |
| Room temperature | rt |
| [2-(Trimethylsilyl)ethoxy]methyl acetal | SEM |
| Supercritical Fluid Chromatography | SFC |
| Triethyl amine | TEA |
| Trifluoroacetic acid | TFA |
| Trifluoroacetic anhydride | TFAA |
| Tetrahydrofuran | THF |

PREPARATIVE EXAMPLES

Exemplary compounds useful in methods of the invention will now be described by reference to the illustrative synthetic schemes for their general preparation below and the specific examples to follow.

$R^{2a}$ is —OH. For example, reaction with an acid such as HCl, in a solvent such as dioxane, ether and the like, at temperatures ranging from 20-50° C., affords a compound of formula (IV). In a preferred method, the acid is HCl in dioxane. In a similar method, a compound of formula (IId), where one $Z^1$ or $Z^2$ is N, $R^5$ is —Cl, and $R^a$ is H, is also protected with a suitable protecting group, employing methods previously described to provide a compound of formula (IIId). A compound of formula (III) is reacted under metalation/halogenation conditions previously described to provide a compound of formula (IV) where one $Z^1$ or $Z^2$ is N, $R^5$ is —Cl, $R^a$ is H, and Hal$^1$ is —I. Removal of the protecting group in a compound of formula (III) using conditions known to one skilled in the art affords a compound of formula (IV), where $R^{2a}$ is —OH.

In an alternate method, a compound of formula (IId), where $R^a$ is —C$_{1-5}$haloalkyl and $R^5$ is —Cl, is deprotonated with a strong base such as n-butyllithium (n-BuLi), and the like, at a temperature such as −78° C., in a suitable solvent such as THF, and the like, and an electrophilic halogen source such as I$_2$, Br$_2$, N-iodosuccinimide (NIS), N-bromosuccinimide (NBS), and the like, to provide a compound of formula (IV), where Hal$^1$ is —I or —Br, $R^{2a}$ is —C$_{1-5}$haloalkoxy, and $R^5$ is —Cl.

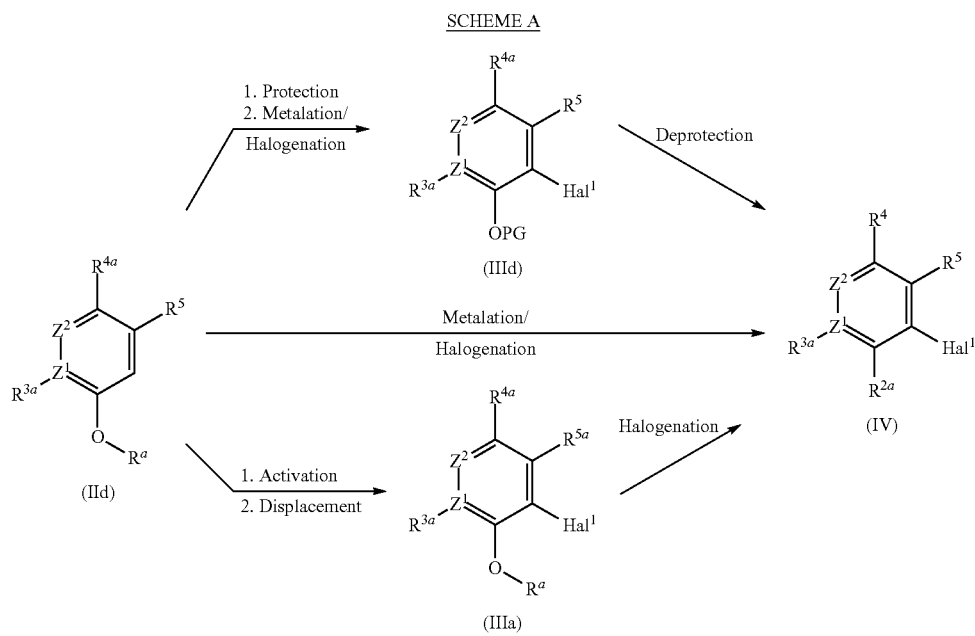

SCHEME A

According to SCHEME A, a phenol compound of formula (IId), where $Z^1$ and $Z^2$ are C, $R^5$ is —Cl, and $R^a$ is H, is protected with a protecting group (PG), where PG is a conventional phenol protecting group, such as methoxymethyl ether (MOM), under conditions known to one skilled in the art. Subsequent metalation followed by halogenation provides a compound of formula (IIId). For example, reaction of a protected phenol with a strong base such as n-butyllithium (n-BuLi), and the like, at a temperature such as −78° C., in a suitable solvent such as THF, and the like, and an electrophilic halogen source such as iodine provides a compound of formula (IIId), where Hal$^1$ is —I, and PG is methoxymethyl ether. Removal of the protecting group in a compound of formula (IIId) using conditions known to one skilled in the art affords a compound of formula (IV), where A phenol compound of formula (IId), where $Z^1$ and $Z^2$ are C, $R^{4a}$ is —OH, $R^5$ is —Cl, $R^a$ is —C$_{1-5}$haloalkyl, is reacted with trifluoromethanesulfonic anhydride, a suitable base such as potassium phosphate, in a solvent such as toluene, and the like, at a temperature of about 0° C. to rt, to provide an activated compound of formula (IIIa), where $R^{4a}$ is —OLG, where LG is a triflate. Displacement of —OLG, where LG is a triflate, in a compound of formula (IIIa) with a cyanide source, such as zinc cyanide, in the presence of a palladium catalyst such as Pd(PPh$_3$)$_4$, and the like, in a suitable solvent such as DMF, employing conventional heating, at a temperature such as 120° C., provides a benzonitrile compound of formula (IIIa), where $R^{4a}$ is —CN. A benzonitrile compound of formula (IIIa), where $R^{4a}$ is —CN, is deprotonated with a mixed Zn/Li base such as zinc chloro 2,2,6,6-tetramethylpiperidide lithium chloride complex (TMPZnCl*LiCl), in a suitable solvent such as THF, employing conventional heating at a temperature such as 60° C. for a period of 16 h, and then treated with an electrophile such as iodine at a temperature such as 60° C. to provide a compound of formula (IV) where $R^4$ is —CN, and $Hal^1$ is —I.

provide a methylbromide compound where $R^{5a}$ is —$CH_2Br$. Subsequent reaction of a methylbromide compound, where $R^{5a}$ is —$CH_2Br$, with a cyanide source such as potassium cyanide, in a suitable solvent such as DMF and water, employing conventional heating, at a temperature such as 40° C., provides a compound of formula (IX), where $R^5$ is —$CH_2CN$.

SCHEME B

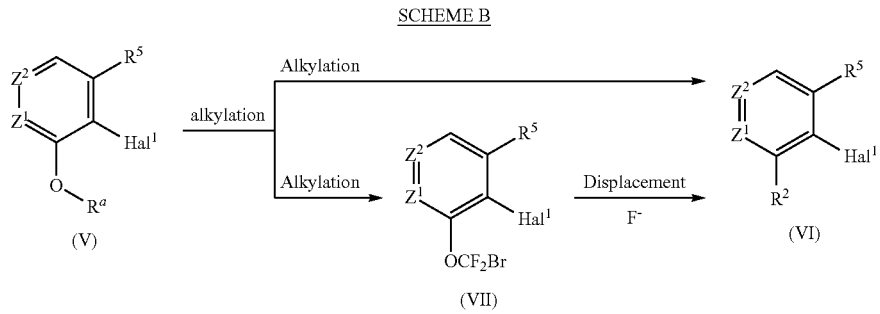

According to SCHEME B, a compound of formula (V), where $R^5$ is halo, $Z^1$ or $Z^2$ are C or N (wherein both $Z^1$ and $Z^2$ cannot be N), $Hal^1$ is —I, and $R^a$ is H; is treated with an alkylating reagent such as sodium chlorodifluoroacetate or diethyl (bromodifluoromethyl)phosphonate, in the presence of a base such as potassium hydroxide, cesium carbonate, and the like, in a suitable solvent such as acetonitrile, DMF, water, and the like, employing conventional heating and cooling, at temperatures ranging from −78° C. to 100° C., to provide a difluoromethoxy compound of formula (VI) where $R^2$ is —$C_{1-5}$haloalkoxy.

A compound of formula (V), where $R^5$ is halo, $Z^1$ or $Z^2$ are C or N (wherein both $Z^1$ and $Z^2$ cannot be N), $Hal^1$ is —I, and $R^a$ is H; is treated with an alkylating reagent such as dibromodifluoromethane, and the like, in the presence of a base such a potassium tert-butoxide, in a suitable solvent such as DMF, employing conventional cooling and heating, at temperatures ranging from 0° C. to 80° C., to provide a bromodifluoromethoxy compound of formula (VII). A bromodifluoromethoxy compound of formula (VII) is treated with a fluoride source such as silver tetrafluoroborate, in a suitable solvent such as DCM, employing conventional cooling, at temperatures ranging from −78° C. to rt, to provide a trifluoromethoxy compound of formula (VI) where $R^2$ is —$C_{1-5}$haloalkoxy.

SCHEME C

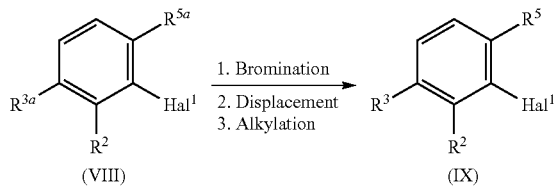

According to SCHEME C, a compound of formula (VIII), where $R^2$ is halo, $R^{5a}$ is —$CH_3$, and $Hal^1$ is —I, is treated with a brominating reagent such as NBS, in the presence of a suitable catalyst such as AIBN, ABCN, and the like, in a suitable solvent such as carbon tetrachloride, employing conventional heating, at a temperature such as 90° C., to A compound of formula (IX), where $R^5$ is —$CH_2CN$, is further reacted with an alkylating agent such as iodomethane, 1,2-dibromoethane, 1,3-dibromopropane, and the like, in the presence of a base such as lithium diisopropylamide (LDA), NaH, and the like, in a suitable solvent such as DMF or THF, employing conventional cooling at temperatures ranging from −78° C. to rt, to provide a compound of formula (IX), where $R^5$ is —$CH(CH_3)CN$, —$C(CH_3)_2CN$, or —$C_{3-6}$cycloalkyl substituted with CN.

SCHEME D

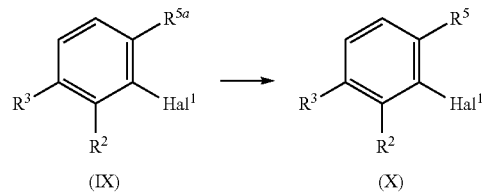

According to SCHEME D, a methylbromide compound of formula (IX) where $R^2$ is -halo, $R^{5a}$ is —$CH_2Br$, and $Hal^1$ is —I, is reacted in a displacement reaction with a commercially available or synthetically accessible optionally substituted 5-6 membered heterocyclic amine, such as morpholine, piperidine, N-methylpiperazine, and the like, in the presence of base such as triethylamine, in a suitable solvent such as DCM to afford a compound of formula (X), where $R^2$ is —Cl, $R^5$ is an optionally substituted 5-6 membered heterocyclic amine, such as morpholinyl, piperidinyl, or N-methylpiperazinyl, and $Hal^1$ is —I.

SCHEME E

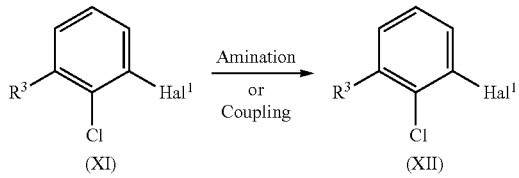

According to SCHEME D, a compound of formula (XI), where $R^3$ is —Br, and $Hal^1$ is —Br, is aminated under conditions known to one of skill in the art, to provide a compound of formula (XII). For example, a compound of formula (XI), where $R^3$ is —Br, and $Hal^1$ is —Br, is treated with a suitable primary or secondary cyclic or acyclic amine, in the presence of a palladium catalyst such as $Pd_2(dba)_3$, and the like, a phosphine ligand such as BINAP, and the like, a suitable base such as sodium tert-butoxide (NaOt-Bu), and the like, in a solvent such as toluene, and the like, employing conventional or microwave heating, at a temperature such as 140° C., to provide a compound of formula (XII), where $R^2$ is —Cl, $R^3$ is 4-methoxypiperdinyl, and $Hal^1$ is —Br. In a preferred method, the catalyst is $Pd_2(dba)_3$.

A compound of formula (VII), where $R^2$ is —Cl, $R^3$ is —Br, and $Hal^1$ is —Br, is coupled under Suzuki reaction conditions known to one skilled in the art with a commercially available or synthetically accessible suitable aryl or heteroaryl boronic acid or boronic ester, in the presence of a palladium catalyst such as $PdCl_2(dppf)\text{-}CH_2Cl_2$, $PdCl_2$(dtbpf), and the like, a suitable base such a potassium phosphate, and the like, in a solvent such as dioxane, water, or a mixture thereof, employing conventional or microwave heating, at a temperature such as 100° C., to provide a compound of formula (VIII), where $R^2$ is —Cl, $R^3$ is an optionally substituted aryl or heteroaryl, and $Hal^1$ is —Br.

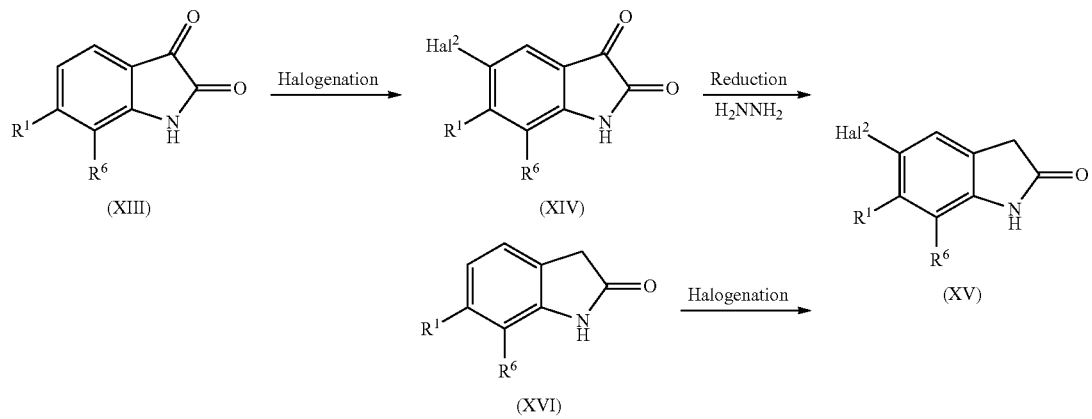

SCHEME E (XIII) → Halogenation → (XIV) → Reduction $H_2NNH_2$ → (XV)

(XVI) → Halogenation → (XV)

According to SCHEME E, a commercially available or synthetically accessible isatin compound of formula (XIII), where $R^6$ is $C_{1-5}$haloalkyl, $C_{1-5}$haloalkoxy, or —$C_{1-5}$alkoxy, is treated with an electrophilic halogen source such as bromine, in a suitable solvent such as AcOH, to provide a compound of formula (XIV), where $Hal^2$ is —Br. A compound of formula (XIV) is treated with hydrazine, in a suitable solvent such as n-butanol, employing conventional heating, at a temperature such as 80° C., followed by treatment with a base such as trimethylamine, and further heating at a temperature such as 100° C., to provide a compound of formula (XV), $Hal^2$ is —Br and $R^6$ is $C_{1-5}$haloalkyl, $C_{1-5}$haloalkoxy, or —$C_{1-5}$alkoxy.

In an alternate method, an indolone compound of formula (XVI), where $R^6$ is halo, —$C_{1-5}$alkyl, or —CN, is treated with an electrophilic halogen source such as NBS, in a solvent such as TFA, employing conventional cooling, at a temperature such as 0° C., to provide a compound of formula (XV), where $Hal^2$ is —Br and $R^6$ is halo, —$C_{1-5}$alkyl, or —CN.

SCHEME F

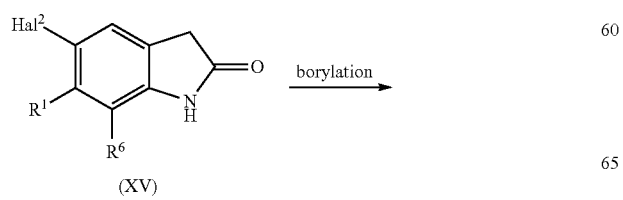

(XV) → borylation →

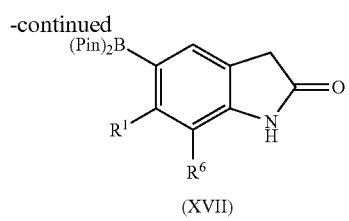

(XVII)

According to SCHEME F, a commercially available or synthetically accessible compound of formula (XV), where $R^1$ is —H or halo, $R^6$ is H, halo, —$C_{1-5}$alkyl, —$C_{1-5}$haloalkyl, —$C_{1-5}$alkoxy, —$C_{1-5}$haloalkoxy, or —CN, and $Hal^2$ is —Br, is treated with bis(pinacolato)diboron in the presence of a palladium catalyst such as $PdCl_2(dppf)\text{-}CH_2Cl_2$, $Pd_2(dba)_3$, and the like, a base such as potassium acetate, in a suitable solvent such as dioxane, DMF, and the like, employing conventional heating, at a temperature ranging from 60-85° C., for a period of about 12-18 h, to provide a compound of formula (XVII).

SCHEME G

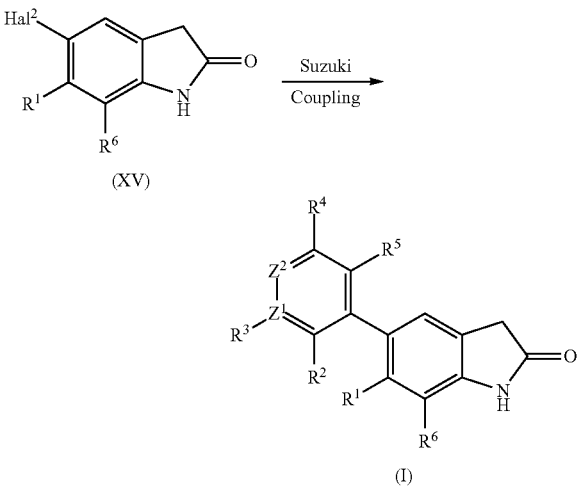

According to SCHEME G, a compound of formula (XV), where $Hal^2$ is —Br, $R^1$ and $R^6$ are as defined in Formula (I), is coupled in a Suzuki reaction with a commercially available or synthetically accessible suitably substituted phenyl or pyridyl boronic acid or ester, in the presence of a palladium catalyst such as $PdCl_2(dppf)\text{-}CH_2Cl_2$, $PdCl_2$(dt-bpf), $Pd_2(dba)_3$, and the like, with our without dicyclohexyl (2',6'-dimethoxy-[1,1'-biphenyl]-2-yl)phosphine, a suitable base such a potassium phosphate, and the like, in a solvent such as toluene, dioxane, water, or a mixture thereof, employing conventional or microwave heating, at a temperature such as 100° C., to provide a compound of Formula (I).

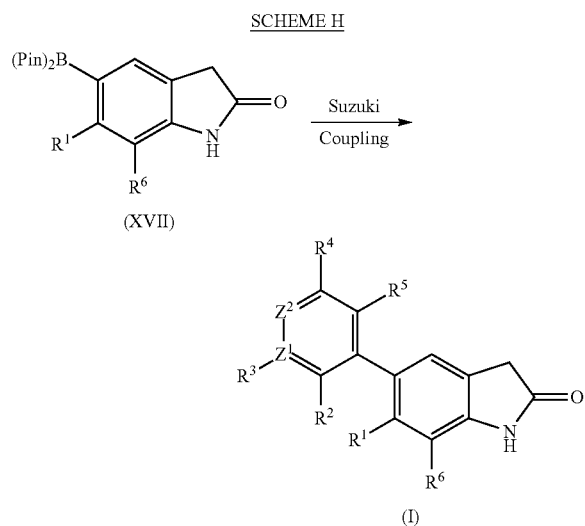

SCHEME H

According to SCHEME H, a compound of formula (XVII), where $R^1$ and $R^6$ are as defined in Formula (I), is coupled in Suzuki reaction, employing methods previously described, with a commercially available or synthetically accessible suitably substituted compound of formula (IV), (VI), (IX), (X), or (XII) as previously described in the schemes above, to provide a compound of Formula (I).

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, $CH_3OH$, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via $^1/_{16}$" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 µM, 30×100 or 50×150 mm) or an XBridge C18 OBD column (5 µM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 µm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 µm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 µm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an SFC system on a Berger instrument (APS 1010), or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1:
1-Chloro-2-iodo-3-(trifluoromethoxy)benzene

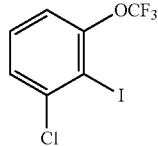 [SMILES: FC(F)(F)Oc1cccc(Cl)c1I]

To a cooled (−78° C.) solution of 1-chloro-3-(trifluoromethoxy)benzene (20 g, 102 mmol) in THF (100 mL) was added n-butyllithium (2.5 M/hexanes, 41 mL, 102 mmol) dropwise over a period of 10 minutes. Stirring was maintained at −78° C. for 1 h, and then a solution of iodine (26 g, 102 mmol) in THF (100 mL) was added dropwise at −78° C. over a period of 30 minutes. After the addition, the temperature was maintained at −78° C. for 1 h and then allowed to warm to rt and stirred for a total of 18 h. The reaction mixture was poured into saturated aqueous $Na_2SO_3$ and extracted with EtOAc (2×200 mL). The combined organic extracts were dried over $Na_2SO_4$ and concentrated in vacuo to give the title compound as an oil (28 g, 85% yield). $^1$H NMR (500 MHz, CDCl$_3$) δ 7.40 (dd, J=8.1, 1.4 Hz, 1H), 7.32 (t, J=8.1 Hz, 1H), 7.16 (dt, J=8.2, 1.4 Hz, 1H).

Intermediate 2:
2-(3-Chloro-2-iodophenyl)acetonitrile

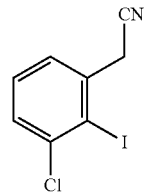

Step A: 1-(Bromomethyl)-3-chloro-2-iodobenzene

To a solution of 1-chloro-2-iodo-3-methylbenzene (4.0 g, 16 mmol) in CCl$_4$ (12 mL), were added N-bromosuccinimide (5.6 g, 32 mmol) and 1,1'-azobis(cyclohexanecarbonitrile) (AIBN) (3.9 g, 16 mmol). The mixture was degassed with nitrogen and then heated at 90° C. for 1 h. After cooling to rt, silica gel was added, and the solvent was removed in vacuo. Purification (FCC, SiO$_2$; 0-5% EtOAc/hexanes) provided the title compound as an oil (3.7 g, 70% yield). $^1$H NMR (400 MHz, CDCl$_3$): δ 7.37 (m, 2H), 7.29-7.23 (m, 1H), 4.65 (s, 2H).

Step B: 2-(3-Chloro-2-iodophenyl)acetonitrile

To a solution of 1-(bromomethyl)-3-chloro-2-iodobenzene (1.0 g, 3.0 mmol) in DMF (13 mL) was added a solution of potassium cyanide (236 mg, 3.6 mmol) in water (1.3 mL). The mixture was stirred at 40° C. for 1 h. The reaction mixture was cooled to rt, diluted with water, and extracted with EtOAc (2×). The organic extracts were dried over $Na_2SO_4$, and concentrated to obtain the product as white solid (770 mg, 92% yield). $^1$H NMR (500 MHz, CDCl$_3$) δ 7.44 (m, 2H), 7.36-7.33 (m, 1H), 3.93-3.83 (m, 2H).

Intermediate 3:
2-Chloro-3-iodo-4-(trifluoromethoxy)benzonitrile

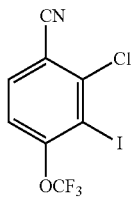 [SMILES: N#Cc1ccc(OC(F)(F)F)c(I)c1Cl]

Step A: 2-Chloro-4-(trifluoromethoxy)phenyltrifluoromethanesulfonate

To a cold (0° C.) solution of 2-chloro-4-(trifluoromethoxy)phenol (1.0 g, 4.7 mmol) in toluene (12.5 mL) was added 30 wt % aqueous potassium phosphate (12.5 mL). After 10 minutes at 0° C., trifluoromethanesulfonic anhydride (0.95 mL, 5.7 mmol) was added dropwise and the resulting mixture was stirred at rt for 2 h. The aqueous phase was separated and the organic phase was washed with water, dried over $Na_2SO_4$, and concentrated to obtain the title compound which was used crude in the next step without further purification.

Step B. 2-Chloro-4-(trifluoromethoxy)benzonitrile

2-Chloro-4-(trifluoromethoxy)phenyltrifluoromethanesulfonate was dissolved in DMF (4.0 mL), followed by addition of zinc cyanide (681 mg, 5.8 mmol) and tetrakis(triphenylphosphine)palladium (Pd(PPh$_3$)$_4$) (335 mg, 0.3 mmol). The reaction mixture was degassed with nitrogen for 10 minutes and then heated at 120° C. for 2 h. After cooling to rt, the crude reaction mixture was diluted with saturated aqueous NaHCO$_3$ solution, and extracted with EtOAc (×3). The combined organic extracts were dried over $Na_2SO_4$ and concentrated. Purification (FCC, SiO$_2$; 0-5% EtOAc/hexanes) provided the title compound as an oil (220 mg, 34% yield). $^1$H NMR (500 MHz, DMSO-d$_6$) δ 8.16 (d, J=8.7 Hz, 1H), 7.93 (dd, J=2.2, 1.0 Hz, 1H), 7.66-6.56 (m, 1H).

Step C:
2-Chloro-3-iodo-4-(trifluoromethoxy)benzonitrile

To a solution of 2-chloro-4-(trifluoromethoxy)benzonitrile (90 mg, 0.41 mmol) in THF (0.5 mL) was added TMPZnCl*LiCl (1.0 M, 0.5 mL, 0.5 mmol) and the mixture was stirred at 60° C. for 16 h. A solution of iodine (101 mg, 0.40 mmol) in THF (2.0 mL) was added to the warm reaction mixture and stirring was maintained at 60° C. for 15 minutes. After cooling to rt, the reaction was quenched with saturated aqueous sodium thiosulfate and extracted with EtOAc (×3). The combined organic extracts were dried over Na$_2$SO$_4$, concentrated in vacuo. Purification (FCC, SiO$_2$, 0-5% EtOAc/hexanes) afforded the title compound as a white solid (105 mg, 74% yield). $^1$H NMR (400 MHz, DMSO-d$_6$) δ 8.15 (d, J=8.7 Hz, 1H), 7.60 (dq, J=8.6, 1.5 Hz, 1H).

Intermediate 4: 7-Fluoro-5-(4,4,5,5-tetramethyl-1,3,2-dioxaborolan-2-yl)indolin-2-one

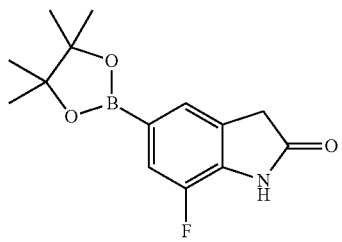 [SMILES: CC1(C)OB(c2cc(F)c3c(c2)CC(=O)N3)OC1(C)C]

To a solution of 5-bromo-7-fluoroindolin-2-one (585 mg, 2.54 mmol) in dioxane (8.0 mL) was added potassium acetate (500 mg, 5.0 mmol), bis(pinacolato)diboron (775 mg, 3.05 mmol) and PdCl$_2$(dppf)-CH$_2$Cl$_2$ (186 mg, 0.25 mmol). The solution was degassed with nitrogen and then heated at 85° C. for 2 h. After cooling to rt, the reaction mixture was diluted with brine and extracted with EtOAc (×2). The combined organic extracts were dried over Na$_2$SO$_4$, concentrated, and the crude product was triturated with DCM to provide the title compound as a white solid (535 mg, 75% yield). MS (ESI): mass calcd. for C$_{14}$H$_{17}$BFNO$_3$, 277.1; m/z found, 278.1 [M+H]$^+$. $^1$H NMR (500 MHz, DMSO-d$_6$) δ 11.02 (s, 1H), 7.37-7.26 (m, 1H), 7.30-7.20 (m, 1H), 3.57-3.56 (m, 2H), 1.28 (s, 12H).

Intermediate 5: 7-Methyl-5-(4,4,5,5-tetramethyl-1,3,2-dioxaborolan-2-yl)indolin-2-one

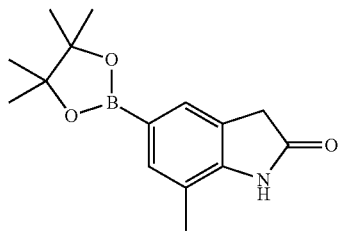 [SMILES: Cc1cc(B2OC(C)(C)C(C)(C)O2)cc2c1NC(=O)C2]

The title compound was prepared in a manner analogous to Intermediate 4, substituting 5-bromo-7-methylindolin-2-one for 5-bromo-7-fluoroindolin-2-one. The crude product was triturated with DCM to provide the title compound as a white solid (54% yield). MS (ESI): mass calcd. for C$_{16}$H$_{12}$ClF$_2$NO$_2$, 273.1; m/z found, 275.1 [M+H]$^+$. $^1$H NMR (400 MHz, DMSO-d$_6$) δ 10.55 (s, 1H), 7.32 (s, 1H), 7.31 (s, 1H), 3.47 (s, 2H), 2.19 (s, 3H), 1.26 (s, 12H).

Intermediate 6: 4-Chloro-3-iodo-2-(trifluoromethoxy)benzonitrile

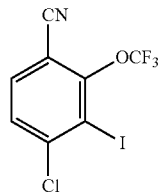 [SMILES: N#Cc1ccc(Cl)c(I)c1OC(F)(F)F]

To a solution of 4-chloro-2-(trifluoromethoxy)benzonitrile (1.0 g, 4.5 mmol) in THF (2.5 mL) was added TMPZnCl.LiCl (1.0 M, 4.4 mL, 4.4 mmol) and the mixture was stirred at 60° C. for 16 h. A solution of iodine (1.1 g, 4.5 mmol) in THF (2.5 mL) was added to the warm reaction mixture and stirring was maintained at 60° C. for 15 minutes. After cooling to rt, the reaction was quenched with saturated aqueous sodium thiosulfate and extracted with EtOAc (×3). The combined organic extracts were dried over Na$_2$SO$_4$, concentrated in vacuo. Purification (FCC, SiO$_2$, 0-5% EtOAc/hexanes) afforded the title compound as a white solid (980 mg, 62% yield). $^1$H NMR (500 MHz, DMSO-d$_6$) δ 8.11 (d, J=8.4 Hz, 1H), 7.89 (d, J=8.5 Hz, 1H).

Intermediate 7: 3,5-Dichloro-4-iodo-2-(trifluoromethyl)pyridine

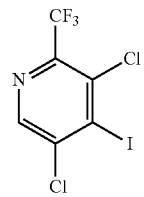 [SMILES: FC(F)(F)c1ncc(Cl)c(I)c1Cl]

The title compound was prepared in a manner analogous to Intermediate 6, substituting 3,5-dichloro-2-(trifluoromethyl)pyridine for 4-chloro-2-(trifluoromethoxy)benzonitrile and heating at 60° C. for 16 h instead of 15 minutes. $^1$H NMR (400 MHz, CDCl$_3$) δ 8.47 (s, 1H).

Intermediate 8: 3-Chloro-4-iodo-5-(trifluoromethoxy)pyridine

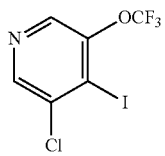

Step A: 3-Chloro-5-(methoxymethoxy)pyridine

To a cooled (0° C.) solution of 5-chloropyridin-3-ol (5 g, 38.6 mmol) in dry THF (50 mL) was added potassium tert-butoxide (21.6 g, 193 mmol), and the reaction mixture was then warmed to rt and stirred for 30 minutes. The reaction was again cooled to (0° C.) and chloromethyl methyl ether (7.4 mL, 96.5 mmol) was added dropwise. After the addition the mixture was stirred for another 3 h at rt. The reaction mixture was diluted with water and extracted with EtOAc. The organic extracts were washed with brine, dried over Na$_2$SO$_4$, and concentrated in vacuo to give the title compound as an oil, which was used without further purification (4.3 g, 65% yield). MS (ESI): mass calcd. for C$_7$H$_8$ClNO$_2$, 173.0; m/z found, 174.0 [M+H]$^+$.

Step B:
3-Chloro-4-iodo-5-(methoxymethoxy)pyridine

To a cooled (−78° C.) solution of 3-chloro-5-(methoxymethoxy)pyridine (3.4 g, 19.7 mmol) in THF (20 mL) was added n-butyllithium (2.5 M/hexanes, 13 mL, 142 mmol) dropwise over a period of 20 minutes. Stirring was maintained at −78° C. for 1 h, and then a solution of iodine (6.6 g, 26 mmol) in THF (20 mL) was added dropwise at −78° C. over a period of 30 minutes. After the addition, the resultant mixture was then allowed to warm to rt and stirred for another 30 minutes. The reaction mixture was poured into saturated aqueous Na$_2$SO$_3$ and extracted with EtOAc (2×200 mL). The combined organic extracts were dried over Na$_2$SO$_4$ and concentrated in vacuo to give the title compound as yellow solid (2.8 g, 47% yield). MS (ESI): mass calcd. for C$_7$H$_7$ClINO$_2$, 298.9; m/z found, 300.0 [M+H]$^+$. $^1$H NMR (400 MHz, DMSO-d$_6$) δ 8.28 (s, 1H), 8.18 (s, 1H), 5.40 (s, 2H), 3.44 (s, 3H).

Step C: 5-Chloro-4-iodopyridin-3-ol

3-Chloro-4-iodo-5-(methoxymethoxy)pyridine (2.8 g, 9.2 mmol) was added to 4N HCl/dioxane (15 mL) and the mixture was stirred at rt for 24 hours. The resulting yellow precipitate was filtered and washed with DCM to provide the title compound (2.2 g, 93% yield). MS (ESI): mass calcd. for C$_5$H$_3$ClINO, 254.9; m/z found, 255.9 [M+H]$^+$. $^1$H NMR (400 MHz, DMSO-d$_6$) δ 8.20 (s, 1H), 8.10 (s, 1H), 7.29 (s, 3H).

Step D:
3-(Bromodifluoromethoxy)-5-chloro-4-iodopyridine

To a cooled (0° C.) solution of 5-chloro-4-iodopyridin-3-ol (1.6 g, 6.3 mmol) in DMF (20 mL) was added sodium hydride (1.3 g, 31.3 mmol) portion wise. The mixture was then warmed to rt, stirred vigorously for 1 h. The reaction mixture was cooled to 0° C., then a solution of dibromodifluoromethane (4.6 mL, 50.1 mmol) in DMF (5.0 mL) was added, followed by portion wise addition of potassium tert-butoxide (2.1 g, 18.8 mmol). The mixture was heated to 80° C. for 24 h in a sealed vial. After cooling to rt, the crude reaction mixture was diluted with water, and extracted with EtOAc (×3). The combined organic extracts were dried over Na$_2$SO$_4$ and concentrated in vacuo. Purification (FCC, SiO$_2$; 0-50% EtOAc/hexanes) provided the title compound as white solid (350 mg, 15% yield). MS (ESI): mass calcd. for C$_5$H$_3$ClINO, 382.8; m/z found, 383.8 [M+H]$^+$. $^1$H NMR (400 MHz, DMSO-d$_6$) δ 8.68 (s, 1H), 8.48 (t, J=1.6 Hz, 1H).

Step E:
3-Chloro-4-iodo-5-(trifluoromethoxy)pyridine

To a cooled (−78° C.) solution of 3-(bromodifluoromethoxy)-5-chloro-4-iodopyridine (306 mg, 0.8 mmol) in DCM (20 mL) was added silver tetrafluoroborate (341 mg, 1.7 mmol) portion wise. The reaction mixture was then warmed to rt and stirred for 20 h. To the crude reaction mixture was added saturated sodium bicarbonate solution (5 mL) and the mixture was filtered. The filtrate was extracted with DCM (×2); the combined organic extracts were dried over Na$_2$SO$_4$ and concentrated in vacuo. Purification (FCC, SiO$_2$; 0-50% EtOAc/hexanes) provided the title compound as white solid (160 mg, 62% yield). $^1$H NMR (400 MHz, DMSO-d$_6$) δ 8.68 (s, 1H), 8.53 (q, J=1.4 Hz, 1H).

Intermediate 9:
3-Chloro-4-iodo-5-(difluoromethoxy)pyridine

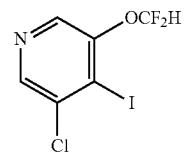

To a solution of 5-chloro-4-iodopyridin-3-ol (1 g, 3.9 mmol) in DMF (16 mL) was added a solution of sodium chlorodifluoroacetate (1.2 g, 7.8 mmol) in water (4 mL), followed by the addition of Cs$_2$CO$_3$ (3.8 g, 12.0 mmol). The reaction mixture was then heated to 100° C. for 24 h. After cooling to rt, the crude mixture was diluted with water and extracted with EtOAc, washed with brine and the combined organic extracts were dried over Na$_2$SO$_4$ and concentrated in vacuo. Purification (FCC, SiO$_2$; 0-50% EtOAc/hexanes) provided the title compound as white solid (326 mg, 27% yield). $^1$H NMR (400 MHz, DMSO-d$_6$) δ 8.53 (s, 1H), 8.31 (t, J=1.0 Hz, 1H), 7.40 (t, J=72.5 Hz, 1H).

Intermediate 10: 7-Chloro-5-(4,4,5,5-tetramethyl-1,3,2-dioxaborolan-2-yl)indolin-2-one

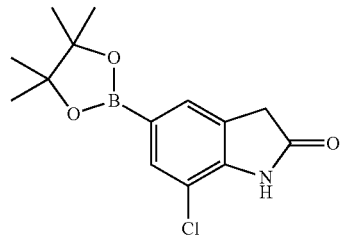 [SMILES: CC1(C)OB(c2cc(Cl)c3c(c2)CC(=O)N3)OC1(C)C]

Step A: 5-Bromo-7-chloroindolin-2-one

To a cooled (0° C.) solution of 7-chloroindolin-2-one (1 g, 6.0 mmol) in TFA (11 mL) was added N-bromosuccinimide (1 g, 6.0 mmol) portion wise and stirred the mixture at same temperature for 6 h. Concentrated TFA in vacuo with DCM (25 mL) and then with EtOAc. The crude product was triturated with ethanol to provide the title compound as a white solid (861 mg, 58% yield). MS (ESI): mass calcd. for C$_8$H$_5$BrClNO, 244.9; m/z found, 246.0 [M+H]$^+$. $^1$H NMR (500 MHz, DMSO-d$_6$) δ 10.92 (s, 1H), 7.52-7.48 (m, 1H), 7.38 (d, J=1.2 Hz, 1H), 3.62 (s, 2H).

Step B: 7-Chloro-5-(4,4,5,5-tetramethyl-1,3,2-dioxaborolan-2-yl)indolin-2-one

The title compound was prepared in a manner analogous to Intermediate 4, substituting 5-bromo-7-chloroindolin-2-one for 5-bromo-7-fluoroindolin-2-one. The crude product was triturated with DCM to provide the title compound as a white solid (84% yield). MS (ESI): mass calcd. for $C_{14}H_{17}BClNO_3$, 293.1; m/z found, 294.1 [M+H]$^+$. $^1$H NMR (400 MHz, DMSO-d$_6$) δ 10.94 (s, 1H), 7.43 (d, J=1.1 Hz, 1H), 7.41 (d, J=1.2 Hz, 1H), 3.60 (t, J=1.0 Hz, 2H), 1.28 (s, 12H).

Intermediate 11: 7-Ethyl-5-(4,4,5,5-tetramethyl-1,3,2-dioxaborolan-2-yl)indolin-2-one

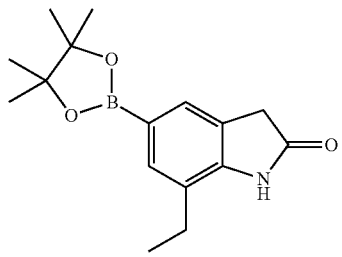 [SMILES: CCc1cc(B2OC(C)(C)C(C)(C)O2)cc2c1NC(=O)C2]

The title compound was prepared in a manner analogous to Intermediate 10, substituting 7-ethylindolin-2-one for 7-chlorooindolin-2-one in Step A. MS (ESI): mass calcd. for $C_{16}H_{22}BNO_3$, 287.2; m/z found, 288.1 [M+H]$^+$. $^1$H NMR (400 MHz, DMSO-d$_6$) δ 10.57 (s, 1H), 7.34 (d, J=1.1 Hz, 1H), 7.32 (d, J=1.3 Hz, 1H), 3.47 (s, 2H), 2.56 (q, J=7.5 Hz, 2H), 1.27 (s, 12H), 1.10 (t, J=7.5 Hz, 3H).

Intermediate 12: 2-Oxo-5-(4,4,5,5-tetramethyl-1,3,2-dioxaborolan-2-yl)indoline-7-carbonitrile

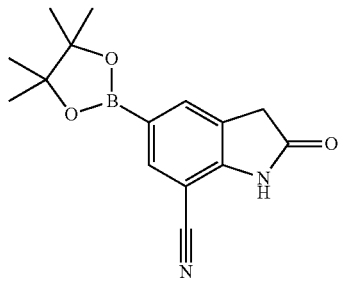 [SMILES: CC1(C)OB(c2cc(C#N)c3c(c2)CC(=O)N3)OC1(C)C]

The title compound was prepared in a manner analogous to Intermediate 10, substituting 5-bromo-2-oxoindoline-7-carbonitrile for 5-bromo-7-chloroindolin-2-one in Step A. Purification (FCC, SiO$_2$; 0-50% EtOAc/hexanes) afforded the title compound as white solid (203 mg, 62% yield). MS (ESI): mass calcd. for $C_{15}H_{17}BN_2O_3$, 284.1; m/z found, 285.1 [M+H]$^+$. $^1$H NMR (500 MHz, DMSO-d$_6$) δ 11.50 (s, 1H), 7.73-7.68 (m, 1H), 7.70-7.65 (m, 1H), 3.58 (s, 2H), 1.29 (s, 12H).

Intermediate 13: 5-(4,4,5,5-Tetramethyl-1,3,2-dioxaborolan-2-yl)-7-(trifluoromethyl)indolin-2-one

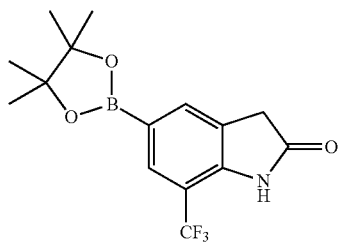 [SMILES: CC1(C)OB(c2cc3c(c(C(F)(F)F)c2)NC(=O)C3)OC1(C)C]

Step A:
5-Bromo-7-(trifluoromethyl)indoline-2,3-dione

To a suspension of 7-(trifluoromethyl)indoline-2,3-dione (0.5 g, 2.3 mmol) in AcOH (2.3 mL) was added bromine (0.14 mL, 2.79 mmol). The mixture was allowed to stir at rt and after 24 h an additional 100 μL of bromine was added. The reaction was stirred at rt for an additional 24 h, then poured into ice and stirred for 0.5 h. The resulting mixture was filtered and the solids were washed with H$_2$O to afford the title compound as an orange solid (585 mg, 85%). $^1$H NMR (400 MHz, DMSO-d$_6$) δ 11.58 (s, 1H), 8.07-7.99 (m, 1H), 7.99-7.91 (m, 1H).

Step B: 5-Bromo-7-(trifluoromethyl)indolin-2-one

To a solution of 5-bromo-7-(trifluoromethyl)indoline-2,3-dione (585 mg, 1.99 mmol) in n-butanol (20 mL) was added hydrazine hydrate (117 μL, 2.4 mmol). The mixture was heated at 80° C. for 0.5 h. The temperature was maintained at 80° C. and TEA (277 μL, 1.99 mmol) was added. The temperature was then increased to 100° C. and the reaction was stirred at reflux for 24 h. The reaction was cooled to rt and concentrated in vacuo. The crude residue was suspended in hexanes and the resulting mixture was filtered. The solids were washed with hexanes to afford the title compound (496 mg, 88%). $^1$H NMR (400 MHz, DMSO-d$_6$) δ 11.00 (s, 1H), 7.71-7.67 (m, 1H), 7.65-7.61 (m, 1H), 3.65-3.55 (m, 2H).

Step C: 5-(4,4,5,5-Tetramethyl-1,3,2-dioxaborolan-2-yl)-7-(trifluoromethyl)indolin-2-one To a solution of 5-bromo-7-(trifluoromethyl)indolin-2-one (100 mg, 0.36 mmol) in dioxane (1.2 mL) was added potassium acetate (70 mg, 0.71 mmol), bis(pinacolato)diboron (110 mg, 0.43 mmol) and PdCl$_2$(dppf)-CH$_2$Cl$_2$ (26 mg, 0.04 mmol). The solution was degassed with nitrogen and then heated at 85° C. for 3 h. After cooling to rt, the reaction mixture was diluted with brine and extracted with EtOAc (×2). The combined organic extracts were dried over MgSO$_4$, concentrated. Purification (FFC, SiO$_2$; 0-100% EtOAc/hexanes) afforded the desired product (72 mg, 62% yield). MS (ESI): mass calcd. for $C_{15}H_{17}BF_3NO_3$, 327.1; m/z found, 328.0 [M+H]$^+$. $^1$H NMR (400 MHz, DMSO-d$_6$) δ 11.16 (s, 1H), 7.69 (s, 1H), 7.66 (s, 1H), 3.59 (s, 2H), 1.29 (s, 12H).

Intermediate 14: 5-(4,4,5,5-Tetramethyl-1,3,2-dioxaborolan-2-yl)-7-(trifluoromethoxy)indolin-2-one

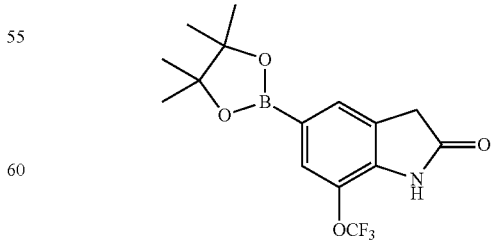

The title compound was prepared in a manner analogous to Intermediate 13, substituting 7-(trifluoromethoxy)indoline-2,3-dione for 7-(trifluoromethyl)indoline-2,3-dione in Step A. MS (ESI): mass calcd. for $C_{15}H_{17}BF_3NO_4$, 343.1;

m/z found, 344.0 [M+H]⁺. ¹H NMR (400 MHz, DMSO-d₆) δ 11.22 (s, 1H), 7.52-7.44 (m, 1H), 7.39-7.34 (m, 1H), 3.64-3.56 (m, 2H), 1.28 (s, 12H).

Intermediate 15: 7-Methoxy-5-(4,4,5,5-tetramethyl-1,3,2-dioxaborolan-2-yl)indolin-2-one

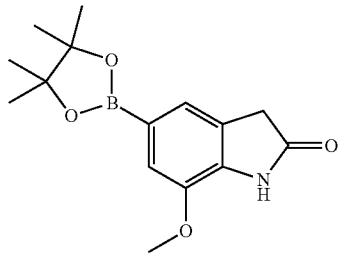 [SMILES: COc1cc(B2OC(C)(C)C(C)(C)O2)cc2c1NC(=O)C2]

The title compound was prepared in a manner analogous to Intermediate 13, substituting 7-methoxyindoline-2,3-dione for 7-(trifluoromethyl)indoline-2,3-dione in Step A. MS (ESI): mass calcd. for $C_{15}H_{20}BNO_4$, 289.2; m/z found, 290.1 [M+H]⁺. ¹H NMR (400 MHz, DMSO-d₆) δ 10.55 (s, 1H), 7.16 (d, J=1.1 Hz, 1H), 7.10 (s, 1H), 3.82 (s, 3H), 3.48 (s, 2H), 1.28 (s, 12H).

Example 1: 5-(2,6-Dimethylphenyl)indolin-2-one

A solution of (2,6-dimethylphenyl)boronic acid (71 mg, 0.47 mmol), 5-bromoindolin-2-one (50 mg, 0.24 mmol), potassium phosphate (150 mg, 0.71 mmol), dicyclohexyl(2',6'-dimethoxy-[1,1'-biphenyl]-2-yl)phosphine (9.7 mg, 0.024 mmol), and Pd₂(dba)₃ (5.4 mg, 0.006 mmol) in toluene (1.0 mL) was degassed with nitrogen for 10 minutes. The reaction mixture was heated at 100° C. for 16 h. After cooling to rt, the reaction was transferred directly to a silica gel column and purified by flash chromatography (0-30% EtOAc/hexanes) to provide the title compound as a white solid (56 mg, 61% yield). MS (ESI): mass calcd. for $C_{16}H_{15}NO$, 237.1; m/z found, 238.1 [M+H]⁺. ¹H NMR (500 MHz, CDCl₃) δ 9.02 (s, 1H), 7.19-7.06 (m, 3H), 7.06-6.90 (m, 3H), 3.60 (s, 2H), 2.04 (s, 6H).

Example 2: 5-(2-Bromo-6-chlorophenyl)indolin-2-one

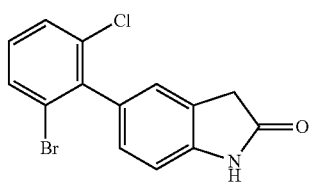 [SMILES: O=C1Cc2cc(-c3c(Cl)cccc3Br)ccc2N1]

A solution of 5-(4,4,5,5-tetramethyl-1,3,2-dioxaborolan-2-yl)indolin-2-one (250 mg, 0.96 mmol), 1-bromo-3-chloro-2-iodobenzene (373 mg, 1.2 mmol), and potassium phosphate (410 mg, 1.9 mmol) in 4:1 dioxane: water (3.0 mL) was degassed with nitrogen for 10 minutes. PdCl₂(dppf)-CH₂Cl₂ (35 mg, 0.05 mmol) was added at once and the resulting mixture was degassed with nitrogen for an additional 10 minutes. The reaction mixture was heated at 100° C. for 16 h. After cooling to rt, water was added and the aqueous layer was extracted with DCM (×3). The combined organic extracts were dried over Na₂SO₄ and concentrated in vacuo. Purification (FCC, SiO2; 0-50% EtOAc/hexanes) provided the title compound as a white solid (189 mg, 61% yield). MS (ESI): mass calcd. for $C_{14}H_9BrClNO$, 321.0; m/z found, 321.9 [M+H]⁺. ¹H NMR (500 MHz, DMSO-d₆) δ 10.50 (s, 1H), 7.72 (dd, J=8.1, 1.1 Hz, 1H), 7.60 (dd, J=8.1, 1.1 Hz, 1H), 7.32 (t, J=8.1 Hz, 1H), 7.11-6.97 (m, 2H), 6.91 (dd, J=8.0, 0.6 Hz, 1H), 3.53 (s, 2H).

Example 3: 5-(2-Chloro-6-methyl-phenyl)indolin-2-one

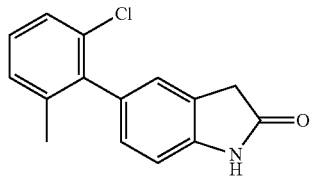 [SMILES: Cc1cccc(Cl)c1-c1ccc2c(c1)CC(=O)N2]

The title compound was prepared in a manner analogous to Example 2, substituting 1-chloro-2-iodo-3-methylbenzene for 1-bromo-3-chloro-2-iodobenzene. MS (ESI): mass calcd. for $C_{15}H_{12}ClNO$, 257.1; m/z found, 258.1 [M+H]⁺. ¹H NMR (400 MHz, CDCl₃) δ 8.95 (s, 1H), 7.36-7.28 (m, 1H), 7.23-7.14 (m, 2H), 7.10-7.02 (m, 2H), 6.98 (d, J=7.9 Hz, 1H), 3.62 (d, J=2.8 Hz, 2H), 2.10 (s, 3H).

Example 4: 5-(2,6-Dichlorophenyl)indolin-2-one

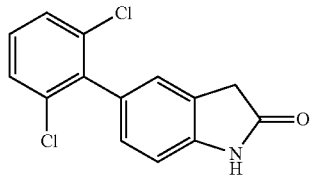

The title compound was prepared in a manner analogous to Example 2, substituting 1,3-dichloro-2-iodobenzene for 1-bromo-3-chloro-2-iodobenzene. MS (ESI): mass calcd. for $C_{14}H_9Cl_2NO$, 277.0; m/z found, 278.0 [M+H]⁺. ¹H NMR (400 MHz, CDCl₃) δ 9.57 (s, 1H), 7.39 (d, J=8.1 Hz, 2H), 7.21 (dd, J=8.6, 7.5 Hz, 1H), 7.16-7.07 (m, 2H), 7.02 (d, J=8.4 Hz, 1H), 3.61 (s, 2H).

Example 5: 5-[2-Chloro-6-(trifluoromethoxy)phenyl]indolin-2-one

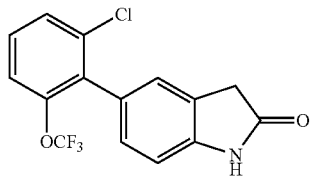

The title compound was prepared in a manner analogous to Example 2, substituting 1-chloro-2-iodo-3-(trifluoromethoxy)benzene (Intermediate 1) for 1-bromo-3-chloro-2-iodobenzene. MS (ESI): mass calcd. for $C_{15}H_9ClF_3NO_2$, 327.0; m/z found, 327.9 [M+H]$^+$. $^1$H NMR (400 MHz, DMSO-d$_6$) δ 10.52 (s, 1H), 7.65 (dd, J=7.9, 1.4 Hz, 1H), 7.57-7.44 (m, 2H), 7.16-7.02 (m, 2H), 6.92 (d, J=8.0 Hz, 1H), 3.54 (s, 2H).

Example 6: 2-[3-Chloro-2-(2-oxoindolin-5-yl)phenyl]acetonitrile

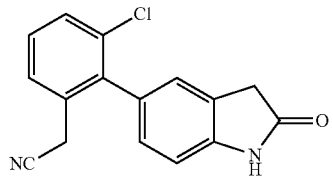 [SMILES: N#CCc1cccc(Cl)c1-c1ccc2c(c1)CC(=O)N2]

The title compound was prepared in a manner analogous to Example 2, substituting 2-(3-chloro-2-iodophenyl)acetonitrile (Intermediate 2) for 1-bromo-3-chloro-2-iodobenzene. MS (ESI): mass calcd. for $C_{16}H_{11}ClN_2O$, 282.1; m/z found, 283.1 [M+H]$^+$. $^1$H NMR (400 MHz, DMSO-d$_6$) δ 10.48 (s, 1H), 7.64-7.38 (m, 3H), 7.13-7.00 (m, 2H), 6.95-6.91 (m, 1H), 3.73-3.69 (d, J=5.4 Hz, 2H), 3.58-3.49 (d, J=15.9 Hz, 2H).

Example 7-Example 80 are prophetic compounds and may be made in a manner analogous to Example 2.

Example 7. 4-Chloro-3-(2-oxoindolin-5-yl)-2-(trifluoromethoxy)benzonitrile

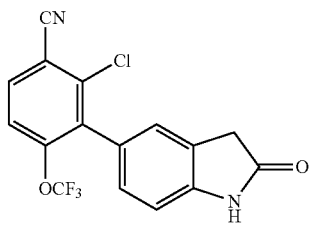 [SMILES: N#Cc1ccc(OC(F)(F)F)c(-c2ccc3c(c2)CC(=O)N3)c1Cl]

Predicted Chemical Formula: $C_{16}H_8ClF_3N_2O_2$, Exact mass: 352.02

Example 8.
5-(5-Chloro-2-methyl-phenyl)-indolin-2-one

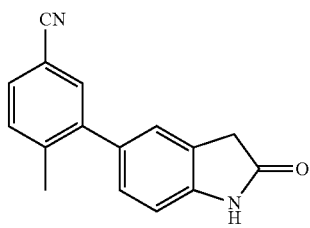 [SMILES: Cc1ccc(C#N)cc1-c1ccc2c(c1)CC(=O)N2]

Predicted Chemical Formula: $C_{15}H_{12}ClNO$, Exact mass: 257.06

Example 9. 5-[2-Chloro-6-(trifluoromethyl)phenyl]-indolin-2-one

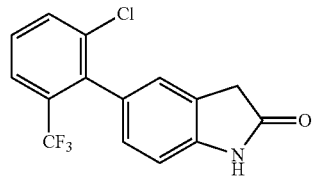

Predicted Chemical Formula: $C_{15}H_9ClF_3NO$, Exact mass: 311.03

Example 10:
5-(2-Isobutoxy-5-methyl-phenyl)-indolin-2-one

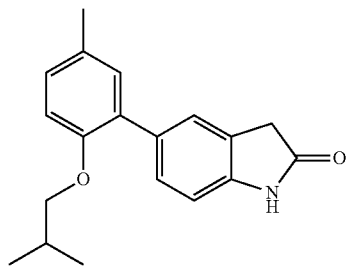 [SMILES: Cc1ccc(OCC(C)C)c(-c2ccc3c(c2)CC(=O)N3)c1]

Predicted Chemical Formula: $C_{19}H_{21}NO_2$, Exact mass: 295.16

Example 11:
5-(5-Chloro-2-isopropoxy-phenyl)-indolin-2-one

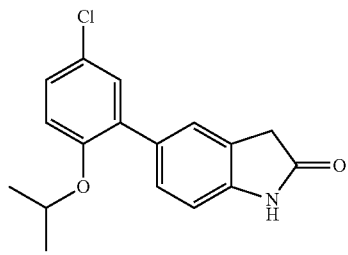 [SMILES: CC(C)Oc1ccc(Cl)cc1-c1ccc2c(c1)CC(=O)N2]

Predicted Chemical Formula: $C_{17}H_{16}ClNO_2$, Exact mass: 301.09

Example 12: 5-(2,5-Dichlorophenyl)-indolin-2-one

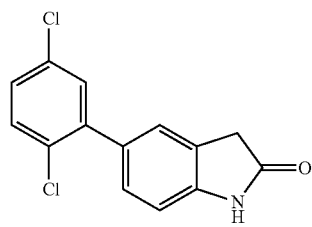 [SMILES: O=C1Cc2cc(-c3cc(Cl)ccc3Cl)ccc2N1]

Predicted Chemical Formula: $C_{14}H_9Cl_2NO$, Exact mass: 277.01

Example 13:
5-(2-Chloro-5-methyl-phenyl)-indolin-2-one

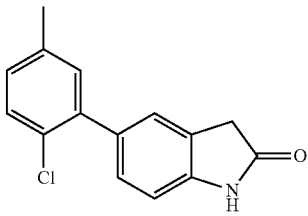 [SMILES: Cc1ccc(Cl)c(-c2ccc3c(c2)CC(=O)N3)c1]

Predicted Chemical Formula: $C_{15}H_{12}ClNO$, Exact mass: 257.06

Example 14: 5-[2-Isopropoxy-5-(trifluoromethyl)phenyl]-indolin-2-one

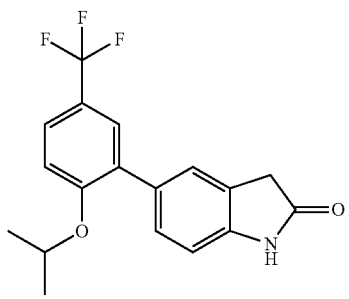 [SMILES: CC(C)Oc1ccc(C(F)(F)F)cc1-c1ccc2c(c1)CC(=O)N2]

Predicted Chemical Formula: $C_{18}H_{16}F_3NO_2$, Exact mass: 335.11

Example 15:
5-(2,6-Dichloro-3-methyl-phenyl)-indolin-2-one

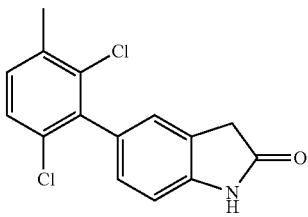 [SMILES: Cc1ccc(Cl)c(-c2ccc3c(c2)CC(=O)N3)c1Cl]

Predicted Chemical Formula: $C_{15}H_{11}Cl_2NO$, Exact mass: 291.02

Example 16: 5-[2-Chloro-5-(trifluoromethyl)phenyl]-indolin-2-one

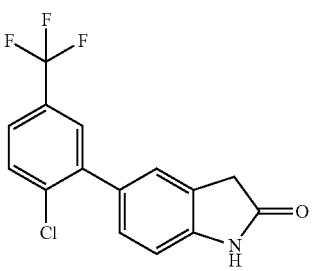 [SMILES: O=C1Cc2cc(-c3cc(C(F)(F)F)ccc3Cl)ccc2N1]

Predicted Chemical Formula: $C_{15}H_9ClF_3NO$, Exact mass: 311.03

Example 17:
5-(2-Benzyloxy-6-fluoro-phenyl)-indolin-2-one

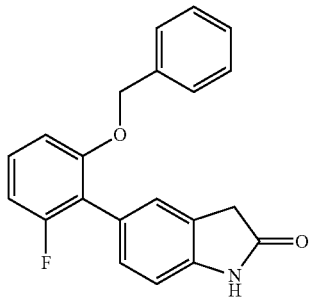 [SMILES: O=C1Cc2cc(-c3c(F)cccc3OCc3ccccc3)ccc2N1]

Predicted Chemical Formula: $C_{21}H_{16}FNO_2$, Exact mass: 333.12

Example 18: 5-[3-Chloro-2-(trifluoromethoxy)phenyl]-indolin-2-one

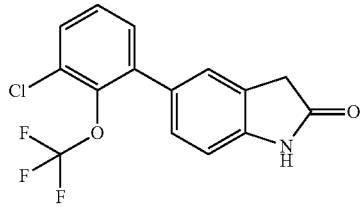 [SMILES: O=C1Cc2cc(-c3cccc(Cl)c3OC(F)(F)F)ccc2N1]

Predicted Chemical Formula: $C_{15}H_9ClF_3NO_2$, Exact mass: 327.03

Example 19: 5-[3-Chloro-2-(trifluoromethyl)phenyl]-indolin-2-one

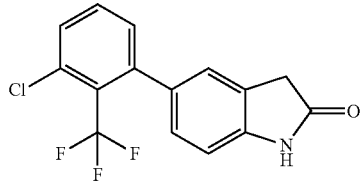 [SMILES: O=C1Cc2cc(-c3cccc(Cl)c3C(F)(F)F)ccc2N1]

Predicted Chemical Formula: $C_{15}H_9ClF_3NO$, Exact mass: 311.03

Example 20:
5-(2-Chloro-6-methyl-phenyl)-indolin-2-one

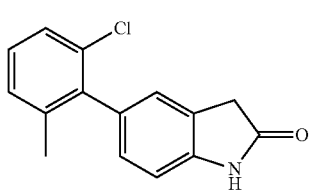 [SMILES: Cc1cccc(Cl)c1-c1ccc2c(c1)CC(=O)N2]

Predicted Chemical Formula: C$_{15}$H$_{12}$ClNO, Exact mass: 257.06

Example 21:
3-Methyl-2-(2-oxoindolin-5-yl)benzonitrile

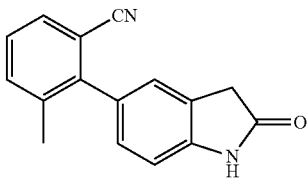 [SMILES: Cc1cccc(C#N)c1-c1ccc2c(c1)CC(=O)N2]

Predicted Chemical Formula: C$_{16}$H$_{12}$N$_2$O, Exact mass: 248.09

Example 22:
4-Methyl-3-(2-oxoindolin-5-yl)benzonitrile

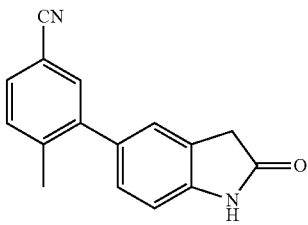 [SMILES: Cc1ccc(C#N)cc1-c1ccc2c(c1)CC(=O)N2]

Predicted Chemical Formula: C$_{16}$H$_{12}$N$_2$O, Exact mass: 248.09

Example 23:
4-Chloro-3-(2-oxoindolin-5-yl)benzonitrile

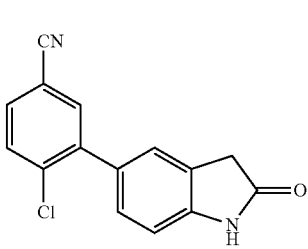 [SMILES: N#Cc1ccc(Cl)c(-c2ccc3c(c2)CC(=O)N3)c1]

Predicted Chemical Formula: C$_{15}$H$_9$ClN$_2$O, Exact mass: 268.04

Example 24: Methyl 3-chloro-2-(2-oxoindolin-5-yl)benzoate

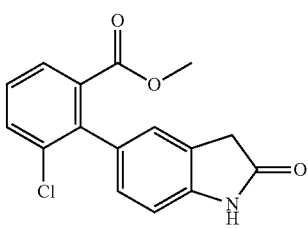 [SMILES: COC(=O)c1cccc(Cl)c1-c1ccc2c(c1)CC(=O)N2]

Predicted Chemical Formula: C$_{16}$H$_{12}$ClNO$_3$, Exact mass: 301.05

Example 25: Methyl 2-chloro-3-(2-oxoindolin-5-yl)benzoate

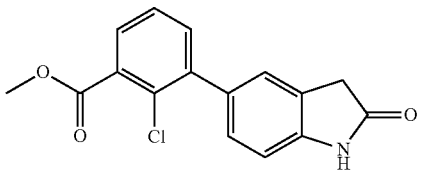 [SMILES: COC(=O)c1cccc(-c2ccc3c(c2)CC(=O)N3)c1Cl]

Predicted Chemical Formula: C$_{16}$H$_{12}$ClNO$_3$, Exact mass: 301.05

Example 26: Methyl 4-chloro-3-(2-oxoindolin-5-yl)benzoate

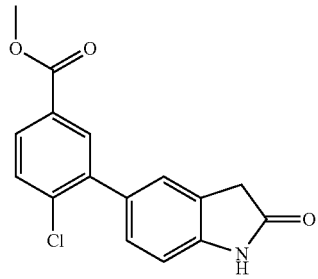 [SMILES: COC(=O)c1ccc(Cl)c(-c2ccc3c(c2)CC(=O)N3)c1]

Predicted Chemical Formula: C$_{16}$H$_{12}$ClNO$_3$, Exact mass: 301.05

Example 27: Methyl 3-methyl-2-(2-oxoindolin-5-yl)benzoate

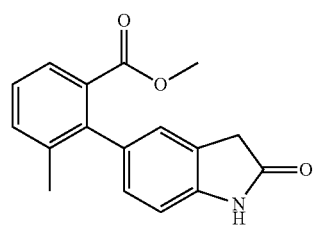 [SMILES: COC(=O)c1cccc(C)c1-c1ccc2c(c1)CC(=O)N2]

Predicted Chemical Formula: C$_{17}$H$_{15}$NO$_3$, Exact mass: 281.11

Example 28: Methyl 2-methyl-3-(2-oxoindolin-5-yl)benzoate

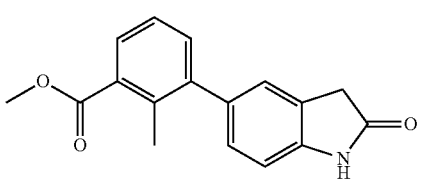 [SMILES: COC(=O)c1cccc(-c2ccc3c(c2)CC(=O)N3)c1C]

Predicted Chemical Formula: $C_{17}H_{15}NO_3$, Exact mass: 281.11

Example 29: Methyl 4-methyl-3-(2-oxoindolin-5-yl)benzoate

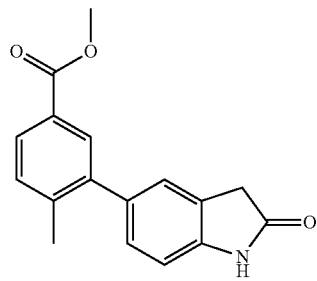 [SMILES: COC(=O)c1ccc(C)c(-c2ccc3c(c2)CC(=O)N3)c1]

Predicted Chemical Formula: $C_{17}H_{15}NO_3$, Exact mass: 281.11

Example 30: Methyl 2-methoxy-3-(2-oxoindolin-5-yl)benzoate

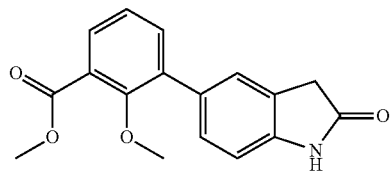 [SMILES: COC(=O)c1cccc(-c2ccc3c(c2)CC(=O)N3)c1OC]

Predicted Chemical Formula: $C_{17}H_{15}NO_4$, Exact mass: 297.10

Example 31: 5-(2,6-Difluorophenyl)-indolin-2-one

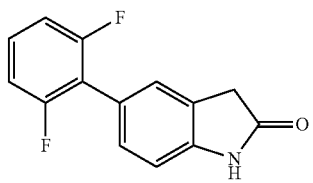 [SMILES: O=C1Cc2cc(-c3c(F)cccc3F)ccc2N1]

Predicted Chemical Formula: $C_{14}H_9F_2NO$, Exact mass: 245.07

Example 32: 5-(2-Chloro-6-fluoro-phenyl)-indolin-2-one

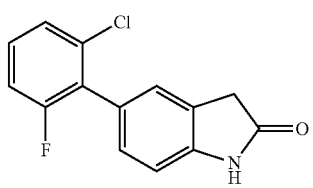

Predicted Chemical Formula: $C_{14}H_9ClFNO$, Exact mass: 261.04

Example 33: 5-(2-Fluoro-6-methyl-phenyl)-indolin-2-one

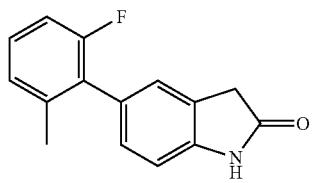 [SMILES: Cc1cccc(F)c1-c1ccc2c(c1)CC(=O)N2]

Predicted Chemical Formula: $C_{15}H_{12}FNO$, Exact mass: 241.09

Example 34: 5-(2-Fluoro-6-methoxy-phenyl)-indolin-2-one

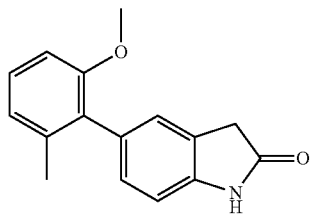 [SMILES: COc1cccc(C)c1-c1ccc2c(c1)CC(=O)N2]

Predicted Chemical Formula: $C_{16}H_{15}NO_2$, Exact mass: 253.11

Example 35: 3-Chloro-2-(2-oxoindolin-5-yl)benzonitrile

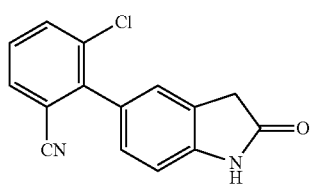 [SMILES: N#Cc1cccc(Cl)c1-c1ccc2c(c1)CC(=O)N2]

Predicted Chemical Formula: $C_{15}H_9ClN_2O$, Exact mass: 268.04

Example 36: 5-[2-Methyl-6-(trifluoromethyl)phenyl]-indolin-2-one

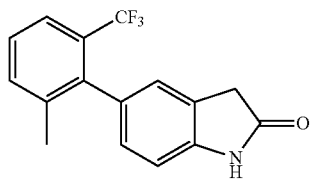

Predicted Chemical Formula: $C_{16}H_{12}F_3NO$, Exact mass: 291.09

Example 37: 5-(8-Quinolyl)-indolin-2-one

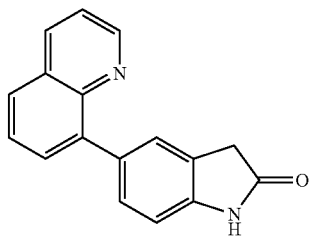 [SMILES: O=C1Cc2cc(-c3cccc4cccnc34)ccc2N1]

Predicted Chemical Formula: $C_{17}H_{12}N_2O$, Exact mass: 260.09

Example 38: 5-[2-Methyl-3-(trifluoromethyl)phenyl]-indolin-2-one

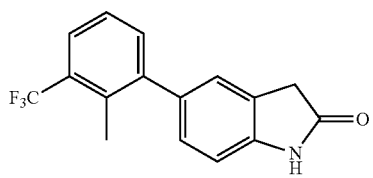

Predicted Chemical Formula: $C_{16}H_{12}F_3NO$, Exact mass: 291.09

Example 39: 5-[2-Chloro-3-(trifluoromethyl)phenyl]-indolin-2-one

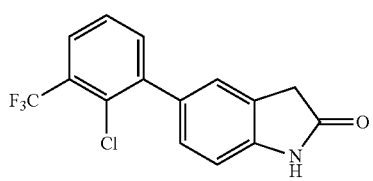

Predicted Chemical Formula: $C_{15}H_9ClF_3NO$, Exact mass: 311.03

Example 40: 2-Isopropoxy-6-(2-oxoindolin-5-yl)benzonitrile

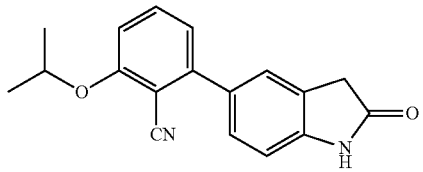 [SMILES: CC(C)Oc1cccc(-c2ccc3c(c2)CC(=O)N3)c1C#N]

Predicted Chemical Formula: $C_{18}H_{16}N_2O_2$, Exact mass: 292.12

Example 41: 2-Bromo-6-(2-oxoindolin-5-yl)benzonitrile

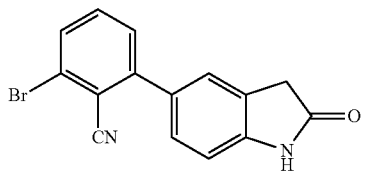 [SMILES: N#Cc1c(Br)cccc1-c1ccc2c(c1)CC(=O)N2]

Predicted Chemical Formula: $C_{15}H_9BrN_2O$, Exact mass: 311.99

Example 42: 5-(2-Chloro-3-methyl-phenyl)-indolin-2-one

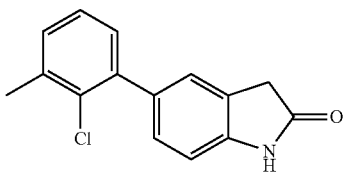 [SMILES: Cc1cccc(-c2ccc3c(c2)CC(=O)N3)c1Cl]

Predicted Chemical Formula: $C_{15}H_{12}ClNO$, Exact mass: 257.06

Example 43: 2-(2-Oxoindolin-5-yl)-6-(trifluoromethyl)benzonitrile

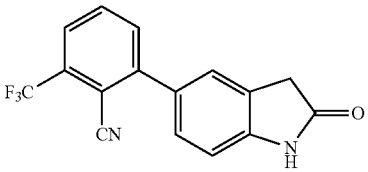 [SMILES: N#Cc1c(-c2ccc3c(c2)CC(=O)N3)cccc1C(F)(F)F]

Predicted Chemical Formula: $C_{16}H_9F_3N_2O$, Exact mass: 302.07

Example 44: 5-(2,3,6-Trichlorophenyl)-indolin-2-one

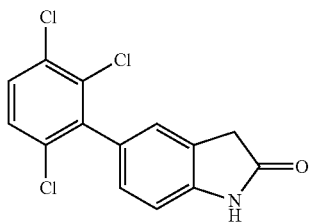 [SMILES: O=C1Cc2cc(-c3c(Cl)ccc(Cl)c3Cl)ccc2N1]

Predicted Chemical Formula: $C_{14}H_8Cl_3NO$, Exact mass: 310.97

Example 45:
2-Methyl-3-(2-oxoindolin-5-yl)benzonitrile

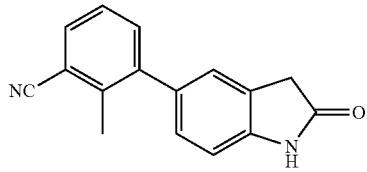 [SMILES: Cc1c(C#N)cccc1-c1ccc2c(c1)CC(=O)N2]

Predicted Chemical Formula: $C_{16}H_{12}N_2O$, Exact mass: 248.09

Example 46:
2-Chloro-3-(2-oxoindolin-5-yl)benzonitrile

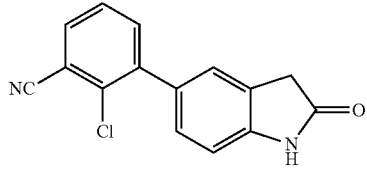 [SMILES: N#Cc1cccc(-c2ccc3c(c2)CC(=O)N3)c1Cl]

Predicted Chemical Formula: $C_{15}H_9ClN_2O$, Exact mass: 268.04

Example 47:
5-(3,5-Dichloro-4-pyridyl)-indolin-2-one

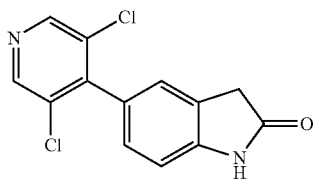 [SMILES: O=C1Cc2cc(-c3c(Cl)cncc3Cl)ccc2N1]

Predicted Chemical Formula: $C_{13}H_8Cl_2N_2O$, Exact mass: 278.00

Example 48: 5-(2-Chloro-4-methyl-3-pyridyl)-indolin-2-one

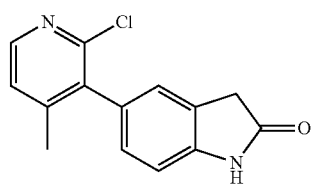

Predicted Chemical Formula: $C_{14}H_{11}ClN_2O$, Exact mass: 258.06

Example 49: N-Methyl-2-[2-(2-oxoindolin-5-yl)-6-(trifluoromethyl)phenyl]acetamide

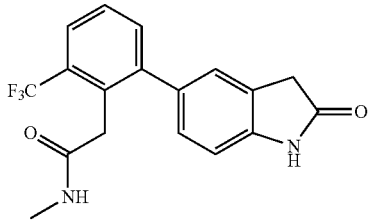 [SMILES: CNC(=O)Cc1c(-c2ccc3c(c2)CC(=O)N3)cccc1C(F)(F)F]

Predicted Chemical Formula: $C_{18}H_{15}F_3N_2O_2$, Exact mass: 348.11

Example 50: 5-[2-Chloro-6-(2-furylmethylamino)phenyl]-indolin-2-one

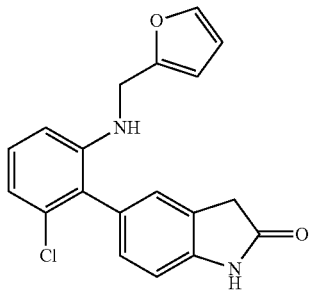 [SMILES: O=C1Cc2cc(-c3c(Cl)cccc3NCc3ccco3)ccc2N1]

Predicted Chemical Formula: $C_{19}H_{15}ClN_2O_2$, Exact mass: 338.08

Example 51: 5-[2-Chloro-6-(3-furylmethylamino)phenyl]-indolin-2-one

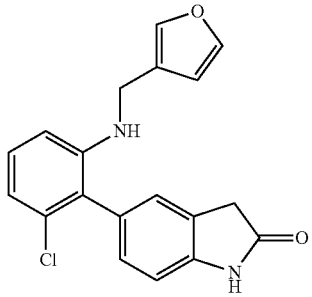 [SMILES: O=C1Cc2cc(-c3c(Cl)cccc3NCc3ccoc3)ccc2N1]

Predicted Chemical Formula: $C_{19}H_{15}ClN_2O_2$, Exact mass: 338.08

Example 52: 5-[2-Isopropoxy-6-(trifluoromethoxy)phenyl]-indolin-2-one

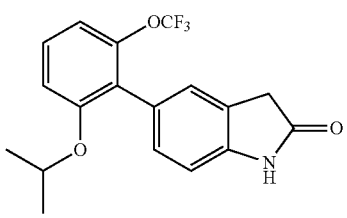 [SMILES: CC(C)Oc1cccc(OC(F)(F)F)c1-c1ccc2c(c1)CC(=O)N2]

Predicted Chemical Formula: $C_{18}H_{16}F_3NO_3$, Exact mass: 351.11

Example 53: 5-[2-(Cyclopropylmethoxy)-6-(trifluoromethoxy)phenyl]-indolin-2-one

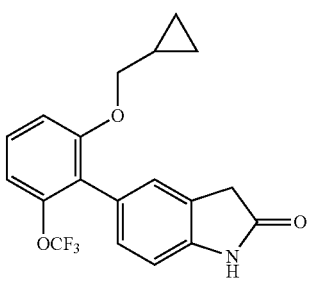 [SMILES: O=C1Cc2cc(-c3c(OCC4CC4)cccc3OC(F)(F)F)ccc2N1]

Predicted Chemical Formula: $C_{19}H_{16}F_3NO_3$, Exact mass: 363.11

Example 54: 5-[2-Chloro-6-(cyclopropoxy)phenyl]-indolin-2-one

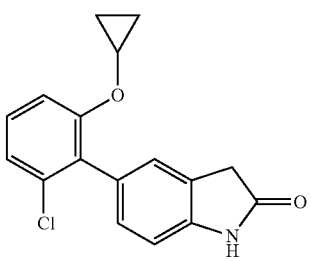 [SMILES: O=C1Cc2cc(-c3c(Cl)cccc3OC3CC3)ccc2N1]

Predicted Chemical Formula: $C_{17}H_{14}ClNO_2$, Exact mass: 299.07

Example 55: 5-[2-Chloro-6-(cyclopropylmethoxy)phenyl]-indolin-2-one

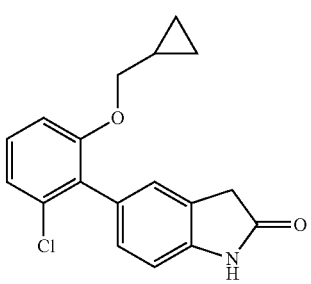 [SMILES: O=C1Cc2cc(-c3c(Cl)cccc3OCC3CC3)ccc2N1]

Predicted Chemical Formula: $C_{18}H_{16}ClNO_2$, Exact mass: 313.09

Example 56: (±)-5-[2-Chloro-6-[(2,2-difluorocyclopropyl)methoxy]phenyl]-indolin-2-one

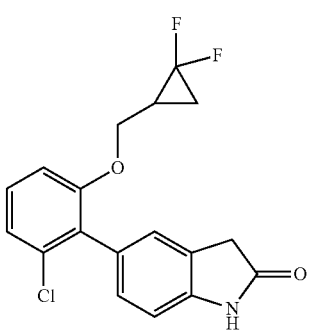 [SMILES: O=C1Cc2cc(-c3c(Cl)cccc3OCC3CC3(F)F)ccc2N1]

Predicted Chemical Formula: $C_{18}H_{14}ClF_2NO_2$, Exact mass: 349.07

Example 57: 5-[2-Chloro-6-(difluoromethoxy)phenyl]-indolin-2-one

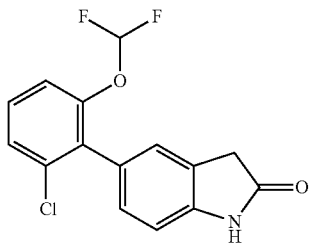 [SMILES: O=C1Cc2cc(-c3c(Cl)cccc3OC(F)F)ccc2N1]

Predicted Chemical Formula: $C_{15}H_{10}ClF_2NO_2$, Exact mass: 309.04

Example 58: 5-[2-Chloro-6-(2,2,2-trifluoroethoxy)phenyl]-indolin-2-one

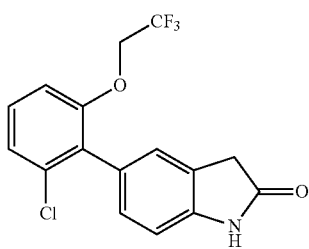 [SMILES: O=C1Cc2cc(-c3c(Cl)cccc3OCC(F)(F)F)ccc2N1]

Predicted Chemical Formula: $C_{16}H_{11}ClF_3NO_2$, Exact mass: 341.04

Example 59: 5-[2-Chloro-6-(2,2-difluoroethoxy)phenyl]-indolin-2-one

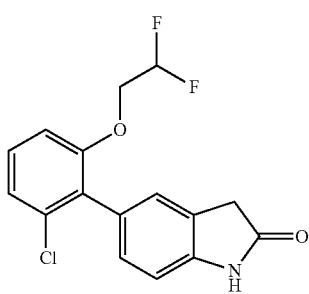 [SMILES: O=C1Cc2cc(-c3c(Cl)cccc3OCC(F)F)ccc2N1]

Predicted Chemical Formula: $C_{16}H_{12}ClF_2NO_2$, Exact mass: 323.05

Example 60: 2-[3-Chloro-2-(2-oxoindolin-5-yl)phenoxy]acetonitrile

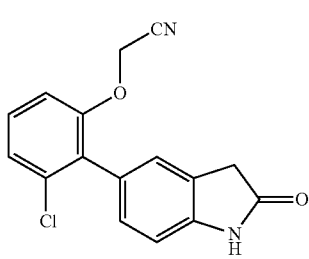 [SMILES: N#CCOc1cccc(Cl)c1-c1ccc2c(c1)CC(=O)N2]

Predicted Chemical Formula: C₁₆H₁₁ClN₂O₂, Exact mass: 298.05

Example 61:
5-(2-Benzyloxy-6-chloro-phenyl)-indolin-2-one

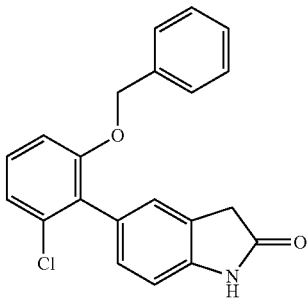 [SMILES: O=C1Cc2cc(-c3c(Cl)cccc3OCc3ccccc3)ccc2N1]

Predicted Chemical Formula: C₂₁H₁₆ClNO₂, Exact mass: 349.09

Example 62: tert-Butyl 3-[3-chloro-2-(2-oxoindolin-5-yl)phenoxy]azetidine-1-carboxylate

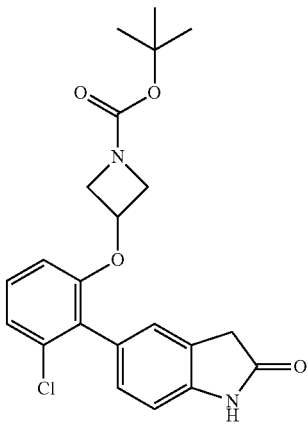 [SMILES: CC(C)(C)OC(=O)N1CC(Oc2cccc(Cl)c2-c2ccc3c(c2)CC(=O)N3)C1]

Predicted Chemical Formula: C₂₂H₂₃ClN₂O₄, Exact mass: 414.13

Example 63: 5-(2-Chloro-6-thiazol-5-yloxy-phenyl)-indolin-2-one

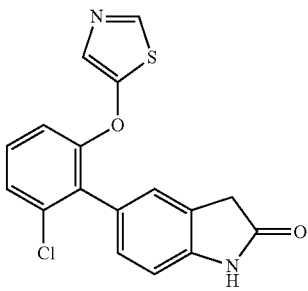 [SMILES: O=C1Cc2cc(-c3c(Cl)cccc3Oc3cncs3)ccc2N1]

Predicted Chemical Formula: C₁₇H₁₁ClN₂O₂S, Exact mass: 342.02

Example 64: 5-[2-(2,2-Difluoroethoxy)-6-methoxy-phenyl]-indolin-2-one

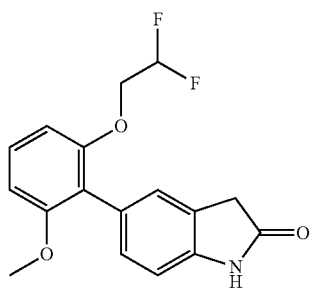 [SMILES: COc1cccc(OCC(F)F)c1-c1ccc2c(c1)CC(=O)N2]

Predicted Chemical Formula: C₁₇H₁₅F₂NO₃, Exact mass: 319.10

Example 65: 5-[2-Methoxy-6-(2,2,2-trifluoroethoxy)phenyl]-indolin-2-one

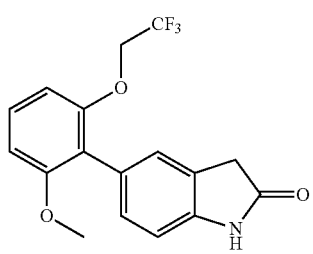 [SMILES: COc1cccc(OCC(F)(F)F)c1-c1ccc2c(c1)CC(=O)N2]

Predicted Chemical Formula: C₁₇H₁₄F₃NO₃, Exact mass: 337.09

Example 66:
5-(2-Benzyloxy-6-methoxy-phenyl)-indolin-2-one

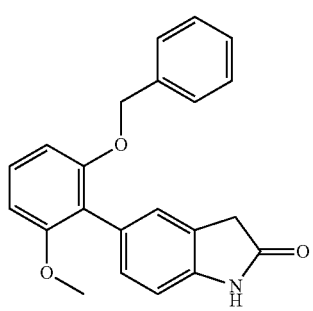 [SMILES: COc1cccc(OCc2ccccc2)c1-c1ccc2c(c1)CC(=O)N2]

Predicted Chemical Formula: C₂₂H₁₉NO₃, Exact mass: 345.14

Example 67: 5-[2-[(4-Fluorophenyl) ethoxy]-6-methoxy-phenyl]-indolin-2-one

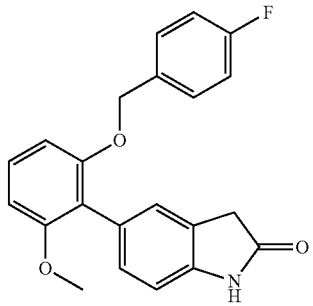 [SMILES: COc1cccc(OCc2ccc(F)cc2)c1-c1ccc2c(c1)CC(=O)N2]

Predicted Chemical Formula: $C_{22}H_{18}FNO_3$, Exact mass: 363.13

Example 68: 5-[2-Isopropoxy-6-(trifluoromethyl)phenyl]-indolin-2-one

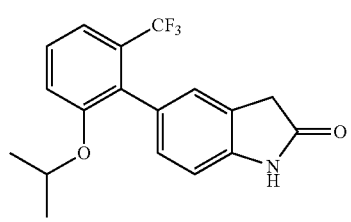 [SMILES: CC(C)Oc1cccc(C(F)(F)F)c1-c1ccc2c(c1)CC(=O)N2]

Predicted Chemical Formula: $C_{18}H_{16}F_3NO_2$, Exact mass: 335.11

Example 69: 5-[2-Chloro-3-(cyclopropoxy)phenyl]-indolin-2-one

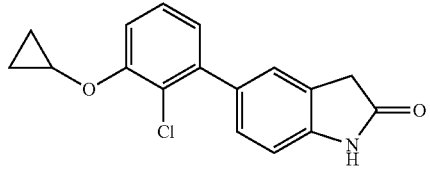 [SMILES: O=C1Cc2cc(-c3cccc(OC4CC4)c3Cl)ccc2N1]

Predicted Chemical Formula: $C_{17}H_{14}ClNO_2$, Exact mass: 299.07

Example 70: 5-(2-Chloro-3-isopropoxy-phenyl)-indolin-2-one

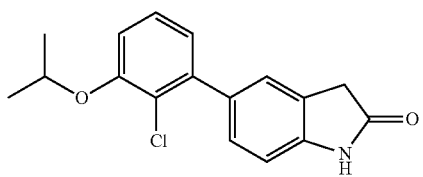 [SMILES: CC(C)Oc1cccc(-c2ccc3c(c2)CC(=O)N3)c1Cl]

Predicted Chemical Formula: $C_{17}H_{16}ClNO_2$, Exact mass: 301.09

Example 71: (±)-5-[2-Chloro-3-[(2,2-difluorocyclopropyl)methoxy]phenyl]-indolin-2-one

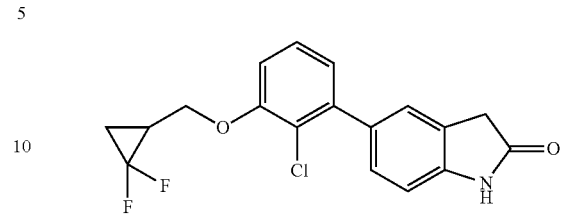

Predicted Chemical Formula: $C_{18}H_{14}ClF_2NO_2$, Exact mass: 349.07

Example 72: 5-[2-Chloro-3-(2,2-difluoroethoxy)phenyl]-indolin-2-one

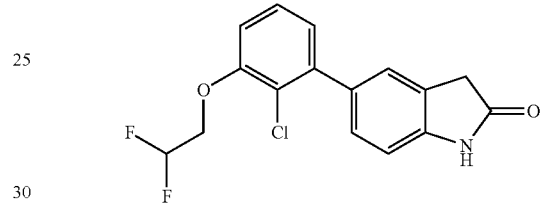

Predicted Chemical Formula: $C_{16}H_{12}ClF_2NO_2$, Exact mass: 323.05

Example 73: 5-[2-Chloro-3-(difluoromethoxy)phenyl]-indolin-2-one

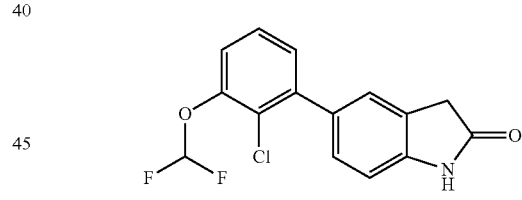

Predicted Chemical Formula: $C_{15}H_{10}ClF_2NO_2$, Exact mass: 309.04

Example 74: tert-Butyl 3-[2-chloro-3-(2-oxoindolin-5-yl)phenoxy]azetidine-1-carboxylate

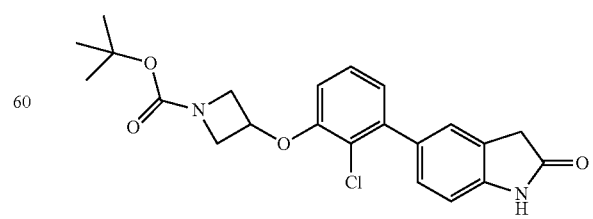

Predicted Chemical Formula: $C_{22}H_{23}ClN_2O_4$, Exact mass: 414.13

Example 75: 5-(3-Chloro-2-isopropoxy-phenyl)-indolin-2-one

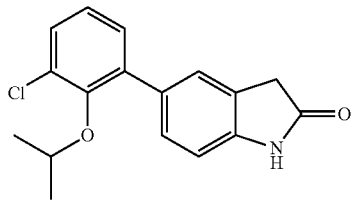 [SMILES: CC(C)Oc1c(Cl)cccc1-c1ccc2c(c1)CC(=O)N2]

Predicted Chemical Formula: $C_{17}H_{16}ClNO_2$, Exact mass: 301.09

Example 76: (±)-5-[2-Chloro-6-(2,2,2-trifluoro-1-methyl-ethoxy)phenyl]-indolin-2-one

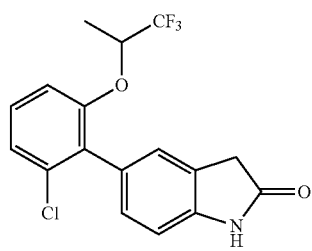 [SMILES: CC(Oc1cccc(Cl)c1-c1ccc2c(c1)CC(=O)N2)C(F)(F)F]

Predicted Chemical Formula: $C_{17}H_{13}ClF_3NO_2$, Exact mass: 355.06

Example 77: (±)-5-[2-Methoxy-6-(2,2,2-trifluoro-1-methyl-ethoxy)phenyl]-indolin-2-one

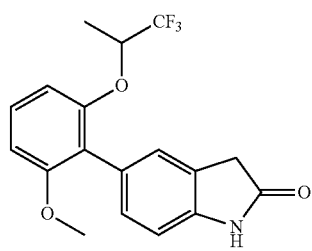 [SMILES: COc1cccc(OC(C)C(F)(F)F)c1-c1ccc2c(c1)CC(=O)N2]

Predicted Chemical Formula: $C_{18}H_{16}F_3NO_3$, Exact mass: 351.11

Example 78: 2-[3,4-Dichloro-2-(2-oxoindolin-5-yl)phenyl]acetonitrile

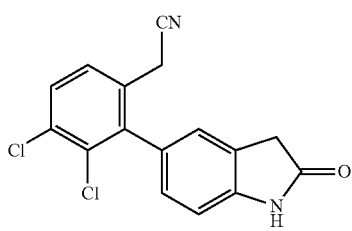 [SMILES: N#CCc1ccc(Cl)c(Cl)c1-c1ccc2c(c1)CC(=O)N2]

Predicted Chemical Formula: $C_{16}H_{10}Cl_2N_2O$, Exact mass: 316.02

Example 79: 2-[2-(2-Oxoindolin-5-yl)-3-trifluoromethoxy)phenyl]acetonitrile

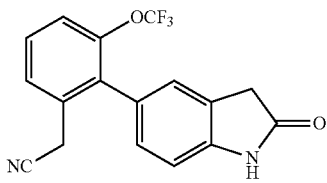 [SMILES: N#CCc1cccc(OC(F)(F)F)c1-c1ccc2c(c1)CC(=O)N2]

Predicted Chemical Formula: $C_{17}H_{11}F_3N_2O_2$, Exact mass: 332.08

Example 80: (±)-2-[3-Chloro-2-(2-oxoindolin-5-yl)phenyl]propanenitrile

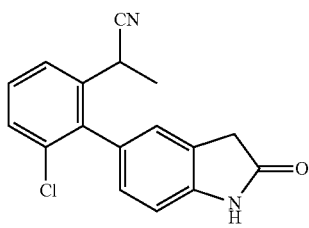 [SMILES: CC(C#N)c1cccc(Cl)c1-c1ccc2c(c1)CC(=O)N2]

Predicted Chemical Formula: $C_{17}H_{13}ClN_2O$, Exact mass: 296.07

Example 81: 2-[3-Chloro-2-(2-oxoindolin-5-yl)phenyl]-2-methyl-propanenitrile

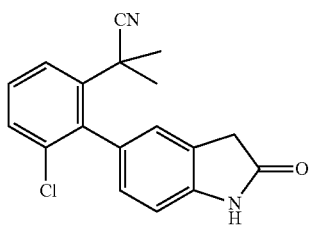 [SMILES: CC(C)(C#N)c1cccc(Cl)c1-c1ccc2c(c1)CC(=O)N2]

Step A:
2-(3-Chloro-2-iodophenyl)-2-methylpropanenitrile

To an ice cold solution of 60 wt % sodium hydride/mineral oil (180 mg, 4.5 mmol) in DMF (5.0 mL) was added 2-(3-chloro-2-iodophenyl) acetonitrile (250 mg, 0.90 mmol) in THF (2.5 mL) dropwise. The reaction mixture was stirred for 20 minutes at 0° C., and then iodomethane (0.06 mL, 0.90 mmol) was added. After stirring at rt for 16 h, the reaction mixture was quenched with water (1.0 mL), and the solvents were removed in vacuo. The crude residue was partitioned between EtOAc and 1N HCl. The organic layer was dried over $Na_2SO_4$ and concentrated to obtain the product as an oil (370 mg, 90% yield), which was used directly in the next reaction.

Step B: 2-(3-Chloro-2-(2-oxoindolin-5-yl)phenyl)-2-methylpropanenitrile

The title compound was prepared in a manner analogous to Example 2, substituting 2-(3-chloro-2-iodophenyl)-2-methylpropanenitrile for 1-bromo-3-chloro-2-iodobenzene. MS (ESI): mass calcd. for $C_{18}H_{15}ClFN_2O$, 310.1; m/z found, 311.7 [M+H]⁺. ¹H NMR (400 MHz, DMSO-d₆) δ

10.50 (s, 1H), 7.64-7.53 (m, 2H), 7.50-7.40 (m, 1H), 7.08-6.97 (m, 2H), 6.87 (d, J=7.9 Hz, 1H), 3.59-3.41 (m, 2H), 1.57 (s, 6H).

Example 82-Example 114, Example 116, and Example 120 are prophetic compounds and may be prepared in a manner analogous to Example 1.

Example 82: 1-[3-Chloro-2-(2-oxoindolin-5-yl)phenyl]cyclopropanecarbonitrile

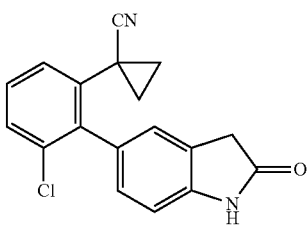 [SMILES: N#CC1(c2cccc(Cl)c2-c2ccc3c(c2)CC(=O)N3)CC1]

Predicted Chemical Formula: $C_{18}H_{13}ClN_2O$, Exact mass: 308.07

Example 83: 1-[3-Chloro-2-(2-oxoindolin-5-yl)phenyl]cyclobutanecarbonitrile

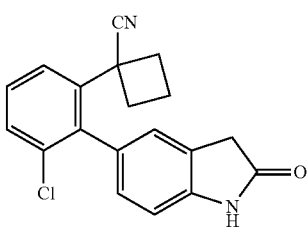 [SMILES: N#CC1(c2cccc(Cl)c2-c2ccc3c(c2)CC(=O)N3)CCC1]

Predicted Chemical Formula: $C_{19}H_{15}ClN_2O$, Exact mass: 322.09

Example 84: 2-[2-Chloro-3-(2-oxoindolin-5-yl)phenyl]acetonitrile

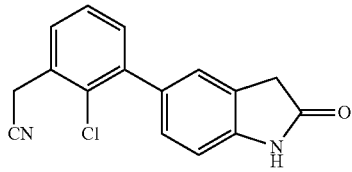 [SMILES: N#CCc1cccc(-c2ccc3c(c2)CC(=O)N3)c1Cl]

Predicted Chemical Formula: $C_{16}H_{11}ClN_2O$, Exact mass: 282.06

Example 85: 2-[2,4-Dichloro-3-(2-oxoindolin-5-yl)phenyl]acetonitrile

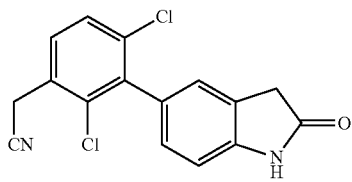 [SMILES: N#CCc1ccc(Cl)c(-c2ccc3c(c2)CC(=O)N3)c1Cl]

Predicted Chemical Formula: $C_{16}H_{10}Cl_2N_2O$, Exact mass: 316.02

Example 86: 2-[3-Bromo-2-(2-oxoindolin-5-yl)phenyl]acetonitrile

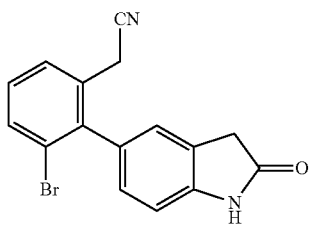 [SMILES: N#CCc1cccc(Br)c1-c1ccc2c(c1)CC(=O)N2]

Predicted Chemical Formula: $C_{16}H_{11}BrN_2O$, Exact mass: 326.01

Example 87: 2-[3-(4-Fluorophenyl)-2-(2-oxoindolin-5-yl)phenyl]acetonitrile

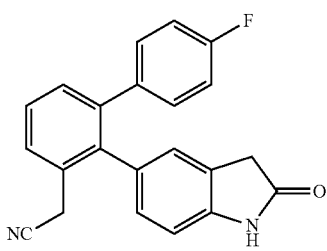 [SMILES: N#CCc1cccc(-c2ccc(F)cc2)c1-c1ccc2c(c1)CC(=O)N2]

Predicted Chemical Formula: $C_{22}H_{15}FN_2O$, Exact mass: 342.12

Example 88: 2-[3-(2-Fluorophenyl)-2-(2-oxoindolin-5-yl)phenyl]acetonitrile

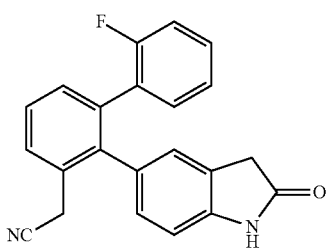 [SMILES: N#CCc1cccc(-c2ccccc2F)c1-c1ccc2c(c1)CC(=O)N2]

Predicted Chemical Formula: $C_{22}H_{15}FN_2O$, Exact mass: 342.12

Example 89: 2-[3-(4-Methoxyphenyl)-2-(2-oxoindolin-5-yl)phenyl]acetonitrile

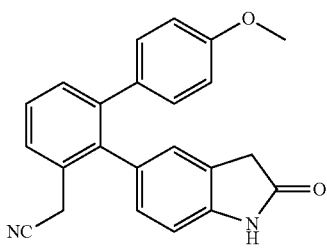 [SMILES: COc1ccc(-c2cccc(CC#N)c2-c2ccc3c(c2)CC(=O)N3)cc1]

Predicted Chemical Formula: $C_{23}H_{18}N_2O_2$, Exact mass: 354.14

Example 90: 2-[3-Cyclopropyl-2-(2-oxoindolin-5-yl)phenyl]acetonitrile

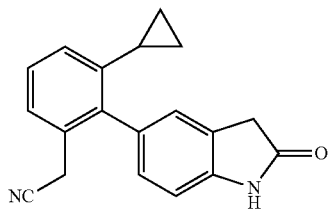 [SMILES: N#CCc1cccc(C2CC2)c1-c1ccc2c(c1)CC(=O)N2]

Predicted Chemical Formula: $C_{19}H_{16}N_2O$, Exact mass: 288.13

Example 91: 5-(2-Chloro-6-cyclopropyl-phenyl)-indolin-2-one

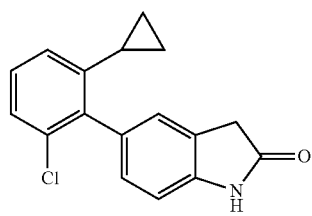 [SMILES: O=C1Cc2cc(-c3c(Cl)cccc3C3CC3)ccc2N1]

Predicted Chemical Formula: $C_{17}H_{14}ClNO$, Exact mass: 283.08

Example 92: 5-(2-Chloro-6-vinyl-phenyl)-indolin-2-one

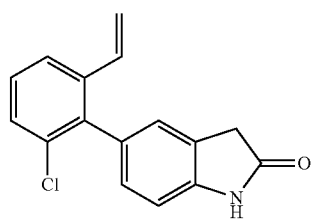 [SMILES: C=Cc1cccc(Cl)c1-c1ccc2c(c1)CC(=O)N2]

Predicted Chemical Formula: $C_{16}H_{12}ClNO$, Exact mass: 269.06

Example 93: 5-(2-Chloro-6-phenyl-phenyl)-indolin-2-one

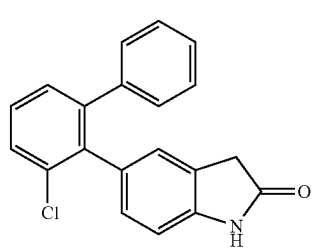 [SMILES: O=C1Cc2cc(-c3c(Cl)cccc3-c3ccccc3)ccc2N1]

Predicted Chemical Formula: $C_{20}H_{14}ClNO$, Exact mass: 319.08

Example 94: 5-[2-Chloro-6-(4-fluorophenyl)phenyl]-indolin-2-one

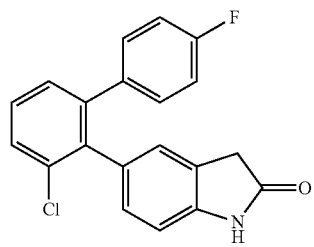 [SMILES: O=C1Cc2cc(-c3c(Cl)cccc3-c3ccc(F)cc3)ccc2N1]

Predicted Chemical Formula: $C_{20}H_{13}ClFNO$, Exact mass: 337.07

Example 95: 4-[3-Chloro-2-(2-oxoindolin-5-yl)phenyl]benzonitrile

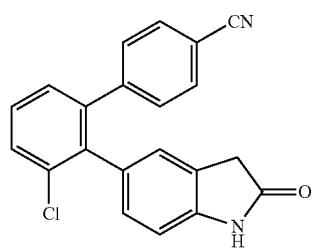 [SMILES: N#Cc1ccc(-c2cccc(Cl)c2-c2ccc3c(c2)CC(=O)N3)cc1]

Predicted Chemical Formula: $C_{21}H_{13}ClN_2O$, Exact mass: 344.07

Example 96: 5-[2-Chloro-6-(3-pyridyl)phenyl]-indolin-2-one

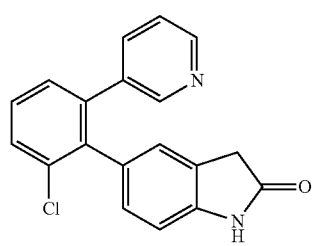 [SMILES: O=C1Cc2cc(-c3c(Cl)cccc3-c3cccnc3)ccc2N1]

Predicted Chemical Formula: $C_{19}H_{13}ClN_2O$, Exact mass: 320.07

Example 97: 5-[2-Chloro-6-(5-fluoro-3-pyridyl)phenyl]-indolin-2-one

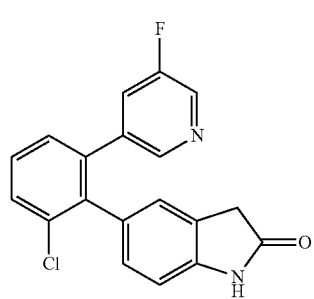 [SMILES: O=C1Cc2cc(-c3c(Cl)cccc3-c3cncc(F)c3)ccc2N1]

Predicted Chemical Formula: C₁₉H₁₂ClFN₂O, Exact mass: 338.06

Example 98: 5-[2-Chloro-6-(6-fluoro-3-pyridyl)phenyl]-indolin-2-one

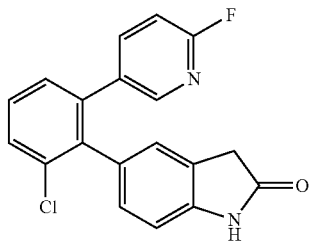 [SMILES: O=C1Cc2cc(-c3c(Cl)cccc3-c3ccc(F)nc3)ccc2N1]

Predicted Chemical Formula: C₁₉H₁₂ClFN₂O, Exact mass: 338.06

Example 99: 5-[2-Chloro-6-(5-methoxy-3-pyridyl)phenyl]-indolin-2-one

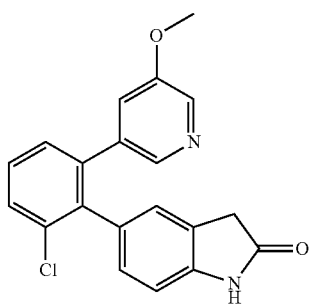 [SMILES: COc1cncc(-c2cccc(Cl)c2-c2ccc3c(c2)CC(=O)N3)c1]

Predicted Chemical Formula: C₂₀H₁₅ClN₂O₂, Exact mass: 350.08

Example 100: 5-[2-Chloro-6-[5-(trifluoromethyl)-3-pyridyl]phenyl]-indolin-2-one

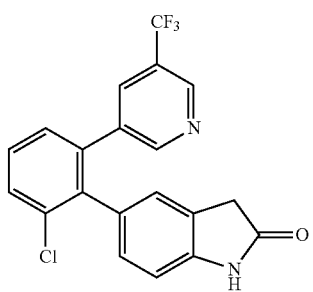 [SMILES: O=C1Cc2cc(-c3c(Cl)cccc3-c3cncc(C(F)(F)F)c3)ccc2N1]

Predicted Chemical Formula: C₂₀H₁₂ClF₃N₂O, Exact mass: 388.06

Example 101: 5-[2-Chloro-6-(4-pyridyl)phenyl]-indolin-2-one

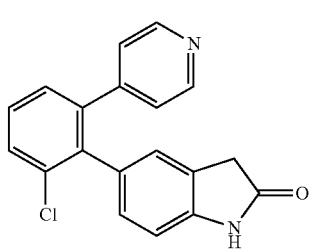 [SMILES: O=C1Cc2cc(-c3c(Cl)cccc3-c3ccncc3)ccc2N1]

Predicted Chemical Formula: C₁₉H₁₃ClN₂O, Exact mass: 320.07

Example 102: 5-[2-Chloro-6-(3-methoxy-4-pyridyl)phenyl]-indolin-2-one

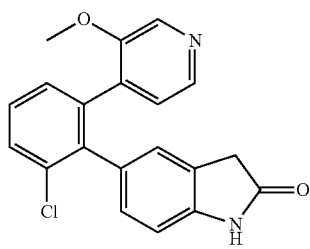 [SMILES: COc1cnccc1-c1cccc(Cl)c1-c1ccc2c(c1)CC(=O)N2]

Predicted Chemical Formula: C₂₀H₁₅ClN₂O₂, Exact mass: 350.08

Example 103: 5-[2-Chloro-6-[1-(2-methoxyethyl)pyrazol-4-yl]phenyl]-indolin-2-one

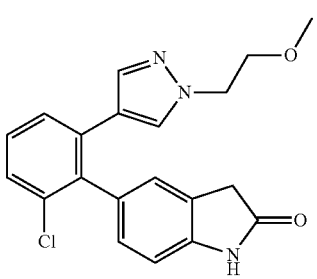 [SMILES: COCCn1cc(-c2cccc(Cl)c2-c2ccc3c(c2)CC(=O)N3)cn1]

Predicted Chemical Formula: C₂₀H₁₈ClN₃O₂, Exact mass: 367.11

Example 104: 5-[2-Chloro-6-(1-methylpyrazol-4-yl)phenyl]-indolin-2-one

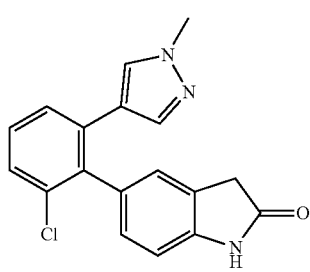 [SMILES: Cn1cc(-c2cccc(Cl)c2-c2ccc3c(c2)CC(=O)N3)cn1]

Predicted Chemical Formula: C₁₈H₁₄ClN₃O, Exact mass: 323.08

Example 105: 5-[2-Chloro-6-(3,5-dimethylisoxazol-4-yl)phenyl]-indolin-2-one

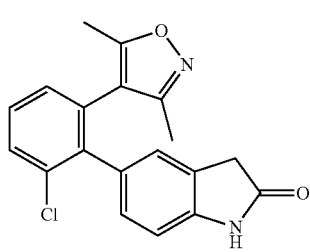 [SMILES: Cc1noc(C)c1-c1cccc(Cl)c1-c1ccc2c(c1)CC(=O)N2]

Predicted Chemical Formula: $C_{19}H_{15}ClN_2O_2$, Exact mass: 338.08

Example 106: 5-[2-Chloro-6-(2-isopropylpyrazol-3-yl)phenyl]-indolin-2-one

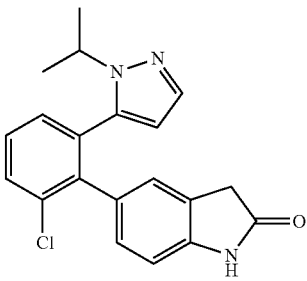 [SMILES: CC(C)n1nccc1-c1cccc(Cl)c1-c1ccc2c(c1)CC(=O)N2]

Predicted Chemical Formula: $C_{20}H_{18}ClN_3O$, Exact mass: 351.11

Example 107: 5-[2-Chloro-6-(1H-pyrazol-4-yl)phenyl]-indolin-2-one

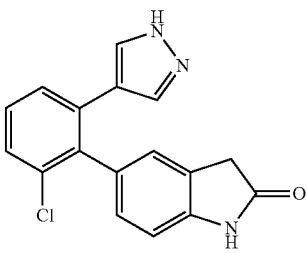 [SMILES: O=C1Cc2cc(-c3c(Cl)cccc3-c3cn[nH]c3)ccc2N1]

Predicted Chemical Formula: $C_{17}H_{12}ClN_3O$, Exact mass: 309.07

Example 108: 5-[2-Chloro-6-(1,5-dimethylpyrazol-4-yl)phenyl]-indolin-2-one

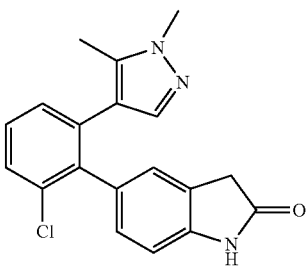 [SMILES: Cc1c(-c2cccc(Cl)c2-c2ccc3c(c2)CC(=O)N3)cnn1C]

Predicted Chemical Formula: $C_{19}H_{16}ClN_3O$, Exact mass: 337.10

Example 109: 5-(2-Chloro-6-pyrimidin-5-yl-phenyl)-indolin-2-one

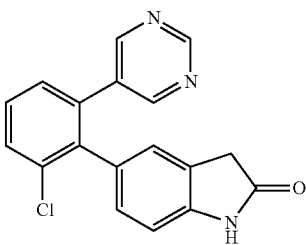 [SMILES: O=C1Cc2cc(-c3c(Cl)cccc3-c3cncnc3)ccc2N1]

Predicted Chemical Formula: $C_{18}H_{12}ClN_3O$, Exact mass: 321.07

Example 110: 5-(2-Methyl-6-phenyl-phenyl)-indolin-2-one

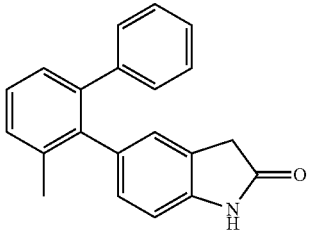 [SMILES: Cc1cccc(-c2ccccc2)c1-c1ccc2c(c1)CC(=O)N2]

Predicted Chemical Formula: $C_{21}H_{17}NO$, Exact mass: 299.13

Example 111: 5-[2-(2-Fluorophenyl)-6-methyl-phenyl]-indolin-2-one

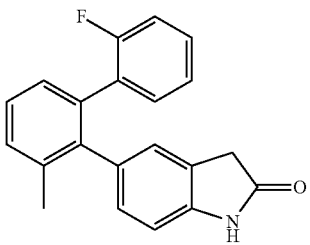 [SMILES: Cc1cccc(-c2ccccc2F)c1-c1ccc2c(c1)CC(=O)N2]

Predicted Chemical Formula: $C_{21}H_{16}FNO$, Exact mass: 317.12

Example 112: 5-[2-(4-Fluorophenyl)-6-methyl-phenyl]-indolin-2-one

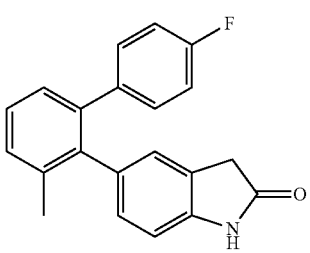 [SMILES: Cc1cccc(-c2ccc(F)cc2)c1-c1ccc2c(c1)CC(=O)N2]

Predicted Chemical Formula: $C_{21}H_{16}FNO$, Exact mass: 317.12

Example 113: 5-[2-Methoxy-6-(8-quinolyl)phenyl]-indolin-2-one

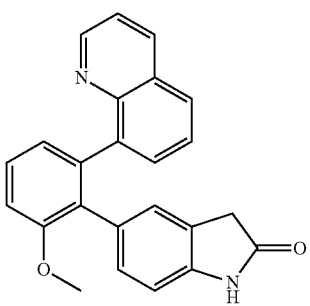 [SMILES: COc1cccc(-c2cccc3cccnc23)c1-c1ccc2c(c1)CC(=O)N2]

Predicted Chemical Formula: $C_{24}H_{18}N_2O_2$, Exact mass: 366.14

Example 114: 2-Chloro-3-(2-oxoindolin-5-yl)-4-(trifluoromethoxy)benzonitrile

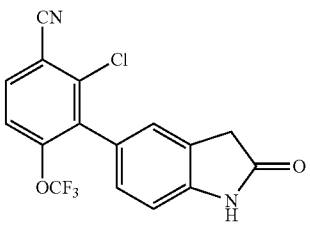 [SMILES: N#Cc1ccc(OC(F)(F)F)c(-c2ccc3c(c2)CC(=O)N3)c1Cl]

Predicted Chemical Formula: $C_{16}H_8ClF_3N_2O_2$, Exact mass: 352.02

Example 115: 4-Chloro-3-(2-oxoindolin-5-yl)-2-(trifluoromethoxy)benzonitrile

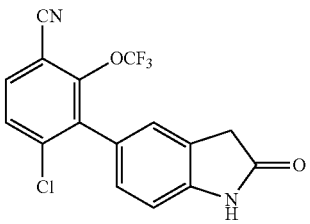 [SMILES: N#Cc1ccc(Cl)c(-c2ccc3c(c2)CC(=O)N3)c1OC(F)(F)F]

The title compound was prepared in a manner analogous to Example 2, substituting 4-chloro-3-iodo-2-(trifluoromethoxy)benzonitrile (Intermediate 6) for 1-bromo-3-chloro-2-iodobenzene. MS (ESI): mass calcd. for $C_{14}H_8ClF_3N_2O_2$, 352.0; m/z found, 353.7 [M+H]$^+$. $^1$H NMR (500 MHz, DMSO-d$_6$) δ 10.57 (s, 1H), 8.10 (d, J=8.5 Hz, 1H), 7.92 (d, J=8.5 Hz, 1H), 7.26-7.12 (m, 2H), 6.94 (dd, J=8.0, 0.5 Hz, 1H), 3.55 (s, 2H).

Example 116: 5-(2-Chloro-6-(trifluoromethoxy)phenyl)-6-fluoroindolin-2-one

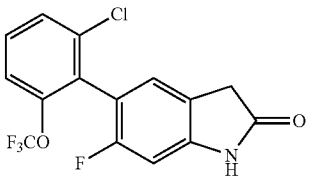 [SMILES: O=C1Cc2cc(-c3c(Cl)cccc3OC(F)(F)F)c(F)cc2N1]

Predicted Chemical Formula: $C_{15}H_8ClF_4NO_2$, Exact mass: 345.02

Example 117: 5-(2-Chloro-6-(trifluoromethoxy)phenyl)-7-fluoroindolin-2-one

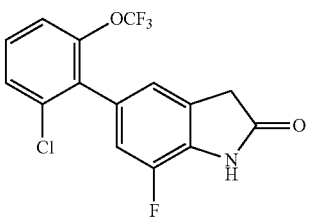

The title compound was prepared in a manner analogous to Example 2, substituting 7-fluoro-5-(4,4,5,5-tetramethyl-1,3,2-dioxaborolan-2-yl)indolin-2-one (Intermediate 4) for 5-(4,4,5,5-tetramethyl-1,3,2-dioxaborolan-2-yl)indolin-2-one, and 1-chloro-2-iodo-3-(trifluoromethoxy)benzene for 1-bromo-3-chloro-2-iodobenzene, and PdCl$_2$(dtpf) for PdCl$_2$(dppf)-CH$_2$Cl$_2$. MS (ESI): mass calcd. for $C_{15}H_8ClF_4NO_2$, 345.6; m/z found, 346.6 [M+H]$^+$. $^1$H NMR (500 MHz, DMSO-d$_6$) δ 11.01 (s, 1H), 7.65 (dd, J=8.1, 1.2 Hz, 1H), 7.56 (t, J=8.2 Hz, 1H), 7.53-7.46 (m, 1H), 7.08 (dd, J=10.8, 1.4 Hz, 1H), 6.99 (d, J=1.5 Hz, 1H), 3.64 (t, J=1.0 Hz, 2H).

Example 118: 5-(2-Chloro-6-(difluoromethoxy)phenyl)-7-fluoroindolin-2-one

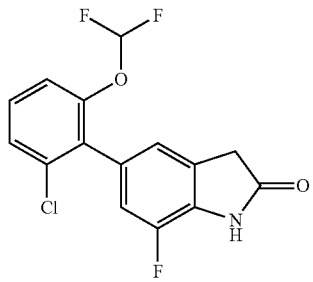

Step A:
2-Bromo-1-chloro-3-(difluoromethoxy)benzene

To a cold (−78° C.) solution of 2-bromo-3-chlorophenol (1.0 g, 4.8 mmol) and potassium hydroxide (5.4 g, 96.4 mmol) in acetonitrile (40 mL) and water (40 mL) was added diethyl (bromodifluoromethyl)phosphonate (1.7 mL, 9.6 mmol) at once. After 20 minutes the reaction mixture was warmed to rt and stirred for 16 h. The mixture was then diluted with water and extracted with EtOAc (×3). The combined organic extracts were dried over Na$_2$SO$_4$ and concentrated to obtain the product as an oil (1.2 g, 87% yield), which was used directly in the next reaction. $^1$H NMR (500 MHz, CDCl$_3$) δ 7.38-7.33 (m, 1H), 7.30-7.23 (m, 1H), 7.13 (m, J=8.3, 1.1 Hz, 1H), 6.54 (t, J=73.1 Hz, 1H).

Step B: 5-(2-Chloro-6-(difluoromethoxy)phenyl)-7-fluoroindolin-2-one

The title compound was prepared in a manner analogous to Example 2, substituting 2-bromo-1-chloro-3-(difluoromethoxy)benzene for 1-bromo-3-chloro-2-iodobenzene and 7-fluoro-5-(4,4,5,5-tetramethyl-1,3,2-dioxaborolan-2-yl)indolin-2-one (Intermediate 4) for 5-(4,4,5,5-tetramethyl-1,3,2-dioxaborolan-2-yl)indolin-2-one. MS (ESI): mass calcd. for $C_{15}H_9ClF_3NO_2$, 327.6; m/z found, 328.6 [M+H]$^+$. $^1$H NMR (400 MHz, DMSO-d$_6$) δ 10.98 (s, 1H), 7.51-7.46 (m, 2H), 7.33-7.25 (m, 1H), 7.17-6.92 (m, 3H), 3.62 (s, 2H).

Example 119: 2-(3-Chloro-2-(7-fluoro-2-oxoindolin-5-yl)phenyl)-2-methylpropanenitrile

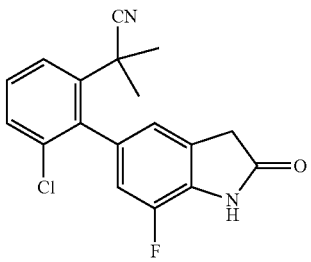

The title compound was prepared in a manner analogous to Example 81, substituting 7-fluoro-5-(4,4,5,5-tetramethyl-1,3,2-dioxaborolan-2-yl)indolin-2-one (Intermediate 4) for 5-(4,4,5,5-tetramethyl-1,3,2-dioxaborolan-2-yl)indolin-2-one in Step B. MS (ESI): mass calcd. for $C_{18}H_{14}ClFN_2O$, 328.7; m/z found, 329.7 $^1$H NMR (400 MHz, DMSO-$d_6$) δ 11.00 (s, 1H), 7.68-7.54 (m, 2H), 7.54-7.44 (m, 1H), 7.11-6.91 (m, 2H), 3.68-3.53 (m, 2H), 1.63 (s, 3H), 1.58 (s, 3H).

Example 120: 6-Bromo-5-(2-chloro-6-(trifluoromethoxy)phenyl)indolin-2-one

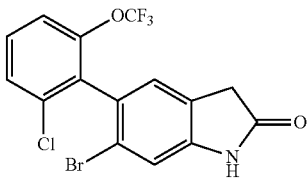 [SMILES: O=C1Cc2cc(-c3c(Cl)cccc3OC(F)(F)F)c(Br)cc2N1]

Predicted Chemical Formula $C_{15}H_8BrClF_3NO_2$, Exact mass: 404.94

Example 121: 5-(2-Chloro-3-(4-methoxypiperidin-1-yl)phenyl)-7-fluoroindolin-2-one

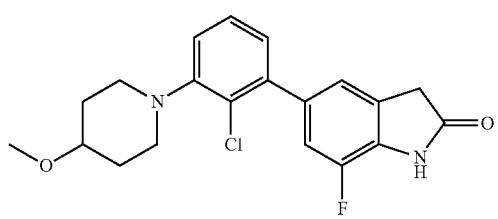 [SMILES: COC1CCN(c2cccc(-c3cc(F)c4c(c3)CC(=O)N4)c2Cl)CC1]

Step A: 1-(3-Bromo-2-chlorophenyl)-4-methoxypiperidine

To a suspension of 1,3-dibromo-2-chlorobenzene (300 mg, 1.11 mmol), 4-methoxypiperidine (168 mg, 1.11 mmol), sodium tert-butoxide (160 mg, 1.67 mmol) in toluene (3.0 ml), was added BINAP (35 mg, 0.05 mmol) and Pd$_2$(dba)$_3$ (20 mg, 0.02 mmol) at once. The mixture was degassed with nitrogen for 10 minutes and then heated at 140° C. for 1 h in microwave. After cooling to rt, the reaction mixture was diluted with water and extracted with EtOAc (×3). The combined organic extracts were dried over Na$_2$SO$_4$ and concentrated. Purification (FCC, SiO$_2$; 0-100% EtOAc/hexanes) afforded the title compound as a oil (168 mg, 50% yield). MS (ESI): mass calcd. for $C_{12}H_{15}BrClNO$, 304.6; m/z found, 305.6 [M+H]$^+$. $^1$H NMR (400 MHz, DMSO-$d_6$) δ 7.42 (dd, J=7.7, 1.7 Hz, 1H), 7.28-7.14 (m, 2H), 3.39-3.33 (m, 1H), 3.28 (s, 3H), 3.14 (dt, J=10.5, 4.5 Hz, 2H), 2.77 (ddd, J=12.0, 9.2, 3.0 Hz, 2H), 2.04-1.91 (m, 2H), 1.61 (dtd, J=12.2, 8.8, 3.4 Hz, 2H).

Step B: 5-(2-Chloro-3-(4-methoxypiperidin-1-yl)phenyl)-7-fluoroindolin-2-one The title compound was prepared in a manner analogous to Example 2, substituting 1-(3-bromo-2-chlorophenyl)-4-methoxypiperidine for 1-bromo-3-chloro-2-iodobenzene and 7-fluoro-5-(4,4,5,5-tetramethyl-1,3,2-dioxaborolan-2-yl)indolin-2-one (Intermediate 4) for 5-(4,4,5,5-tetramethyl-1,3,2-dioxaborolan-2-yl)indolin-2-one. MS (ESI): mass calcd. for $C_{20}H_{20}ClFN_2O_2$, 374.8; m/z found, 375.8 $^1$H NMR (500 MHz, DMSO-$d_6$) δ 10.94 (s, 1H), 7.38-7.25 (m, 1H), 7.18-7.05 (m, 3H), 7.01 (dd, J=7.5, 1.5 Hz, 1H), 3.61 (t, J=0.9 Hz, 2H), 3.28 (s, 3H), 3.24-3.13 (m, 2H), 2.79 (ddd, J=11.8, 9.1, 2.8 Hz, 2H), 1.97 (dd, J=11.0, 4.4 Hz, 2H), 1.68-1.55 (m, 2H), 1.07 (s, 1H).

Example 122: 5-[2-(Difluoromethoxy)-6-methylphenyl]-7-fluoro-indolin-2-one

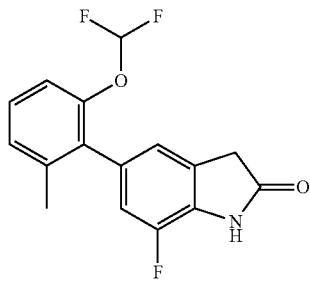 [SMILES: Cc1cccc(OC(F)F)c1-c1cc(F)c2c(c1)CC(=O)N2]

The title compound was prepared in a manner analogous to Example 118, substituting 2-bromo-3-methylphenol for 2-bromo-3-chlorophenol in Step A. MS (ESI): mass calcd. for $C_{16}H_{12}F_3NO_2$, 307.1; m/z found, 308.00 [M+H]$^+$. $^1$H NMR (400 MHz, CDCl$_3$) δ 8.02 (s, 1H), 7.31-7.25 (m, 1H), 7.17-7.12 (m, 1H), 7.07 (d, J=8.2 Hz, 1H), 6.62-6.53 (m, 2H), 6.33 (t, J=74.0 Hz, 1H), 3.61 (s, 2H), 2.13 (s, 3H).

Example 123: 5-[2-(Difluoromethoxy)-6-methoxyphenyl]-7-fluoro-indolin-2-one

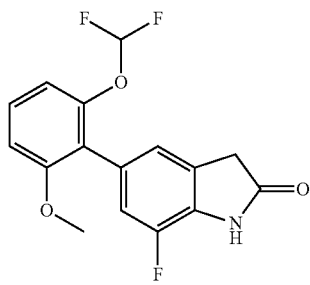 [SMILES: COc1cccc(OC(F)F)c1-c1cc(F)c2c(c1)CC(=O)N2]

The title compound was prepared in a manner analogous to Example 118, substituting 2-bromo-3-methoxyphenol for 2-bromo-3-chlorophenol in Step A. MS (ESI): mass calcd. for $C_{16}H_{12}F_3NO_3$, 323.1; m/z found, 324.00 [M+H]$^+$. $^1$H NMR (400 MHz, CDCl$_3$) δ 7.87 (s, 1H), 7.34 (t, J=8.4 Hz, 1H), 6.89-6.84 (m, 2H), 6.72 (dd, J=9.4, 1.2 Hz, 1H), 6.66-6.62 (m, 1H), 6.34 (t, J=73.8 Hz, 1H), 3.78 (s, 3H), 3.61-3.56 (m, 2H).

Example 124: 2-Chloro-3-(7-fluoro-2-oxo-indolin-5-yl)-4-(trifluoromethoxy)benzonitrile

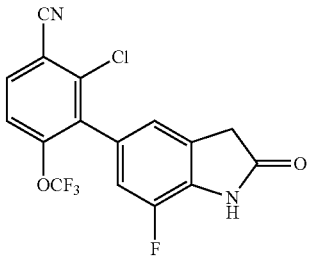 [SMILES: N#Cc1ccc(OC(F)(F)F)c(-c2cc(F)c3c(c2)CC(=O)N3)c1Cl]

The title compound was prepared in a manner analogous to Example 2, substituting 2-chloro-3-iodo-4-(trifluoromethoxy)benzonitrile (Intermediate 3) for 1-bromo-3-chloro-2-iodobenzene and 7-fluoro-5-(4,4,5,5-tetramethyl-1,3,2-dioxaborolan-2-yl)indolin-2-one (Intermediate 4) for 5-(4,4,5,5-tetramethyl-1,3,2-dioxaborolan-2-yl)indolin-2-one. MS (ESI): mass calcd. for C$_{16}$H$_7$ClF$_4$N$_2$O$_2$, 370.0; m/z found, 370.9 [M+H]$^+$. $^1$H NMR (500 MHz, DMSO-d$_6$) δ 11.06 (s, 1H), 8.18 (d, J=8.8 Hz, 1H), 7.77-7.64 (m, 1H), 7.21-7.14 (m, 1H), 7.08-7.03 (m, 1H), 3.65 (s, 2H).

Example 125: 5-(3,5-Dimethyl-4-pyridyl)-7-fluoro-indolin-2-one

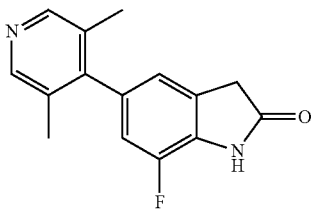 [SMILES: Cc1cncc(C)c1-c1cc(F)c2c(c1)CC(=O)N2]

The title compound was prepared in a manner analogous to Example 2, substituting 4-bromo-3,5-dimethylpyridine hydrochloride for 1-bromo-3-chloro-2-iodobenzene and 7-fluoro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for C$_{15}$H$_{13}$FN$_2$O, 256.1; m/z found, 257.00 [M+H]$^+$. $^1$H NMR (500 MHz, MeOD) δ 8.28 (s, 2H), 6.92-6.86 (m, 2H), 3.68-3.62 (m, 2H), 2.08 (s, 6H).

Example 126: 5-(3,5-Dichloro-4-pyridyl)-7-fluoro-indolin-2-one

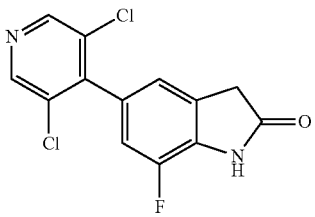

The title compound was prepared in a manner analogous to Example 2, substituting 3,5-dichloro-4-iodopyridine for 1-bromo-3-chloro-2-iodobenzene and 7-fluoro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for C$_{13}$H$_7$Cl$_2$FN$_2$O, 296.0; m/z found, 296.90 [M+H]$^+$. $^1$H NMR (500 MHz, MeOD) δ 8.61 (s, 2H), 7.07-7.03 (m, 2H), 3.70-3.63 (m, 2H).

Example 127: 5-[2-Chloro-6-(trifluoromethoxy)phenyl]-7-methyl-indolin-2-one

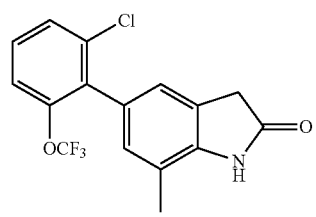 [SMILES: Cc1cc(-c2c(Cl)cccc2OC(F)(F)F)cc2c1NC(=O)C2]

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. The reaction mixture was heated at 95° C. for 2 h. MS (ESI): mass calcd. for C$_{16}$H$_{11}$ClF$_3$NO$_2$, 341.7; m/z found, 342.0 [M+H]$^+$. $^1$H NMR (500 MHz, DMSO-d$_6$) δ 10.57 (s, 1H), 7.63-7.61 (m, 1H), 7.52 (t, J=8.2 Hz, 1H), 7.48-7.45 (m, 1H), 6.93 (d, J=1.7 Hz, 1H), 6.91-6.86 (m, 1H), 3.54 (s, 2H), 2.23 (s, 3H).

Example 128: 5-[2-Chloro-6-(difluoromethoxy)phenyl]-7-methyl-indolin-2-one

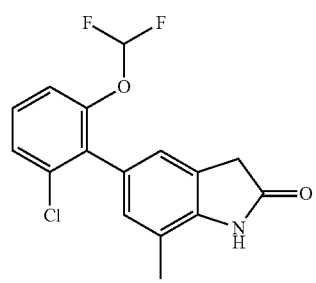 [SMILES: Cc1cc(-c2c(Cl)cccc2OC(F)F)cc2c1NC(=O)C2]

The title compound was prepared in a manner analogous to Example 118, substituting 7-methyl-5-(4,4,5,5-tetramethyl-1,3,2-dioxaborolan-2-yl)indolin-2-one for 7-fluoro-5-(4,4,5,5-tetramethyl-1,3,2-dioxaborolan-2-yl)indolin-2-one in Step B. MS (ESI): mass calcd. for C$_{16}$H$_{12}$ClF$_2$NO$_2$, 323.1; m/z found, 324.0 [M+H]$^+$. $^1$H NMR (400 MHz, DMSO-d$_6$) δ 10.53 (s, 1H), 7.47-7.41 (m, 2H), 7.29-7.25 (m, 1H), 6.92 (d, J=3.0 Hz, 1H), 6.88-6.87 (m, 1H), 3.92 (s, 1H), 3.53 (s, 2H), 2.23 (s, 3H).

Example 129: 5-[2-(Difluoromethoxy)-6-methyl-phenyl]-7-methyl-indolin-2-one

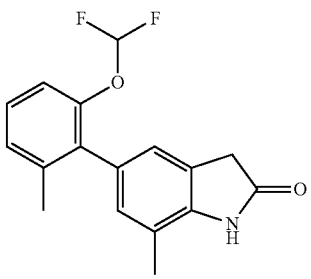 [SMILES: Cc1cc(-c2c(C)cccc2OC(F)F)cc2c1NC(=O)C2]

The title compound was prepared in a manner analogous to Example 118, substituting 2-bromo-3-methylphenol for 2-bromo-3-chlorophenol in Step A and 7-methyl-5-(4,4,5,5-tetramethyl-1,3,2-dioxaborolan-2-yl)indolin-2-one for 7-fluoro-5-(4,4,5,5-tetramethyl-1,3,2-dioxaborolan-2-yl)indolin-2-one in Step B. MS (ESI): mass calcd. for $C_{17}H_{15}F_2NO_2$, 303.1; m/z found, 304.20 [M+H]$^+$. $^1$H NMR (400 MHz, CDCl$_3$) δ 9.75 (s, 1H), 7.27-7.20 (m, 1H), 7.17-7.12 (m, 1H), 7.06 (d, J=8.0 Hz, 1H), 6.93-6.86 (m, 2H), 6.29 (t, J=74.5 Hz, 1H), 3.64-3.59 (m, 2H), 2.35 (s, 3H), 2.13 (s, 3H).

Example 130: 5-[2-(Difluoromethoxy)-6-methoxy-phenyl]-7-methyl-indolin-2-one

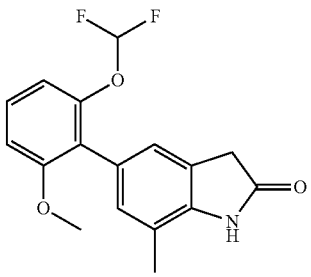 [SMILES: COc1cccc(OC(F)F)c1-c1cc(C)c2c(c1)CC(=O)N2]

The title compound was prepared in a manner analogous to Example 118, substituting 2-bromo-3-methoxyphenol for 2-bromo-3-chlorophenol in Step A and 7-methyl-5-(4,4,5,5-tetramethyl-1,3,2-dioxaborolan-2-yl)indolin-2-one for 7-fluoro-5-(4,4,5,5-tetramethyl-1,3,2-dioxaborolan-2-yl)indolin-2-one in Step B. MS (ESI): mass calcd. for $C_{17}H_{15}F_2NO_3$, 319.1; m/z found, 320.00 [M+H]$^+$. $^1$H NMR (400 MHz, CDCl$_3$) δ 9.57 (s, 1H), 7.29 (t, J=8.3 Hz, 1H), 7.05-6.99 (m, 2H), 6.89-6.83 (m, 2H), 6.30 (t, J=74.3 Hz, 1H), 3.77 (s, 3H), 3.64-3.58 (m, 2H), 2.34 (s, 3H).

Example 131: 5-[2-(Difluoromethoxy)-6-fluoro-phenyl]-7-methyl-indolin-2-one

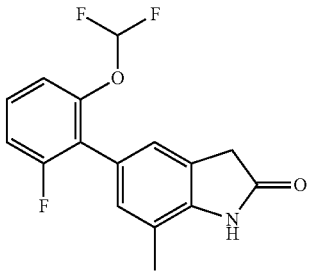 [SMILES: Cc1cc(-c2c(F)cccc2OC(F)F)cc2c1NC(=O)C2]

The title compound was prepared in a manner analogous to Example 118, substituting 2-bromo-3-fluorophenol for 2-bromo-3-chlorophenol in Step A and 7-methyl-5-(4,4,5,5-tetramethyl-1,3,2-dioxaborolan-2-yl)indolin-2-one for 7-fluoro-5-(4,4,5,5-tetramethyl-1,3,2-dioxaborolan-2-yl)indolin-2-one in step B. MS (ESI): mass calcd. for $C_{16}H_{12}F_3NO_2$, 307.1; m/z found, 308.10 [M+H]$^+$. $^1$H NMR (400 MHz, CDCl$_3$) δ 9.83 (s, 1H), 7.33-7.26 (m, 1H), 7.11-7.07 (m, 2H), 7.07-7.01 (m, 2H), 6.35 (t, J=73.7 Hz, 1H), 3.62 (s, 2H), 2.36 (s, 3H).

Example 132: 2-[3-Chloro-2-(7-methyl-2-oxo-indolin-5-yl)phenyl]-2-methyl-propanenitrile

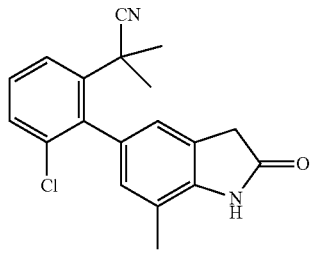 [SMILES: Cc1cc(-c2c(Cl)cccc2C(C)(C)C#N)cc2c1NC(=O)C2]

The title compound was prepared in a manner analogous to Example 81 substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one in Step B. MS (ESI): mass calcd. for $C_{19}H_{17}ClN_2O$, 324.1; m/z found, 325.0 [M+H]$^+$. $^1$H NMR (400 MHz, DMSO-d$_6$) δ 10.56 (s, 1H), 7.61 (dd, J=8.0, 1.3 Hz, 1H), 7.57-7.54 (m, 1H), 7.47-7.42 (m, 1H), 6.89 (d, J=1.5 Hz, 1H), 6.87-6.85 (m, 1H), 3.60-3.42 (m, 2H), 2.22 (s, 3H), 1.57 (s, 3H), 1.55 (s, 3H).

Example 133: 4-Chloro-3-(7-methyl-2-oxoindolin-5-yl)-2-(trifluoromethoxy)benzonitrile

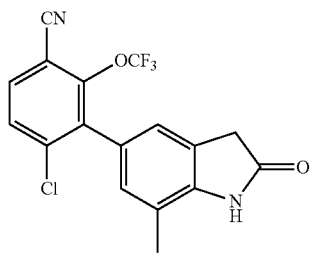 [SMILES: Cc1cc(-c2c(Cl)ccc(C#N)c2OC(F)(F)F)cc2c1NC(=O)C2]

The title compound was prepared in a manner analogous to Example 2, substituting 2-chloro-3-iodo-4-(trifluoromethoxy)benzonitrile (Intermediate 6) for 1-bromo-3-chloro-2-iodobenzene and 7-methyl-5-(4,4,5,5-tetramethyl-1,3,2-dioxaborolan-2-yl)indolin-2-one (Intermediate 5) for 5-(4,4,5,5-tetramethyl-1,3,2-dioxaborolan-2-yl)indolin-2-one. MS (ESI): mass calcd. for $C_{17}H_{10}ClF_3N_2O_2$, 366.0; m/z found, 367.05 [M+H]$^+$. $^1$H NMR (500 MHz, DMSO-d$_6$) δ 10.62 (s, 1H), 8.09 (d, J=8.5 Hz, 1H), 7.91 (d, J=8.5 Hz, 1H), 7.04 (d, J=1.7 Hz, 1H), 7.01-6.97 (m, 1H), 3.55 (s, 2H), 2.24 (s, 3H).

Example 134: 2-Methyl-3-(7-methyl-2-oxo-indolin-5-yl)benzonitrile

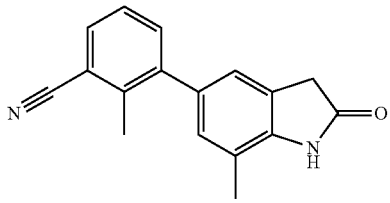 [SMILES: Cc1cc(-c2cccc(C#N)c2C)cc2c1NC(=O)C2]

The title compound was prepared in a manner analogous to Example 2, substituting 3-bromo-2-methylbenzonitrile for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{17}H_{14}N_2O$, 262.1; m/z found, 263.20 [M+H]$^+$. $^1$H NMR (500 MHz, CDCl$_3$) δ 9.56 (s, 1H), 7.60 (dd, J=7.8, 1.5 Hz, 1H), 7.41 (dd, J=7.7, 1.5 Hz, 1H), 7.34-7.28 (m, 1H), 7.02-6.93 (m, 2H), 3.64 (s, 2H), 2.46 (s, 3H), 2.37 (s, 3H).

Example 135: 5-(2-Chloro-6-methyl-phenyl)-7-methyl-indolin-2-one

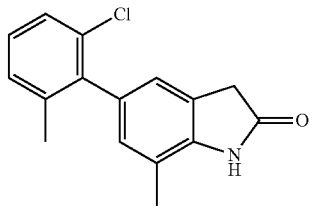 [SMILES: Cc1cc(-c2c(C)cccc2Cl)cc2c1NC(=O)C2]

The title compound was prepared in a manner analogous to Example 2, substituting 3-chloro-2-iodotoluene for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{14}ClNO$, 271.1; m/z found, 272.10 [M+H]$^+$. $^1$H NMR (500 MHz, CDCl$_3$) δ 9.62 (s, 1H), 7.33-7.28 (m, 1H), 7.21-7.12 (m, 2H), 6.93-6.84 (m, 2H), 3.69-3.53 (m, 2H), 2.36 (s, 3H), 2.10 (s, 3H).

Example 136: 5-(2-Fluoro-6-methyl-phenyl)-7-methyl-indolin-2-one

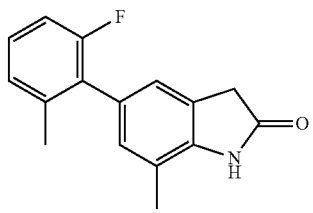 [SMILES: Cc1cc(-c2c(C)cccc2F)cc2c1NC(=O)C2]

The title compound was prepared in a manner analogous to Example 2, substituting 2-bromo-3-fluorotoluene for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{14}FNO$, 255.1; m/z found, 256.20 [M+H]$^+$. $^1$H NMR (500 MHz, CDCl$_3$) δ 10.00 (s, 1H), 7.19 (td, J=7.9, 5.7 Hz, 1H), 7.05 (d, J=7.6 Hz, 1H), 7.00-6.90 (m, 3H), 3.61 (s, 2H), 2.36 (s, 3H), 2.17 (s, 3H).

Example 137: 7-Methyl-5-[2-methyl-6-(trifluoromethyl)phenyl]indolin-2-one

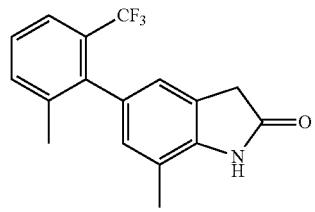 [SMILES: Cc1cc(-c2c(C)cccc2C(F)(F)F)cc2c1NC(=O)C2]

The title compound was prepared in a manner analogous to Example 2, substituting 2-bromo-3-methylbenzotrifluoride for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{17}H_{14}F_3NO$, 305.1; m/z found, 306.10 [M+H]$^+$. $^1$H NMR (500 MHz, CDCl$_3$) δ 9.93 (s, 1H), 7.61-7.53 (m, 1H), 7.43 (d, J=7.6 Hz, 1H), 7.37-7.30 (m, 1H), 6.89-6.80 (m, 2H), 3.59 (s, 2H), 2.36 (s, 3H), 2.04 (s, 3H).

Example 138: 3-Methyl-2-(7-methyl-2-oxo-indolin-5-yl)benzonitrile

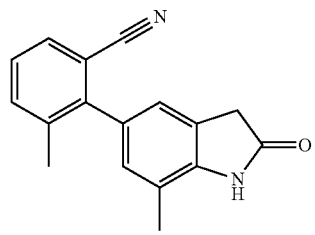 [SMILES: Cc1cc(-c2c(C)cccc2C#N)cc2c1NC(=O)C2]

The title compound was prepared in a manner analogous to Example 2, substituting 2-bromo-3-methylbenzonitrile for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{17}H_{14}N_2O$, 262.1; m/z found, 263.20 [M+H]$^+$. $^1$H NMR (500 MHz, CDCl$_3$) δ 8.95 (s, 1H), 7.59-7.54 (m, 1H), 7.50-7.45 (m, 1H), 7.33 (t, J=7.7 Hz, 1H), 7.02-6.94 (m, 2H), 3.70-3.57 (m, 2H), 2.35 (s, 3H), 2.19 (s, 3H).

Example 139: 5-(2-Fluoro-6-methoxy-phenyl)-7-methyl-indolin-2-one

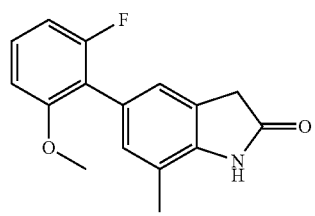 [SMILES: COc1cccc(F)c1-c1cc(C)c2c(c1)CC(=O)N2]

The title compound was prepared in a manner analogous to Example 2, substituting 2-bromo-3-fluoroanisole for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{14}FNO_2$, 271.1; m/z found, 272.10 [M+H]+. $^1$H NMR (500 MHz, CDCl$_3$) δ 8.17 (s, 1H), 7.29-7.22 (m, 1H), 7.13-7.08 (m, 2H), 6.81-6.75 (m, 2H), 3.79 (s, 3H), 3.63-3.58 (m, 2H), 2.30 (s, 3H).

Example 140:
5-(2,6-Difluorophenyl)-7-methyl-indolin-2-one

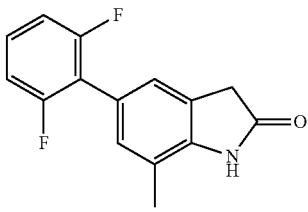 [SMILES: Cc1cc(-c2c(F)cccc2F)cc2c1NC(=O)C2]

The title compound was prepared in a manner analogous to Example 2, substituting 1-bromo-2,6-difluorobenzene for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{11}F_2NO$, 259.1; m/z found, 260.10 [M+H]+. $^1$H NMR (500 MHz, CDCl$_3$) δ 8.33 (s, 1H), 7.29-7.22 (m, 1H), 7.19-7.14 (m, 2H), 7.01-6.93 (m, 2H), 3.64-3.61 (m, 2H), 2.32 (s, 3H).

Example 141: 5-(2-Chloro-6-fluoro-phenyl)-7-methyl-indolin-2-one

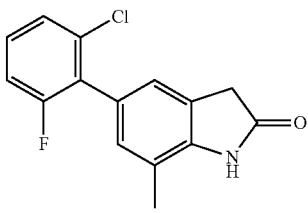 [SMILES: Cc1cc(-c2c(F)cccc2Cl)cc2c1NC(=O)C2]

The title compound was prepared in a manner analogous to Example 2, substituting 2-bromo-1-chloro-3-fluorobenzene for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{11}ClFNO$, 275.1; m/z found, 276.10 [M+H]+. $^1$H NMR (400 MHz, CDCl$_3$) δ 8.43 (s, 1H), 7.31-7.21 (m, 2H), 7.10-7.02 (m, 3H), 3.63 (t, J=1.0 Hz, 2H), 2.33 (s, 3H).

Example 142:
5-(2,6-Dimethylphenyl)-7-methyl-indolin-2-one

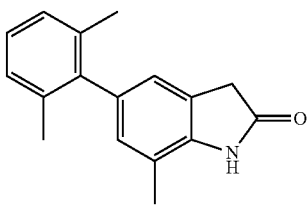 [SMILES: Cc1cc(-c2c(C)cccc2C)cc2c1NC(=O)C2]

The title compound was prepared in a manner analogous to Example 2, substituting 2-bromo-m-xylene for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. The product obtained from flash chromatography was further purified by trituration with EtOAc/hexanes. MS (ESI): mass calcd. for $C_{17}H_{17}NO$, 251.1; m/z found, 252.10 [M+H]+. $^1$H NMR (500 MHz, CDCl$_3$) δ 8.48 (s, 1H), 7.17-7.12 (m, 1H), 7.12-7.08 (m, 2H), 6.86-6.80 (m, 2H), 3.63-3.59 (m, 2H), 2.32-2.28 (m, 3H), 2.04 (s, 6H).

Example 143: 3-Chloro-2-(7-methyl-2-oxoindolin-5-yl)benzonitrile

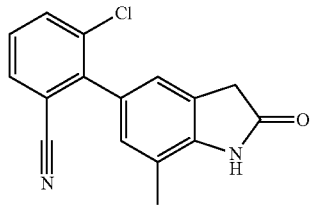 [SMILES: Cc1cc(-c2c(Cl)cccc2C#N)cc2c1NC(=O)C2]

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 2-bromo-3-chlorobenzonitrile for 1-bromo-3-chloro-2-iodobenzene. MS (ESI): mass calcd. for $C_{16}H_{11}ClN_2O$, 282.1; m/z found, 283.0 [M+H]+. $^1$H NMR (500 MHz, DMSO-d$_6$) δ 10.63 (s, 1H), 7.95-7.87 (m, 2H), 7.63-7.53 (m, 1H), 7.08 (d, J=1.8 Hz, 1H), 7.06-7.01 (m, 1H), 3.57 (s, 2H), 2.26 (s, 3H).

Example 144: 5-(3,5-Dichloro-2-(trifluoromethyl)pyridin-4-yl)-7-methylindolin-2-one

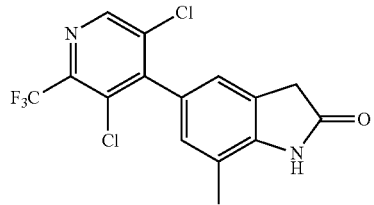 [SMILES: Cc1cc(-c2c(Cl)cnc(C(F)(F)F)c2Cl)cc2c1NC(=O)C2]

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3,5-dichloro-4-iodo-2-(trifluoromethyl)pyridine for 1-bromo-3-chloro-2-iodobenzene. The crude residue was purified by reverse-phase HPLC using XBridge C18 column (5 μm, 100×4.6 mm), mobile phase of 10-100% ACN in 20 mM NH$_4$OH, to afford the title compound (25 mg, 23% yield). MS (ESI): mass calcd. for $C_{15}H_9Cl_2F_3N_2O$, 360.0; m/z found, 360.9 [M+H]+. $^1$H NMR (500 MHz, DMSO-d$_6$) δ 10.65 (s, 1H), 8.89 (s, 1H), 7.05 (d, J=1.6 Hz, 1H), 7.02-6.98 (m, 1H), 3.57 (s, 2H), 2.25 (s, 3H).

Example 145: 5-[3-Chloro-5-(trifluoromethoxy)-4-pyridyl]-7-methyl-indolin-2-one

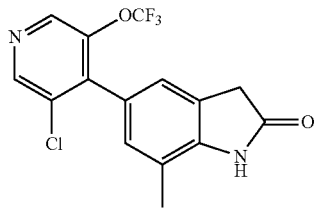

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3-chloro-4-iodo-5-(trifluoromethoxy)pyridine (Intermediate 8) for 1-bromo-3-chloro-2-iodobenzene. MS (ESI): mass calcd. for $C_{15}H_{10}ClF_3N_2O_2$, 342.0; m/z found, 343.0 $[M+H]^+$. $^1$H NMR (400 MHz, DMSO-$d_6$) δ 10.65 (s, 1H), 8.82 (s, 1H), 8.74 (q, J=1.4 Hz, 1H), 7.05 (d, J=1.7 Hz, 1H), 7.04-6.98 (m, 1H), 3.57 (s, 2H), 2.25 (s, 3H).

Example 146: 5-(3-Chloro-5-(difluoromethoxy)pyridin-4-yl)-7-methylindolin-2-one

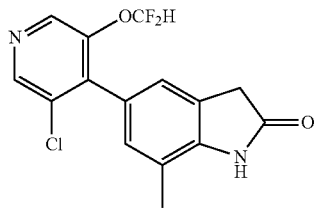

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3-chloro-5-(difluoromethoxy)-4-iodopyridine (Intermediate 9) for 1-bromo-3-chloro-2-iodobenzene. MS (ESI): mass calcd. for $C_{15}H_{11}ClF_2N_2O_2$, 324.0; m/z found, 325.0 $[M+H]^+$. $^1$H NMR (400 MHz, DMSO-$d_6$) δ 10.61 (s, 1H), 8.66 (s, 1H), 8.54 (t, J=1.0 Hz, 1H), 7.21 (t, J=73.0 Hz, 1H), 7.02 (d, J=1.6 Hz, 1H), 7.00-6.95 (m, 1H), 3.55 (s, 2H), 2.24 (s, 3H).

Example 147: 5-(3,5-Dichloro-4-pyridyl)-7-methyl-indolin-2-one

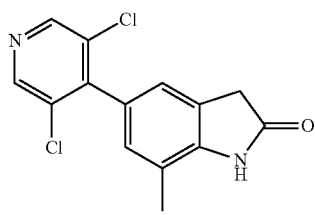 [SMILES: Cc1cc(-c2c(Cl)cncc2Cl)cc2c1NC(=O)C2]

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3,5-dichloro-4-iodopyridine for 1-bromo-3-chloro-2-iodobenzene. The crude product was purified by trituration with DCM to afford the title compound (42 mg, 40% yield). MS (ESI): mass calcd. for $C_{14}H_{10}Cl_2N_2O$, 292.0; m/z found, 294.9 $[M+H]^+$. $^1$H NMR (400 MHz, DMSO-$d_6$) δ 10.62 (s, 1H), 8.71 (s, 2H), 7.01 (d, J=1.8 Hz, 1H), 7.00-6.94 (m, 1H), 3.56 (s, 2H), 2.25 (s, 3H).

Example 148: 5-(3,5-Dimethyl-4-pyridyl)-7-methyl-indolin-2-one

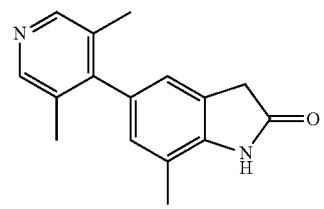 [SMILES: Cc1cc(-c2c(C)cncc2C)cc2c1NC(=O)C2]

The title compound was prepared in a manner analogous to Example 2, substituting 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 4-bromo-3,5-dimethylpyridine hydrochloride for 1-bromo-3-chloro-2-iodobenzene. MS (ESI): mass calcd. for $C_{16}H_{16}N_2O$, 252.1; m/z found, 253.1 $[M+H]^+$. $^1$H NMR (500 MHz, DMSO-$d_6$) δ 10.53 (s, 1H), 8.36-8.22 (m, 2H), 6.85 (d, J=1.7 Hz, 1H), 6.82-6.78 (m, 1H), 3.53 (s, 2H), 2.23 (s, 3H), 2.00 (t, J=0.6 Hz, 6H).

Example 149: 5-(2-Chloro-4-methyl-3-pyridyl)-7-methyl-indolin-2-one

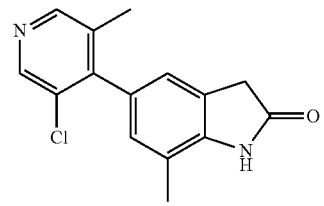 [SMILES: Cc1cc(-c2c(C)cncc2Cl)cc2c1NC(=O)C2]

The title compound was prepared in a manner analogous to Example 2, substituting 3-bromo-2-chloro-4-picoline for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{13}ClN_2O$, 272.1; m/z found, 273.10 $[M+H]^+$. $^1$H NMR (400 MHz, CDCl$_3$) δ 8.66 (s, 1H), 8.24 (d, J=5.0 Hz, 1H), 7.15 (dd, J=4.9, 0.8 Hz, 1H), 6.93-6.86 (m, 2H), 3.71-3.55 (m, 2H), 2.34 (s, 3H), 2.14 (s, 3H).

Example 150: 5-(2-Methoxy-4-methyl-3-pyridyl)-7-methyl-indolin-2-one

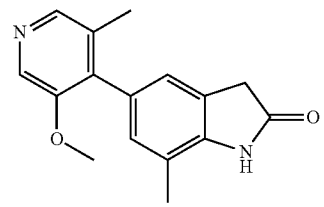 [SMILES: COc1cncc(C)c1-c1cc(C)c2c(c1)CC(=O)N2]

The title compound was prepared in a manner analogous to Example 2, substituting 3-bromo-2-methoxy-4-methyl-pyridine for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{16}N_2O_2$, 268.1; m/z found, 269.10 [M+H]$^+$. $^1$H NMR (400 MHz, CDCl$_3$) δ 8.02 (d, J=5.2 Hz, 1H), 7.70 (s, 1H), 6.95-6.87 (m, 2H), 6.82 (dd, J=5.2, 0.7 Hz, 1H), 3.87 (s, 3H), 3.60 (s, 2H), 2.28 (s, 3H), 2.10 (s, 3H).

Example 151: 5-(2,4-Dimethyl-3-pyridyl)-7-methyl-indolin-2-one

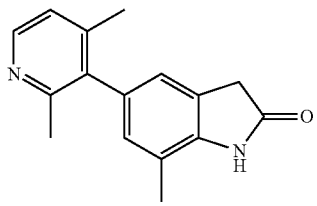 [SMILES: Cc1cc(-c2c(C)ccnc2C)cc2c1NC(=O)C2]

The title compound was prepared in a manner analogous to Example 2, substituting 3-bromo-2,4-dimethylpyridine for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{16}N_2O$, 252.1; m/z found, 253.20 [M+H]$^+$. $^1$H NMR (400 MHz, CDCl$_3$) δ 9.71 (s, 1H), 8.34 (d, J=5.1 Hz, 1H), 7.04 (d, J=5.0 Hz, 1H), 6.88-6.80 (m, 2H), 3.64 (s, 2H), 2.36 (s, 3H), 2.29 (s, 3H), 2.06 (s, 3H).

Example 152: 5-(2,4-Dichloro-3-pyridyl)-7-methyl-indolin-2-one

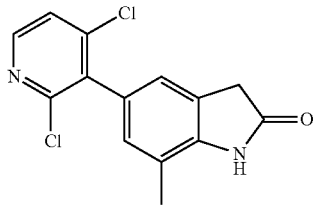 [SMILES: Cc1cc(-c2c(Cl)ccnc2Cl)cc2c1NC(=O)C2]

The title compound was prepared in a manner analogous to Example 2, substituting 3-bromo-2,4-dichloropyridine for 1-bromo-3-chloro-2-iodobenzene and 7-methyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{14}H_{10}Cl_2N_2O$, 292.0; m/z found, 293.10 [M+H]$^+$. $^1$H NMR (400 MHz, CDCl$_3$) δ 9.87 (s, 1H), 8.28 (d, J=5.3 Hz, 1H), 7.40 (d, J=5.3 Hz, 1H), 7.02-6.93 (m, 2H), 3.64 (s, 2H), 2.39 (s, 3H).

Example 153: 7-Chloro-5-[2-chloro-6-(trifluoromethoxy)phenyl]indolin-2-one

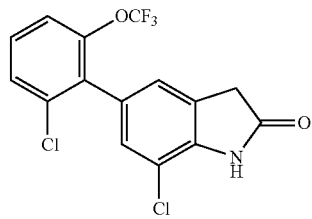 [SMILES: O=C1Cc2cc(-c3c(Cl)cccc3OC(F)(F)F)cc(Cl)c2N1]

The title compound was prepared in a manner analogous to Example 2, substituting 7-chloro-5-(4,4,5,5-tetramethyl-1,3,2-dioxaborolan-2-yl)indolin-2-one (Intermediate 10) for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. MS (ESI): mass calcd. for $C_{15}H_8Cl_2F_3NO_2$, 361.0; m/z found, 362.0 [M+H]$^+$. $^1$H NMR (400 MHz, DMSO-d$_6$) δ 10.96 (s, 1H), 7.67-7.64 (m, 1H), 7.56 (t, J=8.2 Hz, 1H), 7.51-7.48 (m, 1H), 7.18 (d, J=1.4 Hz, 1H), 7.14-7.08 (m, 1H), 3.68 (t, J=1.1 Hz, 2H).

Example 154: 7-Chloro-5-[2-chloro-6-(difluoromethoxy)phenyl]indolin-2-one

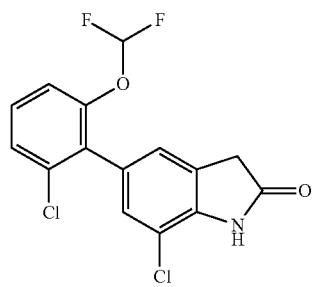 [SMILES: O=C1Cc2cc(-c3c(Cl)cccc3OC(F)F)cc(Cl)c2N1]

The title compound was prepared in a manner analogous to Example 118, substituting 7-chloro-5-(4,4,5,5-tetramethyl-1,3,2-dioxaborolan-2-yl)indolin-2-one for 7-fluoro-5-(4,4,5,5-tetramethyl-1,3,2-dioxaborolan-2-yl)indolin-2-one in Step B. MS (ESI): mass calcd. for $C_{15}H_9Cl_2F_2NO_2$, 343.0; m/z found, 344.0 [M+H]$^+$. $^1$H NMR (500 MHz, DMSO-d$_6$) δ 10.91 (s, 1H), 7.50-7.46 (m, 2H), 7.32-7.27 (m, 1H), 7.17-7.15 (m, 1H), 7.14 (s, 1H), 7.09-7.07 (m, 1H), 3.66 (s, 2H).

Example 155: 2-[3-Chloro-2-(7-chloro-2-oxo-indolin-5-yl)phenyl]-2-methyl-propanenitrile

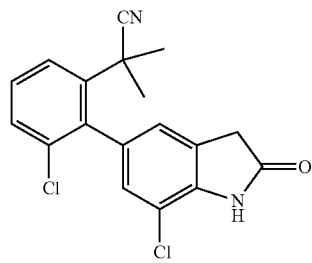 [SMILES: CC(C)(C#N)c1cccc(Cl)c1-c1cc(Cl)c2c(c1)CC(=O)N2]

The title compound was prepared in a manner analogous to Example 81 substituting 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one in Step B. MS (ESI): mass calcd. for $C_{18}H_{14}Cl_2N_2O$, 344.0; m/z found, 347.1 [M+H]$^+$. $^1$H NMR (400 MHz, DMSO-d$_6$) δ 10.94 (s, 1H), 7.65-7.55 (m, 2H), 7.50-7.45 (m, 1H), 7.15-7.14 (m, 1H), 7.07 (d, J=1.6 Hz, 1H), 3.73-3.55 (m, 2H), 1.63 (s, 3H), 1.58 (s, 3H).

Example 156: 4-Chloro-3-(7-chloro-2-oxo-indolin-5-yl)-2-(trifluoromethoxy)benzonitrile

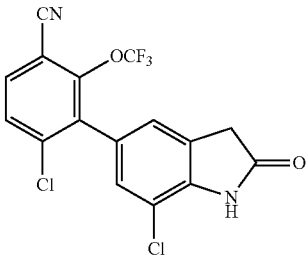 [SMILES: N#Cc1ccc(Cl)c(-c2cc(Cl)c3c(c2)CC(=O)N3)c1OC(F)(F)F]

The title compound was prepared in a manner analogous to Example 2, substituting 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 4-chloro-3-iodo-2-(trifluoromethoxy)benzonitrile for 1-bromo-3-chloro-2-iodobenzene. MS (ESI): mass calcd. for $C_{16}H_7Cl_2F_3N_2O_2$, 386.0; m/z found, 387.0 [M+H]$^+$. $^1$H NMR (600 MHz, DMSO-d$_6$) δ 11.03 (s, 1H), 8.14 (d, J=8.5 Hz, 1H), 7.94 (d, J=8.5 Hz, 1H), 7.35 (d, J=1.5 Hz, 1H), 7.28-7.16 (m, 1H), 3.69 (q, J=1.1 Hz, 2H).

Example 157: 7-Chloro-5-(3-chloro-5-(trifluoromethoxy)pyridin-4-yl)indolin-2-one

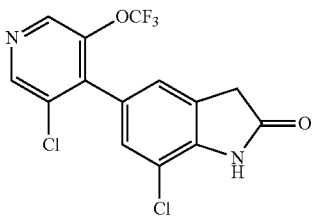 [SMILES: O=C1Cc2cc(-c3c(Cl)cncc3OC(F)(F)F)cc(Cl)c2N1]

The title compound was prepared in a manner analogous to Example 2, substituting 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3-chloro-4-iodo-5-(trifluoromethoxy)pyridine for 1-bromo-3-chloro-2-iodobenzene. MS (ESI): mass calcd. for $C_{14}H_7Cl_2F_3N_2O_2$, 361.9; m/z found, 363.0 [M+H]$^+$. $^1$H NMR (400 MHz, DMSO-d$_6$) δ 11.03 (s, 1H), 8.85 (s, 1H), 8.77 (q, J=1.4 Hz, 1H), 7.37-7.32 (m, 1H), 7.25-7.19 (m, 1H), 3.69 (s, 2H).

Example 158: 7-Chloro-5-[3-chloro-5-(difluoromethoxy)-4-pyridyl]indolin-2-one

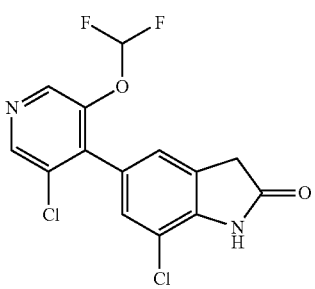 [SMILES: O=C1Cc2cc(-c3c(Cl)cncc3OC(F)F)cc(Cl)c2N1]

The title compound was prepared in a manner analogous to Example 2, substituting 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3-chloro-4-iodo-5-(difluoromethoxy)pyridine for 1-bromo-3-chloro-2-iodobenzene. MS (ESI): mass calcd. for $C_{14}H_8Cl_2F_2N_2O_2$, 344.0; m/z found, 345.0 [M+H]$^+$. $^1$H NMR (400 MHz, DMSO-d$_6$) δ 11.00 (s, 1H), 8.70 (s, 1H), 8.57 (s, 1H), 7.31-7.29 (m, 1H), 7.24 (t, J=72.8 Hz, 1H), 7.19 (d, J=1.4 Hz, 1H), 3.69 (s, 2H).

Example 159: 7-Chloro-5-(3,5-dichloro-4-pyridyl)indolin-2-one

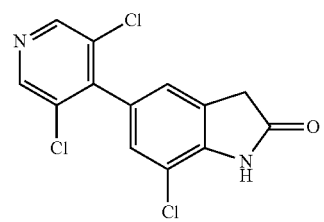 [SMILES: O=C1Cc2cc(-c3c(Cl)cncc3Cl)cc(Cl)c2N1]

The title compound was prepared in a manner analogous to Example 2, substituting 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3,5-dichloro-4-iodopyridine for 1-bromo-3-chloro-2-iodobenzene. The crude product was purified by trituration with DCM to afford the title compound (44 mg, 42% yield). MS (ESI): mass calcd. for $C_{13}H_7Cl_3N_2O$, 312.0; m/z found, 314.0 [M+H]$^+$. $^1$H NMR (500 MHz, DMSO-d$_6$) δ 11.01 (s, 1H), 8.74 (s, 2H), 7.31 (d, J=1.6 Hz, 1H), 7.18 (d, J=1.6 Hz, 1H), 3.69 (s, 2H).

Example 160: 7-Chloro-5-(2-chloro-4-methyl-3-pyridyl)indolin-2-one

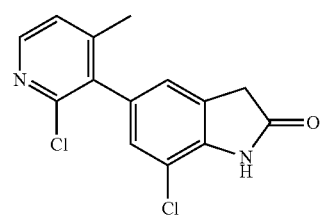 [SMILES: Cc1ccnc(Cl)c1-c1cc(Cl)c2c(c1)CC(=O)N2]

The title compound was prepared in a manner analogous to Example 2, substituting 3-bromo-2-chloro-4-picoline for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one.
MS (ESI): mass calcd. for $C_{14}H_{10}Cl_2N_2O$, 292.0; m/z found, 293.10 [M+H]$^+$. $^1$H NMR (500 MHz, DMSO-d$_6$) δ 10.92 (s, 1H), 8.27 (d, J=4.9 Hz, 1H), 7.39 (dd, J=5.0, 0.8 Hz, 1H), 7.19 (d, J=1.5 Hz, 1H), 7.09 (q, J=1.2 Hz, 1H), 3.73-3.60 (m, 2H), 2.11 (s, 3H).

Example 161: 7-Chloro-5-(2,4-dimethyl-3-pyridyl)indolin-2-one

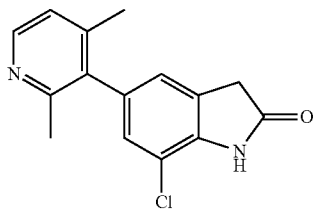 [SMILES: Cc1ccnc(C)c1-c1cc(Cl)c2c(c1)CC(=O)N2]

The title compound was prepared in a manner analogous to Example 2, substituting 3-bromo-2,4-dimethylpyridine for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{13}ClN_2O$, 272.1; m/z found, 273.15 [M+H]. $^1$H NMR (400 MHz, $CDCl_3$) δ 9.28 (s, 1H), 8.37 (d, J=5.1 Hz, 1H), 7.08-7.02 (m, 2H), 6.94 (q, J=1.3 Hz, 1H), 3.71 (d, J=1.1 Hz, 2H), 2.31 (s, 3H), 2.07 (s, 3H).

Example 162: 7-Chloro-5-(2-methoxy-4-methyl-3-pyridyl)indolin-2-one

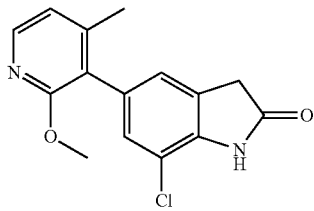 [SMILES: COc1nccc(C)c1-c1cc(Cl)c2c(c1)CC(=O)N2]

The title compound was prepared in a manner analogous to Example 2, substituting 3-bromo-2-methoxy-4-methylpyridine for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{13}ClN_2O_2$, 288.1; m/z found, 289.10 [M+H]$^+$. $^1$H NMR (400 MHz, $CDCl_3$) δ 8.39 (s, 1H), 8.03 (d, J=5.2 Hz, 1H), 7.10-7.07 (m, 1H), 7.01-6.97 (m, 1H), 6.82 (dd, J=5.2, 0.7 Hz, 1H), 3.87 (s, 3H), 3.68 (s, 2H), 2.11 (s, 3H).

Example 163: 7-Chloro-5-(2,4-dichloro-3-pyridyl)indolin-2-one

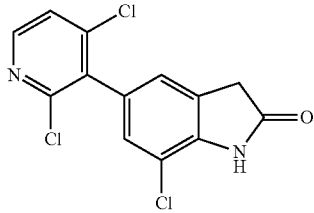 [SMILES: O=C1Cc2cc(-c3c(Cl)ccnc3Cl)cc(Cl)c2N1]

The title compound was prepared in a manner analogous to Example 2, substituting 3-bromo-2,4-dichloropyridine for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{13}H_7Cl_3N_2O$, 312.0; m/z found, 313.00 [M+H]$^+$. $^1$H NMR (400 MHz, $CDCl_3$) δ 8.71 (s, 1H), 8.31 (d, J=5.3 Hz, 1H), 7.41 (d, J=5.3 Hz, 1H), 7.19-7.15 (m, 1H), 7.08-7.03 (m, 1H), 3.75-3.66 (m, 2H).

Example 164: 2-(7-Chloro-2-oxo-indolin-5-yl)-3-methyl-benzonitrile

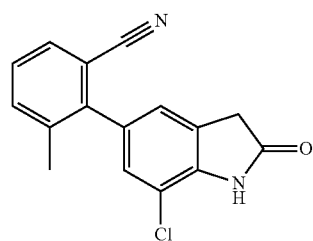 [SMILES: Cc1cccc(C#N)c1-c1cc(Cl)c2c(c1)CC(=O)N2]

The title compound was prepared in a manner analogous to Example 2, substituting 2-bromo-3-methylbenzonitrile for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{11}ClN_2O$, 282.1; m/z found, 283.10 [M+H]$^+$. $^1$H NMR (400 MHz, $CDCl_3$) δ 8.81 (s, 1H), 7.61-7.56 (m, 1H), 7.53-7.48 (m, 1H), 7.36 (t, J=7.7 Hz, 1H), 7.18-7.13 (m, 1H), 7.09-7.04 (m, 1H), 3.71 (d, J=5.9 Hz, 2H), 2.20 (s, 3H).

Example 165: 7-Chloro-5-(2-chloro-6-methyl-phenyl)indolin-2-one

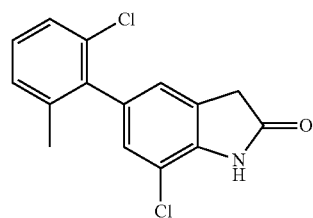 [SMILES: Cc1cccc(Cl)c1-c1cc(Cl)c2c(c1)CC(=O)N2]

The title compound was prepared in a manner analogous to Example 2, substituting 3-chloro-2-iodotoluene for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{11}Cl_2NO$, 291.0; m/z found, 292.10 [M+H]$^+$. $^1$H NMR (400 MHz, $CDCl_3$) δ 8.79 (s, 1H), 7.32-7.29 (m, 1H), 7.22-7.15 (m, 2H), 7.07 (dt, J=1.4, 0.8 Hz, 1H), 6.99-6.93 (m, 1H), 3.77-3.62 (m, 2H), 2.11 (s, 3H).

Example 166: 7-Chloro-5-(2-fluoro-6-methyl-phenyl)indolin-2-one

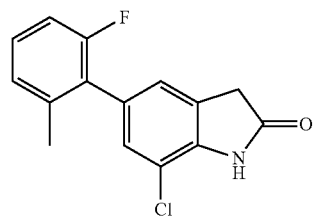 [SMILES: Cc1cccc(F)c1-c1cc(Cl)c2c(c1)CC(=O)N2]

The title compound was prepared in a manner analogous to Example 2, substituting 2-bromo-3-fluorotoluene for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{15}H_{11}ClFNO$, 275.1; m/z found, 276.15 [M+H]$^+$. $^1$H NMR (400 MHz, CDCl$_3$) δ 9.02 (s, 1H), 7.25-7.17 (m, 1H), 7.14 (dd, J=1.5, 0.7 Hz, 1H), 7.07-7.03 (m, 2H), 6.99-6.93 (m, 1H), 3.72-3.67 (m, 2H), 2.18 (s, 3H).

Example 167: 7-Chloro-5-[2-methyl-6-(trifluoromethyl)phenyl]indolin-2-one

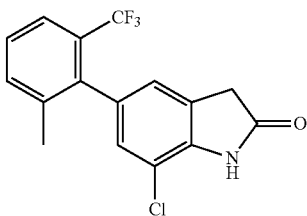 [SMILES: Cc1cccc(C(F)(F)F)c1-c1cc(Cl)c2c(c1)CC(=O)N2]

The title compound was prepared in a manner analogous to Example 2, substituting 2-bromo-3-methylbenzotrifluoride for 1-bromo-3-chloro-2-iodobenzene and 7-chloro-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{16}H_{11}ClF_3NO$, 325.0; m/z found, 326.10 [M+H]$^+$. $^1$H NMR (400 MHz, CDCl$_3$) δ 8.27 (s, 1H), 7.61-7.56 (m, 1H), 7.48-7.42 (m, 1H), 7.40-7.34 (m, 1H), 7.06-7.02 (m, 1H), 6.96-6.92 (m, 1H), 3.70-3.65 (m, 2H), 2.06 (s, 3H).

Example 168: 5-[2-Chloro-6-(trifluoromethoxy)phenyl]-7-ethyl-indolin-2-one

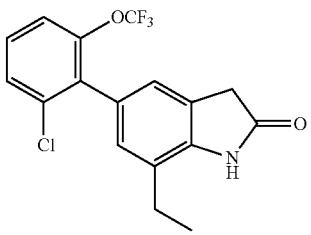 [SMILES: CCc1cc(-c2c(Cl)cccc2OC(F)(F)F)cc2c1NC(=O)C2]

The title compound was prepared in a manner analogous to Example 2, substituting 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. MS (ESI): mass calcd. for $C_{17}H_{13}ClF_3NO_2$, 355.1; m/z found, 356.0 [M+H]$^+$. $^1$H NMR (500 MHz, DMSO-d$_6$) δ 10.59 (s, 1H), 7.64-7.61 (m, 1H), 7.52 (t, J=8.2 Hz, 1H), 7.49-7.44 (m, 1H), 6.95 (d, J=1.7 Hz, 1H), 6.92-6.89 (m, 1H), 3.54 (t, J=0.9 Hz, 2H), 2.60 (q, J=7.5 Hz, 2H), 1.12 (t, J=7.5 Hz, 3H).

Example 169: 2-(7-Ethyl-2-oxo-indolin-5-yl)-3-methyl-benzonitrile

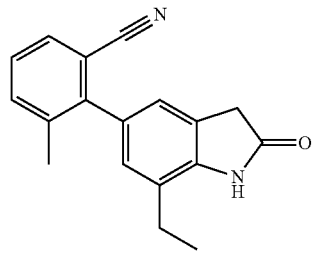 [SMILES: CCc1cc(-c2c(C)cccc2C#N)cc2c1NC(=O)C2]

The title compound was prepared in a manner analogous to Example 2, substituting 2-bromo-3-methylbenzonitrile for 1-bromo-3-chloro-2-iodobenzene and 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{18}H_{16}N_2O$, 276.1; m/z found, 277.20 [M+H]$^+$. $^1$H NMR (400 MHz, CDCl$_3$) δ 9.28 (s, 1H), 7.57 (ddd, J=7.7, 1.2, 0.7 Hz, 1H), 7.48 (ddd, J=7.8, 1.4, 0.8 Hz, 1H), 7.33 (t, J=7.7 Hz, 1H), 7.04-6.97 (m, 2H), 3.64 (d, J=5.0 Hz, 2H), 2.69 (q, J=7.6 Hz, 2H), 2.21 (s, 3H), 1.30 (t, J=7.6 Hz, 3H).

Example 170: 5-(2-Chloro-6-methyl-phenyl)-7-ethyl-indolin-2-one

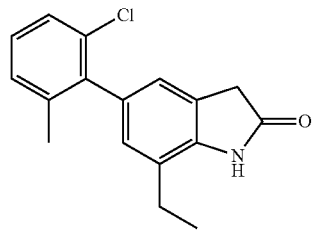 [SMILES: CCc1cc(-c2c(C)cccc2Cl)cc2c1NC(=O)C2]

The title compound was prepared in a manner analogous to Example 2, substituting 3-chloro-2-iodotoluene for 1-bromo-3-chloro-2-iodobenzene and 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{17}H_{16}ClNO$, 285.1; m/z found, 286.20 [M+H]$^+$. $^1$H NMR (400 MHz, CDCl$_3$) δ 8.58 (s, 1H), 7.34-7.28 (m, 1H), 7.19-7.12 (m, 2H), 6.94-6.87 (m, 2H), 3.65-3.59 (m, 2H), 2.65 (q, J=7.6 Hz, 2H), 2.10 (s, 3H), 1.28 (t, J=7.6 Hz, 3H).

Example 171: 7-Ethyl-5-(2-fluoro-6-methyl-phenyl)indolin-2-one

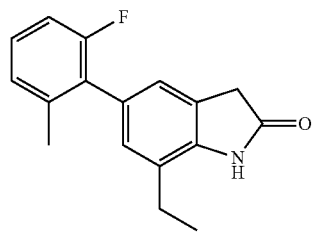 [SMILES: CCc1cc(-c2c(C)cccc2F)cc2c1NC(=O)C2]

The title compound was prepared in a manner analogous to Example 2, substituting 2-bromo-3-fluorotoluene for 1-bromo-3-chloro-2-iodobenzene and 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{17}H_{16}FNO$, 269.1; m/z found, 270.15 [M+H]$^+$. $^1$H NMR (400 MHz, CDCl$_3$) δ 8.99 (s, 1H), 7.24-7.15 (m, 1H), 7.11-7.03 (m, 1H), 7.02-6.92 (m, 3H), 3.67-3.59 (m, 2H), 2.66 (q, J=7.7 Hz, 2H), 2.18 (s, 3H), 1.33-1.23 (m, 3H).

Example 172: 7-Ethyl-5-[2-methyl-6-(trifluoromethyl)phenyl]indolin-2-one

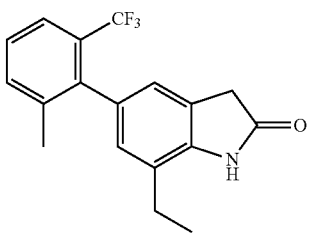 [SMILES: CCc1cc(-c2c(C)cccc2C(F)(F)F)cc2c1NC(=O)C2]

The title compound was prepared in a manner analogous to Example 2, substituting 2-bromo-3-methylbenzotrifluoride for 1-bromo-3-chloro-2-iodobenzene and 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{18}H_{16}F_3NO$, 319.1; m/z found, 320.10 [M+H]$^+$. $^1$H NMR (500 MHz, CDCl$_3$) δ 8.83 (s, 1H), 7.58 (dd, J=6.8, 1.2 Hz, 1H), 7.46-7.42 (m, 1H), 7.38-7.32 (m, 1H), 6.90-6.85 (m, 2H), 3.68-3.54 (m, 2H), 2.64 (q, J=7.6 Hz, 2H), 2.05 (s, 3H), 1.26 (t, J=7.5 Hz, 3H).

Example 173: 5-(3,5-Eimethyl-4-pyridyl)-7-ethyl-indolin-2-one

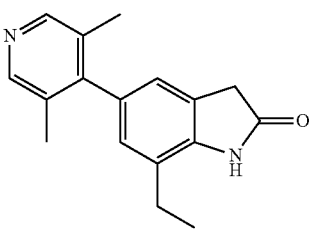 [SMILES: CCc1cc(-c2c(C)cncc2C)cc2c1NC(=O)C2]

The title compound was prepared in a manner analogous to Example 2, substituting 4-bromo-3,5-dimethylpyridine hydrochloride for 1-bromo-3-chloro-2-iodobenzene and 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one. MS (ESI): mass calcd. for $C_{17}H_{18}N_2O$, 266.1; m/z found, 267.20 [M+H]$^+$. $^1$H NMR (400 MHz, CDCl$_3$) δ 8.51 (s, 1H), 8.37-8.31 (m, 2H), 6.86-6.78 (m, 2H), 3.62 (s, 2H), 2.64 (q, J=7.6 Hz, 2H), 2.05 (s, 6H), 1.32-1.21 (m, 3H).

Example 174: 5-(3,5-Dichloro-4-pyridyl)-7-ethyl-indolin-2-one

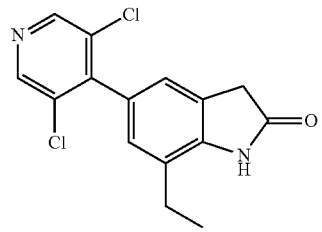 [SMILES: CCc1cc(-c2c(Cl)cncc2Cl)cc2c1NC(=O)C2]

The title compound was prepared in a manner analogous to Example 2, substituting 7-ethyl-5-(4,4,5,5-tetramethyl-1,3,2-dioxaborolan-2-yl)indolin-2-one for 5-(4,4,5,5-tetramethyl-1,3,2-dioxaborolan-2-yl)indolin-2-one and 3,5-dichloro-4-iodopyridine for 1-bromo-3-chloro-2-iodobenzene. MS (ESI): mass calcd. for $C_{15}H_{12}Cl_{12}N_2O$, 306.0; m/z found, 309.1 [M+H]$^+$. $^1$H NMR (500 MHz, DMSO-d$_6$) δ 10.65 (s, 1H), 8.71 (s, 2H), 7.03 (d, J=1.7 Hz, 1H), 7.00 (d, J=1.6 Hz, 1H), 3.56 (s, 2H), 2.50 (dt, J=3.7, 1.8 Hz, 2H), 1.14 (t, J=7.5 Hz, 3H).

Example 175: 5-[2-Chloro-6-(trifluoromethoxy)phenyl]-2-oxo-indoline-7-carbonitrile

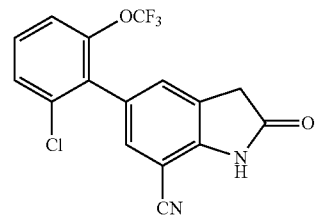 [SMILES: N#Cc1cc(-c2c(Cl)cccc2OC(F)(F)F)cc2c1NC(=O)C2]

The title compound was prepared in a manner analogous to Example 2, substituting 2-oxo-5-(4,4,5,5-tetramethyl-1,3,2-dioxaborolan-2-yl)indoline-7-carbonitrile for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. MS (ESI): mass calcd. for $C_{16}H_8ClF_3N_2O_2$, 352.0; m/z found, 353.9 [M+H]$^+$. $^1$H NMR (500 MHz, DMSO-d$_6$) δ 11.51 (s, 1H), 7.69-7.66 (m, 1H), 7.58 (t, J=8.2 Hz, 1H), 7.54 (d, J=1.7 Hz, 1H), 7.53-7.50 (m, 1H), 7.47-7.42 (m, 1H), 3.67 (s, 2H).

Example 176: 5-[2-Chloro-6-(trifluoromethoxy)phenyl]-7-(trifluoromethyl)indolin-2-one

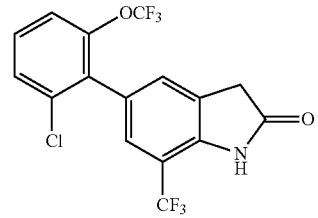 [SMILES: O=C1Cc2cc(-c3c(Cl)cccc3OC(F)(F)F)cc(C(F)(F)F)c2N1]

The title compound was prepared in a manner analogous to Example 2 substituting 5-(4,4,5,5-tetramethyl-1,3,2-dioxaborolan-2-yl)-7-(trifluoromethyl)indolin-2-one for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. MS (ESI): mass calcd. for $C_{16}H_8ClF_6NO_2$, 395.0; m/z found, 395.80 [M+H]$^+$. $^1$H NMR (500 MHz, DMSO-d$_6$) δ 11.04 (s, 1H), 7.69-7.65 (m, 1H), 7.58 (t, J=8.2 Hz, 1H), 7.54-7.49 (m, 1H), 7.44 (d, J=1.4 Hz, 1H), 7.38-7.33 (m, 1H), 3.67 (s, 2H).

Example 177: 5-[2-Chloro-6-(trifluoromethoxy)phenyl]-7-(trifluoromethoxy)indolin-2-one

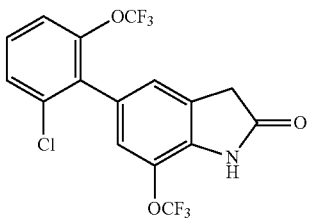 [SMILES: O=C1Cc2cc(-c3c(Cl)cccc3OC(F)(F)F)cc(OC(F)(F)F)c2N1]

The title compound was prepared in a manner analogous to Example 2, substituting 5-(4,4,5,5-tetramethyl-1,3,2-dioxaborolan-2-yl)-7-(trifluoromethyl)indolin-2-one for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. MS (ESI): mass calcd. for $C_{16}H_8ClF_6NO_3$, 411.0; m/z found, 411.80 [M+H]$^+$. $^1$H NMR (500 MHz, DMSO-d$_6$) δ 11.22 (s, 1H), 7.68-7.64 (m, 1H), 7.57 (t, J=8.2 Hz, 1H), 7.52-7.49 (m, 1H), 7.22-7.19 (m, 1H), 7.15 (s, 1H), 3.68 (s, 2H).

Example 178: 5-[2-Chloro-6-(trifluoromethoxy)phenyl]-7-methoxy-indolin-2-one

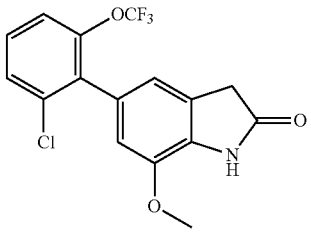 [SMILES: COc1cc(-c2c(Cl)cccc2OC(F)(F)F)cc2c1NC(=O)C2]

The title compound was prepared in a manner analogous to Example 2, substituting 5-(4,4,5,5-tetramethyl-1,3,2-dioxaborolan-2-yl)-7-(methoxyl)indolin-2-one for 5-(4,4,5,5-tetramethyl-1,3,2-dioxaborolan-2-yl)indolin-2-one and 1-chloro-2-iodo-3-(trifluoromethoxy)benzene for 1-bromo-3-chloro-2-iodobenzene. MS (ESI): mass calcd. for $C_{16}H_{11}ClF_3NO_3$, 357.0; m/z found, 358.0 [M+H]$^+$. $^1$H NMR (400 MHz, DMSO-d$_6$) δ 10.55 (s, 1H), 7.65-7.62 (m, 1H), 7.53 (t, J=8.1 Hz, 1H), 7.50-7.46 (m, 1H), 6.80 (d, J=1.4 Hz, 1H), 6.75 (d, J=1.4 Hz, 1H), 3.79 (s, 3H), 3.55 (s, 2H).

Example 179: 5-[2-Chloro-3-(4-methoxy-1-piperidyl)phenyl]indolin-2-one

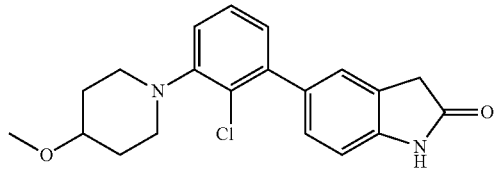 [SMILES: COC1CCN(c2cccc(-c3ccc4c(c3)CC(=O)N4)c2Cl)CC1]

Step A: 1-(3-Bromo-2-chlorophenyl)-4-methoxypiperidine

A solution of 1,3-dibromo-2-chlorobenzene (300 mg, 1.1 mmol), 4-methoxypiperidine hydrochloride (168 mg, 1.1 mmol), sodium tert-butoxide (160 mg, 1.7 mmol), BINAP (35 mg, 0.05 mmol), and Pd$_2$(dba)$_3$ (20 mg, 0.02 mmol) in toluene (3.0 mL) was degassed with nitrogen for 10 minutes. The reaction mixture was heated at 140° C. in microwave for 1 h. After cooling to rt, water was added and the aqueous layer was extracted with EtOAc (×2). The combined organic extracts were dried over Na$_2$SO$_4$ and concentrated in vacuo. Purification (FCC, SiO$_2$; 0-50% EtOAc/hexanes) provided the title compound as an oil (168 mg, 50% yield). $^1$H NMR (400 MHz, DMSO-d$_6$) δ 7.42 (dd, J=7.7, 1.7 Hz, 1H), 7.28-7.14 (m, 2H), 3.39-3.33 (m, 1H), 3.28 (s, 3H), 3.14 (dt, J=10.5, 4.5 Hz, 2H), 2.77 (ddd, J=12.0, 9.2, 3.0 Hz, 2H), 2.04-1.91 (m, 2H), 1.61 (dtd, J=12.2, 8.8, 3.4 Hz, 2H).

Step B: 5-(2-Chloro-3-(4-methoxypiperidin-1-yl)phenyl)indolin-2-one

The title compound was prepared in a manner analogous to Example 2, substituting 1-(3-bromo-2-chlorophenyl)-4-methoxypiperidine for 1-bromo-3-chloro-2-iodobenzene. MS (ESI): mass calcd. for $C_{20}H_{21}ClN_2O_2$, 356.1; m/z found, [M+H]=357.8 [M+H]$^+$. $^1$H NMR (500 MHz, DMSO-d$_6$) δ 10.45 (s, 1H), 7.30 (t, J=7.8 Hz, 1H), 7.24-7.12 (m, 3H), 6.98 (dd, J=7.6, 1.5 Hz, 1H), 6.87 (dd, J=8.0, 0.6 Hz, 1H), 3.51 (s, 2H), 3.37-3.34 (m, 1H), 3.28 (s, 3H), 3.22-3.13 (m, 2H), 2.79 (ddd, J=11.7, 9.1, 2.9 Hz, 2H), 2.02-1.92 (m, 2H), 1.61 (qd, J=11.7, 10.3, 3.3 Hz, 2H).

Examples 180-184 are prophetic compounds and may be prepared in a manner analogous to Example 2.

Example 180: 2-Chloro-3-(7-methyl-2-oxoindolin-5-yl)-4-(trifluoromethoxy)benzonitrile

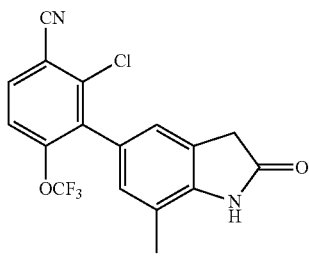 [SMILES: Cc1cc(-c2c(OC(F)(F)F)ccc(C#N)c2Cl)cc2c1NC(=O)C2]

Predicted Chemical Formula: $C_{17}H_{10}ClF_3N_2O_2$, Exact Mass: 366.04. The title compound may be made in a manner analogous to Example 2 using Intermediate 3 and Intermediate 5.

Example 181: 2-Chloro-3-(7-chloro-2-oxoindolin-5-yl)-4-(trifluoromethoxy)benzonitrile

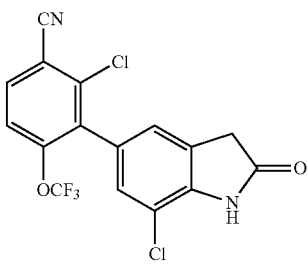

Predicted Chemical Formula: $C_{16}H_7Cl_2F_3N_2O_2$, Exact Mass: 385.98. The title compound may be made in a manner analogous to Example 2 using Intermediate 3 and Intermediate 10

Example 182: 7-Chloro-5-(3,5-dimethylpyridin-4-yl)indolin-2-one

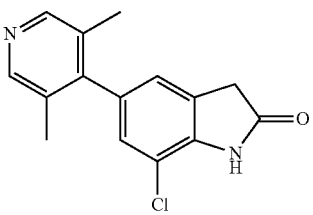 [SMILES: Cc1cncc(C)c1-c1cc(Cl)c2c(c1)CC(=O)N2]

Predicted Chemical Formula: $C_{15}H_{13}ClN_2O$, Exact Mass: 272.07. The title compound may be made in a manner analogous to Example 2 using Intermediate 10.

Example 183: 7-Chloro-5-(4-chloro-2-methoxypyridin-3-yl)indolin-2-one

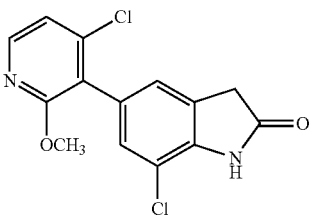 [SMILES: COc1nccc(Cl)c1-c1cc(Cl)c2c(c1)CC(=O)N2]

Predicted Chemical Formula: $C_{14}H_{10}Cl_2N_2O_2$, Exact Mass: 308.01. The title compound may be made in a manner analogous to Example 2 using 3-bromo-4-chloro-2-methoxypyridine and Intermediate 10.

Example 184: 7-Methyl-5-(4-chloro-2-methoxypyridin-3-yl)indolin-2-one

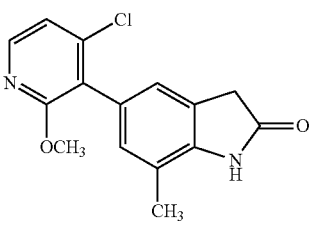 [SMILES: COc1nccc(Cl)c1-c1cc(C)c2c(c1)CC(=O)N2]

Predicted Chemical Formula: $C_{15}H_{13}ClN_2O_2$, Exact Mass: 288.07. The title compound may be made in a manner analogous to Example 2 using 3-bromo-4-chloro-2-methoxypyridine and Intermediate 5.

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." *Comb Chem High Throughput Screen* 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." *Neuron* 55(6): 890-904).

An in vitro assay was used to determine the potency of test compounds as inhibitors of the glutamate response of the channel formed by GluA1o-γ8. To ensure a 1:1 stoichiometry of GluA1o and γ8 subunits in the expressed channel, a fusion of the cDNAs for GRIA1o and CACNG8 was used. Following Shi et al (2009) "The stoichiometry of AMPA receptors and TARPs varies by neuronal cell type." *Neuron* 62(5): 633-640), the C-terminus of the cDNA for GRIA1o was fused to the N-terminus of the cDNA for γ8. The linker sequence was QQQQQQQQQQEFAT. Channels expressed with this construct appear to have similar properties to channels formed by co-expression of GRIA1o with an excess of CACNG8 (Shi et al. 2009). A clonal cell line in HEK293 cells stably expressing this construct, with a geneticin selection marker, was generated for use in this assay. Cell expressing the GRIA1o-CACNG8 fusion construct were grown in a monolayer in 96- or 384-well microtiter plates. They were washed with assay buffer (135 mM NaCl, 4 mM KCl, 3 mM $CaCl_2$, 1 mM $MgCl_2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 μM glutamate was monitored using a Molecular Devices FLIPR Tetra.

The fluorescence in each well was normalized to the fluorescence of negative and positive control wells. The negative control wells had no added compounds, and the positive control wells had been incubated with 10 μM CP465022 (a non-subtype-selective AMPA receptor antagonist) (Lazzaro et al. (2002). "Functional characterization of CP-465,022, a selective, noncompetitive AMPA receptor antagonist." Neuropharmacology 42(2): 143-153). The responses to glutamate as functions of the test compound concentrations were fitted to a four-parameter logistic function. The fitted parameter corresponding to the midpoint was taken to be the potency of inhibition of the compound. The data in Table 4 below illustrates the observed potentcy for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 4

| Example | Compound name | GluR1-γ8 pIC$_{50}$ |
|---|---|---|
| 1 | 5-(2,6-Dimethylphenyl)indolin-2-one; | 6.4 |
| 2 | 5-(2-Bromo-6-chloro-phenyl)indolin-2-one; | 7.6 |
| 3 | 5-(2-Chloro-6-methyl-phenyl)indolin-2-one; | 7.0 |
| 4 | 5-(2,6-Dichlorophenyl)indolin-2-one; | 7.5 |
| 5 | 5-[2-Chloro-6-(trifluoromethoxy)phenyl]indolin-2-one; | 7.8 |
| 6 | 2-[3-Chloro-2-(2-oxoindolin-5-yl)phenyl]acetonitrile; | 7.5 |
| 81 | 2-[3-Chloro-2-(2-oxoindolin-5-yl)phenyl]-2-methyl-propanenitrile; | 7.1 |
| 115 | 4-Chloro-3-(2-oxoindolin-5-yl)-2-(trifluoromethoxy)benzonitrile; | 7.9 |
| 117 | 5-[2-Chloro-6-(trifluoromethoxy)phenyl]-7-fluoro-indolin-2-one; | 8.5 |
| 118 | 5-[2-Chloro-6-(difluoromethoxy)phenyl]-7-fluoro-indolin-2-one; | 7.8 |
| 119 | 2-[3-Chloro-2-(7-fluoro-2-oxo-indolin-5-yl)phenyl]-2-methyl-propanenitrile; | 7.6 |
| 121 | 5-[2-Chloro-3-(4-methoxy-1-piperidyl)phenyl]-7-fluoro-indolin-2-one; | <5 |
| 122 | 5-[2-(Difluoromethoxy)-6-methyl-phenyl]-7-fluoro-indolin-2-one; | 4.8 |
| 123 | 5-[2-(Difluoromethoxy)-6-methoxy-phenyl]-7-fluoro-indolin-2-one; | <5 |
| 124 | 2-Chloro-3-(7-fluoro-2-oxo-indolin-5-yl)-4-(trifluoromethoxy)benzonitrile; | 7.9 |
| 125 | 5-(3,5-Dimethyl-4-pyridyl)-7-fluoro-indolin-2-one; | 6.6 |
| 126 | 5-(3,5-Dichloro-4-pyridyl)-7-fluoro-indolin-2-one; | 6.5 |
| 127 | 5-[2-Chloro-6-(trifluoromethoxy)phenyl]-7-methyl-indolin-2-one; | 9.7 |
| 128 | 5-[2-Chloro-6-(difluoromethoxy)phenyl]-7-methyl-indolin-2-one; | 9.0 |
| 129 | 5-[2-(Difluoromethoxy)-6-methyl-phenyl]-7-methyl-indolin-2-one; | 8.5 |
| 130 | 5-[2-(Difluoromethoxy)-6-methoxy-phenyl]-7-methyl-indolin-2-one; | 7.9 |
| 131 | 5-[2-(Difluoromethoxy)-6-fluoro-phenyl]-7-methyl-indolin-2-one; | 8.3 |
| 132 | 2-[3-Chloro-2-(7-methyl-2-oxo-indolin-5-yl)phenyl]-2-methyl-propanenitrile; | 9.3 |
| 133 | 4-Chloro-3-(7-methyl-2-oxo-indolin-5-yl)-2-(trifluoromethoxy)benzonitrile; | 9.9 |
| 134 | 2-Methyl-3-(7-methyl-2-oxo-indolin-5-yl)benzonitrile; | 7.0 |
| 135 | 5-(2-Chloro-6-methyl-phenyl)-7-methyl-indolin-2-one; | 9.4 |
| 136 | 5-(2-Fluoro-6-methyl-phenyl)-7-methyl-indolin-2-one; | 8.5 |
| 137 | 7-Methyl-5-[2-methyl-6-(trifluoromethyl)phenyl]indolin-2-one; | 8.9 |
| 138 | 3-Methyl-2-(7-methyl-2-oxo-indolin-5-yl)benzonitrile; | 8.6 |
| 139 | 5-(2-Fluoro-6-methoxy-phenyl)-7-methyl-indolin-2-one; | 6.9 |
| 140 | 5-(2,6-Difluorophenyl)-7-methyl-indolin-2-one; | 6.5 |
| 141 | 5-(2-Chloro-6-fluoro-phenyl)-7-methyl-indolin-2-one; | 8.7 |
| 142 | 5-(2,6-Dimethylphenyl)-7-methyl-indolin-2-one; | 8.6 |
| 143 | 3-Chloro-2-(7-methyl-2-oxo-indolin-5-yl)benzonitrile; | 8.3 |
| 144 | 5-[3,5-Dichloro-2-(trifluoromethyl)-4-pyridyl]-7-methyl-indolin-2-one; | 7.9 |
| 145 | 5-[3-Chloro-5-(trifluoromethoxy)-4-pyridyl]-7-methyl-indolin-2-one; | 8.5 |
| 146 | 5-[3-Chloro-5-(difluoromethoxy)-4-pyridyl]-7-methyl-indolin-2-one; | 8.1 |
| 147 | 5-(3,5-Dichloro-4-pyridyl)-7-methyl-indolin-2-one; | 8.1 |
| 148 | 5-(3,5-Dimethyl-4-pyridyl)-7-methyl-indolin-2-one; | 8.0 |
| 149 | 5-(2-Chloro-4-methyl-3-pyridyl)-7-methyl-indolin-2-one; | 7.8 |
| 150 | 5-(2-Methoxy-4-methyl-3-pyridyl)-7-methyl-indolin-2-one; | 7.5 |
| 151 | 5-(2,4-Dimethyl-3-pyridyl)-7-methyl-indolin-2-one; | 6.2 |
| 152 | 5-(2,4-Dichloro-3-pyridyl)-7-methyl-indolin-2-one; | 8.5 |
| 153 | 7-Chloro-5-[2-chloro-6-(trifluoromethoxy)phenyl]indolin-2-one; | 10.1 |
| 154 | 7-Chloro-5-[2-chloro-6-(difluoromethoxy)phenyl]indolin-2-one; | 9.5 |
| 155 | 2-[3-Chloro-2-(7-chloro-2-oxo-indolin-5-yl)phenyl]-2-methyl-propanenitrile; | 9.8 |
| 156 | 4-Chloro-3-(7-chloro-2-oxo-indolin-5-yl)-2-(trifluoromethoxy)benzonitrile; | 10.1 |
| 157 | 7-Chloro-5-[3-chloro-5-(trifluoromethoxy)-4-pyridyl]indolin-2-one; | 8.2 |
| 158 | 7-Chloro-5-[3-chloro-5-(difluoromethoxy)-4-pyridyl]indolin-2-one; | 8.1 |
| 159 | 7-Chloro-5-(3,5-dichloro-4-pyridyl)indolin-2-one; | 8.1 |
| 160 | 7-Chloro-5-(2-chloro-4-methyl-3-pyridyl)indolin-2-one; | 8.2 |
| 161 | 7-Chloro-5-(2,4-dimethyl-3-pyridyl)indolin-2-one; | 6.8 |
| 162 | 7-Chloro-5-(2-methoxy-4-methyl-3-pyridyl)indolin-2-one; | 8.1 |
| 163 | 7-Chloro-5-(2,4-dichloro-3-pyridyl)indolin-2-one; | 8.8 |
| 164 | 2-(7-Chloro-2-oxo-indolin-5-yl)-3-methyl-benzonitrile; | 8.8 |
| 165 | 7-Chloro-5-(2-chloro-6-methyl-phenyl)indolin-2-one; | 10.2 |
| 166 | 7-Chloro-5-(2-fluoro-6-methyl-phenyl)indolin-2-one; | 9.1 |
| 167 | 7-Chloro-5-[2-methyl-6-(trifluoromethyl)phenyl]indolin-2-one; | 9.5 |
| 168 | 5-[2-Chloro-6-(trifluoromethoxy)phenyl]-7-ethyl-indolin-2-one; | 10.3 |
| 169 | 2-(7-Ethyl-2-oxo-indolin-5-yl)-3-methyl-benzonitrile; | 8.5 |
| 170 | 5-(2-Chloro-6-methyl-phenyl)-7-ethyl-indolin-2-one; | 9.6 |
| 171 | 7-Ethyl-5-(2-fluoro-6-methyl-phenyl)indolin-2-one; | 8.8 |
| 172 | 7-Ethyl-5-[2-methyl-6-(trifluoromethyl)phenyl]indolin-2-one; | 9.7 |
| 173 | 5-(3,5-Dimethyl-4-pyridyl)-7-ethyl-indolin-2-one; | 7.8 |
| 174 | 5-(3,5-Dichloro-4-pyridyl)-7-ethyl-indolin-2-one; | 8.3 |
| 175 | 5-[2-Chloro-6-(trifluoromethoxy)phenyl]-2-oxo-indoline-7-carbonitrile; | 9.2 |
| 176 | 5-[2-Chloro-6-(trifluoromethoxy)phenyl]-7-(trifluoromethyl)indolin-2-one; | 9.3 |
| 177 | 5-[2-Chloro-6-(trifluoromethoxy)phenyl]-7-(trifluoromethoxy)indolin-2-one; | 9.7 |
| 178 | 5-[2-Chloro-6-(trifluoromethoxy)phenyl]-7-methoxy-indolin-2-one; and | 9.1 |
| 179 | 5-[2-Chloro-3-(4-methoxy-1-piperidyl)phenyl]indolin-2-one. | 5.2 |

NT means not tested

Electrophysiology Assay

The effects of selected compounds upon endogenous γ 8-containing AMPA receptor currents was evaluated using whole-cell electrophysiology on acutely-dissociated mouse hippocampal neurons. Hippocampus was chosen for this assay, since CACNG8 (the protein encoded by this gene is a type I transmembrane AMPA receptor regulatory protein i.e., TARP) is preferentially enriched in this brain region (Tomita et al. (2003). "Functional studies and distribution define a family of transmembrane AMPA receptor regulatory proteins." *J Cell Biol* 161(4): 805-816.2003).

Hippocampi were dissected from C57black6 mice at 4-12 weeks postnatal, following the protocol described by Brewer (Brewer, G. J. (1997). "Isolation and culture of adult rat hippocampal neurons." *Journal of Neuroscience Methods* 71(2): 143-155). The following is a brief summary of the procedure. Mice were asphyxiated with $CO_2$ then decapitated. The brain was rapidly removed, then placed into ice-cold HABG medium. The recipe for HABG medium was: HibernateA supplemented with 2% B27 and 0.5 mM Glutamax (all reagents from Life Technologies). Hippocampi were micro-dissected from the brains, then washed with HABG without calcium (Hibernate A minus Calcium, BrainBits; 2% B27, Life Technologies; 0.5 mM glutamax, Life Technologies).

The hippocampi were then transferred to HABG without calcium, supplemented with 2 mg/mL papain (Worthington Biochemical). They were incubated at 30° C. on a roller for 40 min, then gently triturated with a fire-polished glass pipette. The supernatant containing dissociated neurons was collected, then centrifuged for 2 min at 200 g. The cell pellet was collected, and then resuspended in 8 mL of HABG. Live cells were counted, then plated onto 12 mm glass coverslips in HABG (2 mL) in 24-well plates at a density of 50-100 cells per coverslip. These cells were maintained at room temperature until use.

Whole-cell electrophysiology was performed using 1.5 mm diameter glass capillary tubes (World Precision Instruments TW150-4), pulled to a fine tip with a Sutter P-97 micropipette puller. The intracellular buffer was 90 mM KF, 30 mM KCl, 10 mM HEPES, and 5 mM EGTA, pH 7.4, 290 mOs. The extracellular buffer was 135 mM NaCl, 4 mM KCl, 2 mM $CaCl_2$, 1 mM $MgCl_2$, 5 mM glucose, 10 mM HEPES, pH 7.4, 300 mOs. The open-tip resistances of the micropipettes using these solutions were 2-4MΩ. Whole-cell recordings of neuron cell bodies were performed in voltage-clamp mode using an Axon Axopatch 200B amplifier. Whole-cell current was measured holding the interior of the cell at −60 mV, using a 5 kHz lowpass filter. The cells were continuously perfused through 7 mm square glass barrels using a solenoid-controlled solution switching device (Warner Instruments, PF-77B). The peak current in response to a 500 ms exposure to 10 mM glutamate every 5 seconds was measured, before and after exposure to test compound.

For analysis, the mean peak current of 5 traces in the presence of test compound was divided by the mean peak current of 5 traces prior to the addition of test compound. Compounds were tested at concentrations at least ten times higher than their estimated potency in the calcium flux assay, in order to ensure near-saturating occupancy of the receptor.

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound of Formula (I), and pharmaceutically acceptable salts, N-oxides, or solvates thereof, (I)

wherein
$R^1$ is H or halo;
$R^6$ is a member selected from the group consisting of: H, halo, —$C_{1-5}$alkyl, —$C_{1-5}$haloalkyl, —$C_{1-5}$alkoxy, —$C_{1-5}$haloalkoxy, and —CN;
$Z^1$ and $Z^2$ are independently C or N;
wherein only one $Z^1$ or $Z^2$ may be N;

(A) when $Z^1$ and $Z^2$ are C; then
$R^2$ is a member selected from the group consisting of: -halo, —$C_{1-5}$haloalkoxy, —$C_{1-5}$haloalkyl, —CN, and —$CH_2CN$;
$R^3$ is a member selected from the group consisting of: H, halo, —$C_{1-5}$alkyl, —CN, and —$CH_2CN$;
$R^4$ is a member selected from the group consisting of: H, halo, —$C_{1-5}$alkyl, —$C_{1-5}$haloalkyl, —CN, and —$CO_2C_{1-5}$alkyl; and
$R^5$ is a member selected from the group consisting of: halo; —CH=$CH_2$; —$C_{1-5}$haloalkyl; —$C_{1-5}$haloalkoxy; —$CH_2CN$; —$CH(CH_3)CN$; —$C(CH_3)_2CN$; —O—$CH_2CN$; —$CO_2C_{1-5}$alkyl; —O-benzyl; —O-cyclopropyl, —O—$CH_2$-cyclopropyl; —O-azetidine substituted with —$CO_2tBu$; —O-thiazole, cyclopropyl substituted with —CN; -cyclobutyl substituted with —CN; phenyl; phenyl substituted with —F, —CN, or —$OCH_3$; cyclopropyl, pyridyl; pyridyl substituted with —F, —$OCH_3$ or —$CF_3$; 1-(2-methoxyethyl)pyrazol-4-yl; 3,5-dimethylisoxazol-4-yl; 2-isopropylpyrazol-3-yl; 1H-pyrazol-4-yl; 1,5-dimethylpyrazol-4-yl); pyrimidin-5-yl; —$NHCH_2$-furyl; —O—$CH_2$cyclopropyl substituted with two —F; and 1-methylpyrazol-4-yl;

(B) when $Z^1$ and $Z^2$ are C and $R^2$ is $C_{1-5}$alkyl; then
$R^3$ is selected from the group consisting of: H, —$C_{1-5}$haloalkyl, —CN, and —$CO_2C_{1-5}$alkyl;
$R^4$ is selected from the group consisting of: H, halo, —CN, and —$CO_2C_{1-5}$alkyl; and
$R^5$ is selected from the group consisting of: H, halo, —$C_{1-5}$alkyl, —$C_{1-5}$haloalkyl, —$C_{1-5}$alkoxy, —$C_{1-5}$haloalkoxy, —CN, —$CO_2C_{1-5}$alkyl, phenyl, 4-fluorophenyl, and 2-fluorophenyl;

(C) when $Z^1$ and $Z^2$ are C and $R^2$ is —$C_{1-5}$alkoxy; then
$R^3$ is selected from the group consisting of: H, halo, and —$CO_2C_{1-5}$alkyl;
$R^4$ is selected from the group consisting of: H, halo, —$C_{1-5}$alkyl, and —$C_{1-5}$haloalkyl; and
$R^5$ is selected from the group consisting of: halo, —$C_{1-5}$alkyl, —$C_{1-5}$haloalkyl, —$C_{1-5}$haloalkoxy, quinolinyl, —O-benzyl, and —O—$CH_2$-phenyl substituted with —F;

(D) when $Z^1$ and $Z^2$ are C and $R^5$ is H; then
$R^2$ is selected from the group consisting of: halo, —$C_{1-5}$alkyl, —$C_{1-5}$haloalkyl, —$C_{1-5}$alkoxy, —$C_{1-5}$haloalkoxy, —$CH_2$(C=O)NH($CH_3$), and —CN;
$R^3$ is selected from the group consisting of: halo, —CN, —$CH_2CN$, —$C_{1-5}$alkyl, —$C_{1-5}$haloalkyl, —$C_{1-5}$alkoxy, —$C_{1-5}$haloalkoxy, —$CO_2C_{1-5}$alkyl, piperidine substituted with —$OCH_3$, —O-azetidine substituted with —$CO_2tBu$, —O—$CH_2$cyclopropyl substituted with two —F, and —O-cyclopropyl; and
$R^4$ is selected from the group consisting of: H, halo, —CN, —$C_{1-5}$alkyl, —$C_{1-5}$haloalkyl, and —$CO_2C_{1-5}$alkyl;

(E) when one of $Z^1$ or $Z^2$ is N;
  $R^2$ is a member selected from the group consisting of: halo, —$C_{1-5}$alkyl, and —$C_{1-5}$alkoxy;
  $R^3$ is H or —$C_{1-5}$haloalkyl; and
  $R^4$ is a member selected from the group consisting of: H and —$C_{1-5}$haloalkoxy;
  $R^5$ is a member selected from the group consisting of: —$C_{1-5}$alkyl, —$C_{1-5}$haloalkoxy, and -halo; and
  wherein when $Z^1$ is N, $R^3$ is absent;
or
(F) when $Z^1$ and $Z^2$ are C, and $R^3$ and $R^5$ are H; then
  $R^2$ is a member selected from the group consisting of: halo, —$C_{1-5}$alkyl and —$C_{1-5}$alkoxy; and
  $R^4$ is a member selected from the group consisting of: halo, —$C_{1-5}$alkyl, —$C_{1-5}$haloalkyl, —CN and —$CO_2C_{1-5}$alkyl.

2. The compound of claim 1, wherein $R^1$ is H.
3. The compound of claim 1, wherein $R^1$ is halo.
4. The compound of claim 1, wherein $R^1$ is —Br or —F.
5. The compound of claim 1, wherein $R^6$ is H.
6. The compound of claim 1, wherein $R^6$ is H, halo, —$CH_3$, —$CF_3$, —$OCH_3$, —$OCF_3$, and —CN.
7. The compound of claim 1, wherein $R^1$ and $R^6$ are H.
8. The compound of claim 1, wherein $Z^1$ and $Z^2$ are C and $R^2$, $R^3$, $R^4$, and $R^5$ are defined according to (A) of claim 1.
9. The compound of claim 1, wherein $Z^1$ and $Z^2$ are C and $R^2$, $R^4$, and $R^5$ are defined according to (A) of claim 1, and $R^3$ is H, —Cl, —CN, —$CH_3$, or —$CH_2CN$.
10. The compound of claim 1, wherein $Z^1$ and $Z^2$ are C, $R^2$, $R^4$, and $R^5$ are defined according to (A) of claim 1, and $R^3$ is H, —CN.
11. The compound of claim 1, wherein $Z^1$ and $Z^2$ are C, $R^2$ and $R^3$ are defined according to (A) of claim 1, and $R^5$ is —Cl, —Br, —F, —$CH_2CN$, —$CH(CH_3)CN$, —$OCF_2H$, —$OCF_3$, —CH=$CH_2$, —O—$CH_2CF_3$, —O—$CH_2CF_2H$, —OCH($CH_3$)$CF_3$, —$CF_3$, —O-benzyl, —$CO_2CH_3$, —$OCH_2CN$, cyclopropyl, phenyl,

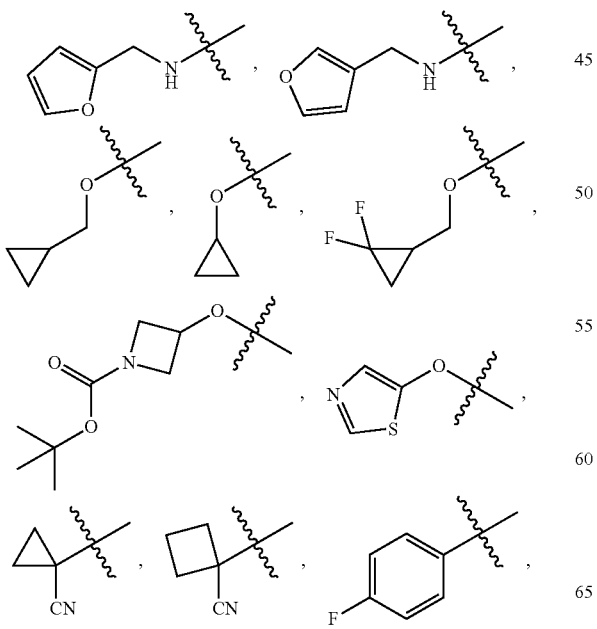

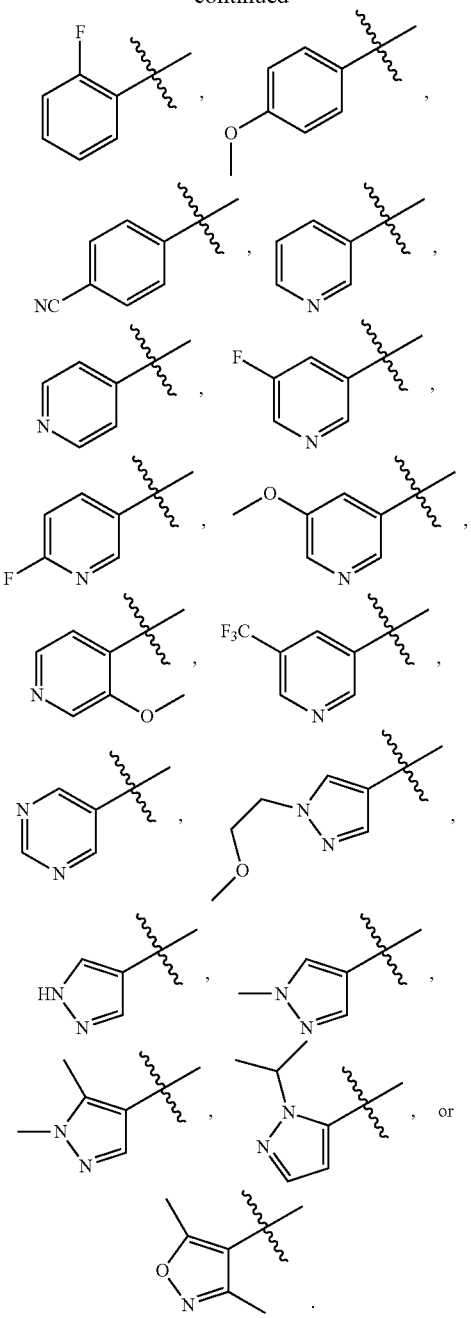

12. The compound of claim 1, wherein $Z^1$ and $Z^2$ are C, $R^2$ and $R^3$, are defined according to (A) of claim 1, and $R^5$ is —Cl, —Br, —F, —$CH_2CN$, —$CH(CH_3)CN$, —$OCF_2H$, or —$OCF_3$.
13. The compound of claim 1, wherein $Z^1$ and $Z^2$ are C, and $R^2$, $R^3$, $R^4$, and $R^5$ are defined according to (B) of claim 1.
14. The compound of claim 1, wherein $Z^1$ and $Z^2$ are C and $R^2$, $R^3$, $R^4$, and $R^5$ are defined according to (C) of claim 1.
15. The compound of claim 1, wherein $Z^1$ and $Z^2$ are C and $R^2$, $R^3$, $R^4$, and $R^5$ are defined according to (D) of claim 1.
16. The compound of claim 1, wherein $Z^1$ is N, $Z^2$ is C, and $R^2$, $R^4$, and $R^5$ are defined according to (E) of claim 1.

17. The compound of claim 1, wherein $Z^1$ is C, $Z^2$ is N, and $R^2$, $R^4$, and $R^5$ are defined according to (E) of claim 1.

18. The compound of claim 1, wherein $Z^2$ is C, $Z^1$ is N, $R^4$ is H, $R^5$ is defined according to (E) of claim 1, and $R^2$ is —Cl, —OCH$_3$, or —CH$_3$.

19. The compound of claim 14, wherein $R^6$ is —H, —F, or —CH$_3$.

20. The compound of claim 1, as defined in (A), having the structure of Formula (II), and pharmaceutically acceptable salts, N-oxides, or solvates thereof,

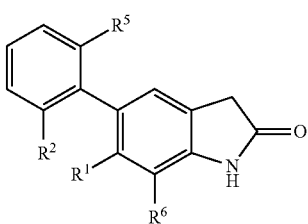

(II)

wherein $R^2$ is halo, —C$_{1-5}$haloalkoxy or —CN; and $R^5$ is halo, —CH$_2$CN, or —C(CH$_3$)$_2$CN.

21. The compound of claim 1, as defined in (B), having the structure of Formula (II), and pharmaceutically acceptable salts, N-oxides, or solvates thereof,

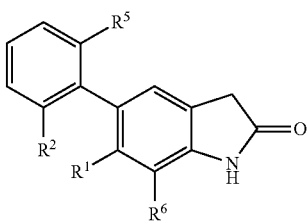

(II)

wherein $R^2$ is —C$_{1-5}$alkyl; and $R^5$ is halo, —C$_{1-5}$alkyl, —C$_{1-5}$haloalkyl, —C$_{1-5}$haloalkoxy or —CN.

22. The compound of claim 1, as defined in (C), having the structure of Formula (II), and pharmaceutically acceptable salts, N-oxides, or solvates thereof,

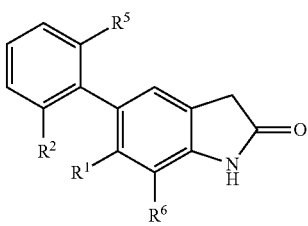

(II)

$R^2$ is —C$_{1-5}$alkoxy; and $R^5$ is —C$_{1-5}$haloalkoxy.

23. A compound of claim 1 having the structure of Formula (III), and pharmaceutically acceptable salts, N-oxides, or solvates thereof,

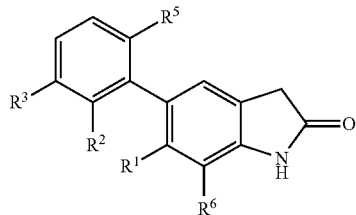

(III)

wherein $R^2$ is halo or —C$_{1-5}$haloalkoxy;

$R^3$ is —CN; and $R^5$ is halo.

24. A compound of Formula (IA), and pharmaceutically acceptable salts, N-oxides, or solvates thereof,

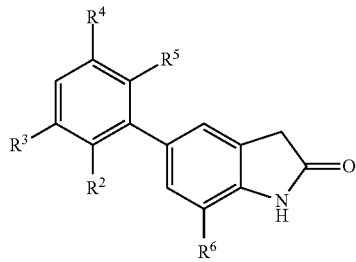

(IA)

wherein:

$R^2$ is halo, —C$_{1-5}$alkyl, —CN, or —C$_{1-5}$haloalkoxy;

$R^3$ is H or —CN;

$R^4$ is H;

$R^5$ is halo, —C$_{1-5}$alkyl, —C$_{1-5}$haloalkyl, —C$_{1-5}$alkoxy, —CN, —C(CH$_3$)$_2$CN; and $R^6$ is H, halo, —C$_{1-5}$alkyl, —C$_{1-5}$haloalkyl, —C$_{1-5}$alkoxy, —C$_{1-5}$haloalkoxy or —CN.

25. A compound selected from the group consisting of:

5-(2,6-Dimethylphenyl)indolin-2-one;
5-(2-Bromo-6-chlorophenyl)indolin-2-one;
5-(2-Chloro-6-methyl-phenyl)indolin-2-one;
5-(2,6-Dichlorophenyl)indolin-2-one;
5-[2-Chloro-6-(trifluoromethoxy)phenyl]indolin-2-one;
2-[3-Chloro-2-(2-oxoindolin-5-yl)phenyl]acetonitrile;
2-[3-Chloro-2-(2-oxoindolin-5-yl)phenyl]-2-methyl-propanenitrile;
4-Chloro-3-(2-oxoindolin-5-yl)-2-(trifluoromethoxy)benzonitrile;
5-(2-Chloro-6-(trifluoromethoxy)phenyl)-6-fluoroindolin-2-one;
5-(2-Chloro-6-(trifluoromethoxy)phenyl)-7-fluoroindolin-2-one;
5-(2-Chloro-6-(difluoromethoxy)phenyl)-7-fluoroindolin-2-one;
2-(3-Chloro-2-(7-fluoro-2-oxoindolin-5-yl)phenyl)-2-methylpropanenitrile;
6-Bromo-5-(2-chloro-6-(trifluoromethoxy)phenyl)indolin-2-one;
5-(2-Chloro-3-(4-methoxypiperidin-1-yl)phenyl)-7-fluoroindolin-2-one;
5-[2-(Difluoromethoxy)-6-methyl-phenyl]-7-fluoro-indolin-2-one;
5-[2-(Difluoromethoxy)-6-methoxy-phenyl]-7-fluoro-indolin-2-one;
2-Chloro-3-(7-fluoro-2-oxo-indolin-5-yl)-4-(trifluoromethoxy)benzonitrile;

5-(3,5-Dimethyl-4-pyridyl)-7-fluoro-indolin-2-one;
5-(3,5-Dichloro-4-pyridyl)-7-fluoro-indolin-2-one;
5-[2-Chloro-6-(trifluoromethoxy)phenyl]-7-methyl-indolin-2-one;
5-[2-Chloro-6-(difluoromethoxy)phenyl]-7-methyl-indolin-2-one;
5-[2-(Difluoromethoxy)-6-methyl-phenyl]-7-methyl-indolin-2-one;
5-[2-(Difluoromethoxy)-6-methoxy-phenyl]-7-methyl-indolin-2-one;
5-[2-(Difluoromethoxy)-6-fluoro-phenyl]-7-methyl-indolin-2-one;
2-[3-Chloro-2-(7-methyl-2-oxo-indolin-5-yl)phenyl]-2-methyl-propanenitrile;
4-Chloro-3-(7-methyl-2-oxoindolin-5-yl)-2-(trifluoromethoxy)benzonitrile;
2-Methyl-3-(7-methyl-2-oxo-indolin-5-yl)benzonitrile;
5-(2-Chloro-6-methyl-phenyl)-7-methyl-indolin-2-one;
5-(2-Fluoro-6-methyl-phenyl)-7-methyl-indolin-2-one;
7-Methyl-5-[2-methyl-6-(trifluoromethyl)phenyl]indolin-2-one;
3-Methyl-2-(7-methyl-2-oxo-indolin-5-yl)benzonitrile;
5-(2-Fluoro-6-methoxy-phenyl)-7-methyl-indolin-2-one;
5-(2,6-Difluorophenyl)-7-methyl-indolin-2-one;
5-(2-Chloro-6-fluoro-phenyl)-7-methyl-indolin-2-one;
5-(2,6-Dim ethylphenyl)-7-methyl-indolin-2-one;
3-Chloro-2-(7-methyl-2-oxoindolin-5-yl)benzonitrile;
5-[3,5-Dichloro-2-(trifluoromethyl)pyridin-4-yl]-7-methyl indolin-2-one;
5-[3-Chloro-5-(trifluoromethoxy)-4-pyridyl]-7-methyl-indolin-2-one;
5-(3-Chloro-5-(difluoromethoxy)pyridin-4-yl)-7-methyl-indolin-2-one;
5-(3,5-Dichloro-4-pyridyl)-7-methyl-indolin-2-one;
5-(3,5-Dimethyl-4-pyridyl)-7-methyl-indolin-2-one;
5-(2-Chloro-4-methyl-3-pyridyl)-7-methyl-indolin-2-one;
5-(2-Methoxy-4-methyl-3-pyridyl)-7-methyl-indolin-2-one;
5-(2,4-Dimethyl-3-pyridyl)-7-methyl-indolin-2-one;
5-(2,4-Dichloro-3-pyridyl)-7-methyl-indolin-2-one;
7-Chloro-5-[2-chloro-6-(trifluoromethoxy)phenyl]indolin-2-one;
7-Chloro-5-[2-chloro-6-(difluoromethoxy)phenyl]indolin-2-one;
2-[3-Chloro-2-(7-chloro-2-oxo-indolin-5-yl)phenyl]-2-methyl-propanenitrile;
4-Chloro-3-(7-chloro-2-oxo-indolin-5-yl)-2-(trifluoromethoxy)benzonitrile;
7-Chloro-5-(3-chloro-5-(trifluoromethoxy)pyridin-4-yl)indolin-2-one;
7-Chloro-5-[3-chloro-5-(difluoromethoxy)-4-pyridyl]indolin-2-one;
7-Chloro-5-(3,5-dichloro-4-pyridyl)indolin-2-one;
7-Chloro-5-(2-chloro-4-methyl-3-pyridyl)indolin-2-one;
7-Chloro-5-(2,4-dimethyl-3-pyridyl) indolin-2-one;
7-Chloro-5-(2-methoxy-4-methyl-3-pyridyl)indolin-2-one;
7-Chloro-5-(2,4-dichloro-3-pyridyl)indolin-2-one;
2-(7-Chloro-2-oxo-indolin-5-yl)-3-methyl-benzonitrile;
7-Chloro-5-(2-chloro-6-methyl-phenyl)indolin-2-one;
7-Chloro-5-(2-fluoro-6-methyl-phenyl)indolin-2-one;
7-Chloro-5-[2-methyl-6-(trifluoromethyl)phenyl]indolin-2-one;
5-[2-Chloro-6-(trifluoromethoxy)phenyl]-7-ethyl-indolin-2-one;
2-(7-Ethyl-2-oxo-indolin-5-yl)-3-methyl-benzonitrile;
5-(2-Chloro-6-methyl-phenyl)-7-ethyl-indolin-2-one;
7-Ethyl-5-(2-fluoro-6-methyl-phenyl)indolin-2-one;
7-Ethyl-5-[2-methyl-6-(trifluoromethyl)phenyl]indolin-2-one;
5-(3,5-Eimethyl-4-pyridyl)-7-ethyl-indolin-2-one;
5-(3,5-Dichloro-4-pyridyl)-7-ethyl-indolin-2-one;
5-[2-Chloro-6-(trifluoromethoxy)phenyl]-2-oxo-indoline-7-carbonitrile;
5-[2-Chloro-6-(trifluoromethoxy)phenyl]-7-(trifluoromethyl)indolin-2-one;
5-[2-Chloro-6-(trifluoromethoxy)phenyl]-7-(trifluoromethoxy)indolin-2-one;
5-[2-Chloro-6-(trifluoromethoxy)phenyl]-7-methoxy-indolin-2-one;
5-[2-Chloro-3-(4-methoxy-1-piperidyl)phenyl]indolin-2-one; and pharmaceutically acceptable salts, N-oxides, or solvates thereof.

26. A compound selected from the group consisting of:
4-Chloro-3-(2-oxoindolin-5-yl)-2-(trifluoromethoxy)benzonitrile;
5-(5-Chloro-2-methyl-phenyl)-indolin-2-one;
5-[2-Chloro-6-(trifluoromethyl)phenyl]-indolin-2-one;
5-(2-Isobutoxy-5-methyl-phenyl)-indolin-2-one;
5-(5-Chloro-2-isopropoxy-phenyl)-indolin-2-one;
5-(2,5-Dichlorophenyl)-indolin-2-one;
5-(2-Chloro-5-methyl-phenyl)-indolin-2-one;
5-[2-Isopropoxy-5-(trifluoromethyl)phenyl]-indolin-2-one;
5-(2,6-Dichloro-3-methyl-phenyl)-indolin-2-one;
5-[2-Chloro-5-(trifluoromethyl)phenyl]-indolin-2-one;
5-(2-Benzyloxy-6-fluoro-phenyl)-indolin-2-one;
5-[3-Chloro-2-(trifluoromethoxy)phenyl]-indolin-2-one;
5-[3-Chloro-2-(trifluoromethyl)phenyl]-indolin-2-one;
5-(2-Chloro-6-methyl-phenyl)-indolin-2-one;
3-Methyl-2-(2-oxoindolin-5-yl)benzonitrile;
4-Methyl-3-(2-oxoindolin-5-yl)benzonitrile;
4-Chloro-3-(2-oxoindolin-5-yl)benzonitrile;
Methyl 3-chloro-2-(2-oxoindolin-5-yl)benzoate;
Methyl 2-chloro-3-(2-oxoindolin-5-yl)benzoate;
Methyl 4-chloro-3-(2-oxoindolin-5-yl)benzoate;
Methyl 3-methyl-2-(2-oxoindolin-5-yl)benzoate;
Methyl 2-methyl-3-(2-oxoindolin-5-yl)benzoate;
Methyl 4-methyl-3-(2-oxoindolin-5-yl)benzoate;
Methyl 2-methoxy-3-(2-oxoindolin-5-yl)benzoate;
5-(2,6-Difluorophenyl)-indolin-2-one;
5-(2-Chloro-6-fluoro-phenyl)-indolin-2-one;
5-(2-Fluoro-6-methyl-phenyl)-indolin-2-one;
5-(2-Fluoro-6-methoxy-phenyl)-indolin-2-one;
3-Chloro-2-(2-oxoindolin-5-yl)benzonitrile;
5-[2-Methyl-6-(trifluoromethyl)phenyl]-indolin-2-one;
5-(8-Quinolyl)-indolin-2-one;
5-[2-Methyl-3-(trifluoromethyl)phenyl]-indolin-2-one;
5-[2-Chloro-3-(trifluoromethyl)phenyl]-indolin-2-one;
2-Isopropoxy-6-(2-oxoindolin-5-yl)benzonitrile;
2-Bromo-6-(2-oxoindolin-5-yl)benzonitrile;
5-(2-Chloro-3-methyl-phenyl)-indolin-2-one;
2-(2-Oxoindolin-5-yl)-6-(trifluoromethyl)benzonitrile;
5-(2,3,6-Trichlorophenyl)-indolin-2-one;
2-Methyl-3-(2-oxoindolin-5-yl)benzonitrile;
2-Chloro-3-(2-oxoindolin-5-yl)benzonitrile;
5-(3,5-Dichloro-4-pyridyl)-indolin-2-one;
5-(2-Chloro-4-methyl-3-pyridyl)-indolin-2-one;
N-Methyl-2-[2-(2-oxoindolin-5-yl)-6-(trifluoromethyl)phenyl]acetamide;
5-[2-Chloro-6-(2-furylmethylamino)phenyl]-indolin-2-one;

5-[2-Chloro-6-(3-furylmethylamino)phenyl]-indolin-2-one;
5-[2-Isopropoxy-6-(trifluoromethoxy)phenyl]-indolin-2-one;
5-[2-(Cyclopropylmethoxy)-6-(trifluoromethoxy)phenyl]-indolin-2-one;
5-[2-Chloro-6-(cyclopropoxy)phenyl]-indolin-2-one;
5-[2-Chloro-6-(cyclopropylmethoxy)phenyl]-indolin-2-one;
(±)-5-[2-Chloro-6-[(2,2-difluorocyclopropyl)methoxy]phenyl]-indolin-2-one;
5-[2-Chloro-6-(difluoromethoxy)phenyl]-indolin-2-one;
5-[2-Chloro-6-(2,2,2-trifluoroethoxy)phenyl]-indolin-2-one;
5-[2-Chloro-6-(2,2-difluoroethoxy)phenyl]-indolin-2-one;
2-[3-Chloro-2-(2-oxoindolin-5-yl)phenoxy]acetonitrile;
5-(2-Benzyloxy-6-chloro-phenyl)-indolin-2-one;
tert-Butyl 3-[3-chloro-2-(2-oxoindolin-5-yl)phenoxy]azetidine-1-carboxylate;
5-(2-Chloro-6-thiazol-5-yloxy-phenyl)-indolin-2-one;
5-[2-(2,2-Difluoroethoxy)-6-methoxy-phenyl]-indolin-2-one;
5-[2-Methoxy-6-(2,2,2-trifluoroethoxy)phenyl]-indolin-2-one;
5-(2-Benzyloxy-6-methoxy-phenyl)-indolin-2-one;
5-[2-[(4-Fluorophenyl) ethoxy]-6-methoxy-phenyl]-indolin-2-one;
5-[2-Isopropoxy-6-(trifluoromethyl)phenyl]-indolin-2-one;
5-[2-Chloro-3-(cyclopropoxy)phenyl]-indolin-2-one;
5-(2-Chloro-3-isopropoxy-phenyl)-indolin-2-one;
(±)-5-[2-Chloro-3-[(2,2-difluorocyclopropyl)methoxy]phenyl]-indolin-2-one;
5-[2-Chloro-3-(2,2-difluoroethoxy)phenyl]-indolin-2-one;
5-[2-Chloro-3-(difluoromethoxy)phenyl]-indolin-2-one;
tert-Butyl 3-[2-chloro-3-(2-oxoindolin-5-yl)phenoxy]azetidine-1-carboxylate;
5-(3-Chloro-2-isopropoxy-phenyl)-indolin-2-one;
(±)-5-[2-Chloro-6-(2,2,2-trifluoro-1-methyl-ethoxy)phenyl]-indolin-2-one;
(±)-5-[2-Methoxy-6-(2,2,2-trifluoro-1-methyl-ethoxy)phenyl]-indolin-2-one;
2-[3,4-Dichloro-2-(2-oxoindolin-5-yl)phenyl]acetonitrile;
2-[2-(2-Oxoindolin-5-yl)-3-trifluoromethoxy)phenyl]acetonitrile;
(±)-2-[3-Chloro-2-(2-oxoindolin-5-yl)phenyl]propanenitrile;
1-[3-Chloro-2-(2-oxoindolin-5-yl)phenyl]cyclopropanecarbonitrile;
1-[3-Chloro-2-(2-oxoindolin-5-yl)phenyl]cyclobutanecarbonitrile;
2-[2-Chloro-3-(2-oxoindolin-5-yl)phenyl]acetonitrile;
2-[2,4-Dichloro-3-(2-oxoindolin-5-yl)phenyl]acetonitrile;
2-[3-Bromo-2-(2-oxoindolin-5-yl)phenyl]acetonitrile;
2-[3-(4-Fluorophenyl)-2-(2-oxoindolin-5-yl)phenyl]acetonitrile;
2-[3-(2-Fluorophenyl)-2-(2-oxoindolin-5-yl)phenyl]acetonitrile;
2-[3-(4-Methoxyphenyl)-2-(2-oxoindolin-5-yl)phenyl]acetonitrile;
2-[3-Cyclopropyl-2-(2-oxoindolin-5-yl)phenyl]acetonitrile;
5-(2-Chloro-6-cyclopropyl-phenyl)-indolin-2-one;
5-(2-Chloro-6-vinyl-phenyl)-indolin-2-one;
5-(2-Chloro-6-phenyl-phenyl)-indolin-2-one;
5-[2-Chloro-6-(4-fluorophenyl)phenyl]-indolin-2-one;
4-[3-Chloro-2-(2-oxoindolin-5-yl)phenyl]benzonitrile;
5-[2-Chloro-6-(3-pyridyl)phenyl]-indolin-2-one;
5-[2-Chloro-6-(5-fluoro-3-pyridyl)phenyl]-indolin-2-one;
5-[2-Chloro-6-(6-fluoro-3-pyridyl)phenyl]-indolin-2-one;
5-[2-Chloro-6-(5-methoxy-3-pyridyl)phenyl]-indolin-2-one;
5-[2-Chloro-6-[5-(trifluoromethyl)-3-pyridyl]phenyl]-indolin-2-one;
5-[2-Chloro-6-(4-pyridyl)phenyl]-indolin-2-one;
5-[2-Chloro-6-(3-methoxy-4-pyridyl)phenyl]-indolin-2-one;
5-[2-Chloro-6-[1-(2-methoxyethyl)pyrazol-4-yl]phenyl]-indolin-2-one;
5-[2-Chloro-6-(1-methylpyrazol-4-yl)phenyl]-indolin-2-one;
5-[2-Chloro-6-(3,5-dimethyl isoxazol-4-yl)phenyl]-indolin-2-one;
5-[2-Chloro-6-(2-isopropylpyrazol-3-yl)phenyl]-indolin-2-one;
5-[2-Chloro-6-(1H-pyrazol-4-yl)phenyl]-indolin-2-one;
5-[2-Chloro-6-(1,5-dimethylpyrazol-4-yl)phenyl]-indolin-2-one;
5-(2-Chloro-6-pyrimidin-5-yl-phenyl)-indolin-2-one;
5-(2-Methyl-6-phenyl-phenyl)-indolin-2-one;
5-[2-(2-Fluorophenyl)-6-methyl-phenyl]-indolin-2-one;
5-[2-(4-Fluorophenyl)-6-methyl-phenyl]-indolin-2-one;
5-[2-Methoxy-6-(8-quinolyl)phenyl]-indolin-2-one;
2-Chloro-3-(2-oxoindolin-5-yl)-4-(trifluoromethoxy)benzonitrile;
5-(2-Chloro-6-(trifluoromethoxy)phenyl)-6-fluoroindolin-2-one;
6-Bromo-5-(2-chloro-6-(trifluoromethoxy)phenyl)indolin-2-one;
2-Chloro-3-(7-methyl-2-oxoindolin-5-yl)-4-(trifluoromethoxy)benzonitrile;
2-Chloro-3-(7-chloro-2-oxoindolin-5-yl)-4-(trifluoromethoxy)benzonitrile;
7-Chloro-5-(3,5-dimethylpyridin-4-yl)indolin-2-one;
7-Chloro-5-(4-chloro-2-methoxypyridin-3-yl)indolin-2-one; and
7-Methyl-5-(4-chloro-2-methoxypyridin-3-yl)indolin-2-one;
and pharmaceutically acceptable salts, N-oxides, or solvates thereof.

27. The compound of claim 25, wherein the compound is:
5-[2-Chloro-6-(trifluoromethoxy)phenyl]-7-methyl-indolin-2-one;
and pharmaceutically acceptable salts, N-oxides, or solvates thereof.

28. The compound of claim 25, wherein the compound is:
5-[2-Chloro-6-(difluoromethoxy)phenyl]-7-methyl-indolin-2-one;
and pharmaceutically acceptable salts, N-oxides, or solvates thereof.

29. The compound of claim 25, wherein the compound is:
5-[3-Chloro-5-(trifluoromethoxy)-4-pyridyl]-7-methyl-indolin-2-one;
and pharmaceutically acceptable salts, N-oxides, or solvates thereof.

30. The compound of claim 25, wherein the compound is:
5-[3-Chloro-5-(difluoromethoxy)-4-pyridyl]-7-methyl-indolin-2-one;
and pharmaceutically acceptable salts, N-oxides, or solvates thereof.

31. The compound of claim 25, wherein the compound is:
5-(3,5-Dichloro-4-pyridyl)-7-methyl-indolin-2-one;
and pharmaceutically acceptable salts, N-oxides, or solvates thereof.

32. The compound of claim 25, wherein the compound is:
7-Chloro-5-[2-chloro-6-(trifluoromethoxy)phenyl]indolin-2-one;
and pharmaceutically acceptable salts, N-oxides, or solvates thereof.

33. The compound of claim 25, wherein the compound is:
7-Chloro-5-[2-chloro-6-(difluoromethoxy)phenyl]indolin-2-one;
and pharmaceutically acceptable salts, N-oxides, or solvates thereof.

34. The compound of claim 25, wherein the compound is:
7-Chloro-5-[3-chloro-5-(trifluoromethoxy)-4-pyridyl]indolin-2-one;
and pharmaceutically acceptable salts, N-oxides, or solvates thereof.

35. The compound of claim 25, wherein the compound is:
7-Chloro-5-[3-chloro-5-(difluoromethoxy)-4-pyridyl]indolin-2-one;
and pharmaceutically acceptable salts, N-oxides, or solvates thereof.

36. The compound of claim 25, wherein the compound is:
7-Chloro-5-(3,5-dichloro-4-pyridyl)indolin-2-one;
and pharmaceutically acceptable salts, N-oxides, or solvates thereof.

37. A pharmaceutical composition comprising:
(A) an effective amount of at least one compound of Formula (I):

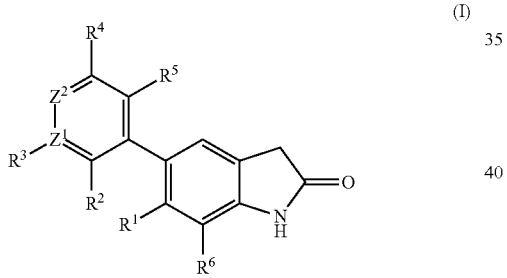

wherein
$R^1$ is H or halo;
$R^6$ is a member selected from the group consisting of: H, halo, —$C_{1-5}$alkyl, —$C_{1-5}$haloalkyl, —$C_{1-5}$alkoxy, —$C_{1-5}$haloalkoxy, and —CN;
$Z^1$ and $Z^2$ are independently C or N;
wherein only one $Z^1$ or $Z^2$ may be N;
  (A) when $Z^1$ and $Z^2$ are C; then
    $R^2$ is a member selected from the group consisting of: -halo, —$C_{1-5}$haloalkoxy, —$C_{1-5}$haloalkyl, —CN, and —$CH_2CN$;
    $R^3$ is a member selected from the group consisting of: H, halo, —$C_{1-5}$alkyl, —CN, and —$CH_2CN$;
    $R^4$ is a member selected from the group consisting of: H, halo, —$C_{1-5}$alkyl, —$C_{1-5}$haloalkyl, —CN, and —$CO_2C_{1-5}$alkyl; and
    $R^5$ is a member selected from the group consisting of: halo; —CH=$CH_2$; —$C_{1-5}$haloalkyl; —$C_{1-5}$haloalkoxy; —$CH_2CN$; —$CH(CH_3)CN$; —$C(CH_3)_2CN$; —O—$CH_2CN$; —$CO_2C_{1-5}$alkyl; —O-benzyl; —O-cyclopropyl, —O—$CH_2$-cyclopropyl; —O-azetidine substituted with —$CO_2tBu$; —O-thiazole, cyclopropyl substituted with —CN; -cyclobutyl substituted with —CN; phenyl; phenyl substituted with —F, —CN, or —$OCH_3$; cyclopropyl, pyridyl; pyridyl substituted with —F, —$OCH_3$ or —$CF_3$; 1-(2-methoxyethyl)pyrazol-4-yl; 3,5-dimethylisoxazol-4-yl; 2-isopropylpyrazol-3-yl; 1H-pyrazol-4-yl; 1,5-dimethylpyrazol-4-yl); pyrimidin-5-yl; —$NHCH_2$-furyl; —O—$CH_2$cyclopropyl substituted with two —F; and 1-methylpyrazol-4-yl;
  (B) when $Z^1$ and $Z^2$ are C and $R^2$ is $C_{1-5}$alkyl; then
    $R^3$ is selected from the group consisting of: H, —$C_{1-5}$haloalkyl, —CN, and —$CO_2C_{1-5}$alkyl;
    $R^4$ is selected from the group consisting of: H, halo, —CN, and —$CO_2C_{1-5}$alkyl; and
    $R^5$ is selected from the group consisting of: H, halo, —$C_{1-5}$alkyl, —$C_{1-5}$haloalkyl, —$C_{1-5}$alkoxy, —$C_{1-5}$haloalkoxy, —CN, —$CO_2C_{1-5}$alkyl, phenyl, 4-fluorophenyl, and 2-fluorophenyl;
  (C) when $Z^1$ and $Z^2$ are C and $R^2$ is —$C_{1-5}$alkoxy; then
    $R^3$ is selected from the group consisting of: H, halo, and —$CO_2C_{1-5}$alkyl;
    $R^4$ is selected from the group consisting of: H, halo, —$C_{1-5}$alkyl, and —$C_{1-5}$haloalkyl; and
    $R^5$ is selected from the group consisting of: halo, —$C_{1-5}$alkyl, —$C_{1-5}$haloalkyl, —$C_{1-5}$haloalkoxy, quinolinyl, —O-benzyl, and —O—$CH_2$-phenyl substituted with —F;
  (D) when $Z^1$ and $Z^2$ are C and $R^5$ is H; then
    $R^2$ is selected from the group consisting of: halo, —$C_{1-5}$alkyl, —$C_{1-5}$haloalkyl, —$C_{1-5}$alkoxy, —$C_{1-5}$haloalkoxy, —$CH_2(C=O)NH(CH_3)$, and —CN;
    $R^3$ is selected from the group consisting of: halo, —CN, —$CH_2CN$, —$C_{1-5}$alkyl, —$C_{1-5}$haloalkyl, —$C_{1-5}$alkoxy, —$C_{1-5}$haloalkoxy, —$CO_2C_{1-5}$alkyl, piperidine substituted with —$OCH_3$, —O-azetidine substituted with —$CO_2tBu$, —O—$CH_2$cyclopropyl substituted with two —F, and —O-cyclopropyl; and
    $R^4$ is selected from the group consisting of: H, halo, —CN, —$C_{1-5}$alkyl, —$C_{1-5}$haloalkyl, and —$CO_2C_{1-5}$alkyl;
  (E) when one of $Z^1$ or $Z^2$ is N;
    $R^2$ is a member selected from the group consisting of: halo, —$C_{1-5}$alkyl, and —$C_{1-5}$alkoxy;
    $R^3$ is H or —$C_{1-5}$haloalkyl;
    $R^4$ is a member selected from the group consisting of: H and —$C_{1-5}$haloalkoxy; and
    $R^5$ is a member selected from the group consisting of: —$C_{1-5}$alkyl, —$C_{1-5}$haloalkoxy, and -halo; and
    wherein when $Z^1$ is N, $R^3$ is absent;
or
  (F) when $Z^1$ and $Z^2$ are C, and $R^3$ and $R^5$ are H; then
    $R^2$ is a member selected from the group consisting of: halo, —$C_{1-5}$alkyl, —$C_{1-5}$alkoxy; and
    $R^4$ is a member selected from the group consisting of: halo, —$C_{1-5}$alkyl, —$C_{1-5}$haloalkyl, —CN, and —$CO_2C_{1-5}$alkyl; and
(B) at least one pharmaceutically acceptable excipient.

38. A pharmaceutical composition comprising an effective amount of at least one compound of claim 35 and at least one pharmaceutically acceptable excipient.

39. A pharmaceutical composition comprising an effective amount of at least one compound of claim 36 and at least one pharmaceutically acceptable excipient.

* * * * *